US012746356B2

(12) United States Patent
Cordero Gomez Del Campo et al.

(10) Patent No.: US 12,746,356 B2
(45) Date of Patent: Sep. 29, 2026

(54) RESPIRATORY VENTILATORY DEVICE AND METHOD OF OPERATING SAME

(71) Applicant: Soco International LLC, Las Vegas, NV (US)

(72) Inventors: Jose Luis Esteban Cordero Gomez Del Campo, Irapuato (MX); Jorge Antonio Cordero Gomez del Campo, Las Vegas, NV (US)

(73) Assignee: Soco International LLC, Las Vegas, NV (US)

( * ) Notice: Subject to any disclaimer, the term of this patent is extended or adjusted under 35 U.S.C. 154(b) by 636 days.

(21) Appl. No.: 18/219,610

(22) Filed: Jul. 7, 2023

(65) Prior Publication Data

US 2023/0347086 A1 Nov. 2, 2023

Related U.S. Application Data

(63) Continuation-in-part of application No. 17/830,093, filed on Jun. 1, 2022, now Pat. No. 12,427,275, which (Continued)

(51) Int. Cl.

| | |
|---|---|
| ***A61M 16/00*** | (2006.01) |
| ***A61M 16/08*** | (2006.01) |
| ***A61M 16/20*** | (2006.01) |

(52) U.S. Cl.

CPC ...... *A61M 16/024* (2017.08); *A61M 16/0066* (2013.01); *A61M 16/0816* (2013.01); *A61M 16/208* (2013.01)

(58) Field of Classification Search

CPC .......... A61M 16/0009; A61M 16/0051; A61M 16/0057; A61M 16/006; A61M 16/0066; (Continued)

(56) References Cited

U.S. PATENT DOCUMENTS

| | | | |
|---|---|---|---|
| 2,924,215 | A | 2/1960 | Goodner |
| 3,523,527 | A | 8/1970 | Foster |

(Continued)

FOREIGN PATENT DOCUMENTS

| | | | |
|---|---|---|---|
| DE | 2035829 | A1 | 1/1972 |
| DE | 19640113 | C1 | 10/1997 |
| GB | 1190441 | A | 5/1970 |

*Primary Examiner* — Annette Dixon

(74) *Attorney, Agent, or Firm* — Howard & Howard Attorneys PLLC

(57) ABSTRACT

A respiratory ventilator device is described herein. The respiratory ventilator device includes an inhaled air assembly including an injector diaphragm housing including a flexible injector diaphragm, an extractor diaphragm housing including a flexible extractor diaphragm, a pneumatic compressed air assembly, and a control system operatively coupled to the pneumatic compressed air assembly. The control system including a processor programmed to execute an algorithm for operating the respiratory ventilator device including the steps of operating the pneumatic compressed air assembly in a first phase including the injector diaphragm and the extractor diaphragm in a center position, and operating the pneumatic compressed air assembly in a second phase including delivering compressed air into the injector diaphragm housing to move the flexible injector diaphragm to channel inhalation air from the injector diaphragm housing to a patient respiratory circuit.

20 Claims, 64 Drawing Sheets

Related U.S. Application Data is a continuation of application No. 17/387,537, filed on Jul. 28, 2021, now Pat. No. 11,369,763.

(60) Provisional application No. 63/359,268, filed on Jul. 8, 2022, provisional application No. 63/059,636, filed on Jul. 31, 2020.

(58) Field of Classification Search

CPC .......... A61M 16/0072; A61M 16/0075; A61M 16/0078; A61M 16/0081; A61M 16/0084; A61M 16/0093; A61M 16/01; A61M 16/024; A61M 16/0808; A61M 16/0816; A61M 16/0833; A61M 16/085; A61M 16/0875; A61M 16/0883; A61M 16/1045; A61M 16/1065; A61M 16/107; A61M 16/1075; A61M 16/12; A61M 16/16; A61M 16/202; A61M 16/203; A61M 16/206; A61M 16/208; A61M 16/209; A61M 16/22; A61M 2016/0021; A61M 2016/0027; A61M 2016/0033; A61M 2016/0036; A61M 2016/0039; A61M 2205/103; A61M 2205/106; A61M 2205/18; A61M 2205/3331; A61M 2205/3382; A61M 2205/3606; A61M 2205/502; A61M 2205/505; A61M 2205/581; A61M 2205/583; A61M 2205/7536; A61M 2209/084

See application file for complete search history.

(56) References Cited

U.S. PATENT DOCUMENTS

| | | | |
|---|---|---|---|
| 3,789,837 | A | 2/1974 | Philips et al. |
| 4,340,044 | A | 7/1982 | Levy |
| 5,615,669 | A | 4/1997 | Olsson et al. |
| 5,769,072 | A | 6/1998 | Olsson et al. |
| 5,865,173 | A | 2/1999 | Froehlich |
| 5,871,009 | A | 2/1999 | Rydgren et al. |
| 5,918,596 | A | 7/1999 | Heinonen |
| 6,213,120 | B1 | 4/2001 | Block |
| 6,474,333 | B1 | 11/2002 | Heinonen |
| 6,523,538 | B1 | 2/2003 | Wikefeldt |
| 6,786,217 | B2 | 9/2004 | Stenzler |
| 7,201,166 | B2 | 4/2007 | Blaise et al. |
| 7,523,752 | B2 | 4/2009 | Montgomery et al. |
| 8,746,241 | B2 | 6/2014 | Cavendish |
| 8,893,717 | B2 | 11/2014 | Montgomery et al. |
| 11,369,763 | B2 * | 6/2022 | Cordero Gomez Del Campo ...... A61M 16/024 |
| 12,427,275 | B2 * | 9/2025 | Cordero Gomez Del Campo ...... A61M 16/0009 |
| 2011/0203589 | A1 | 8/2011 | Fenton |
| 2015/0273175 | A1 | 10/2015 | Acker et al. |
| 2015/0273176 | A1 | 10/2015 | Acker et al. |
| 2015/0314101 | A1 | 11/2015 | Acker et al. |
| 2023/0347086 | A1 | 11/2023 | Cordero Gomez Del Campo et al. |

* cited by examiner

400

| Phases of the Respiratory Cycle | | | | Component Status | | | | | | |
|---|---|---|---|---|---|---|---|---|---|---|
| | | | | Valve | | | | | | |
| Phase Number | Phase Name | Description | Trigger, Phase Change | V3 (190) | V4 (192) | V5 (160) | V6 (230) | V12 (142) | V21 (134) | V23 (164) |
| Ph1 | Post-expiratory Pause | Time elapsed between expiration end and inspiration beginning, diaphragms are in center position Solenoid valves V3, V4,V5,V6 and V12 are closed PEEP is measured in airway | Time or Negative PAW | O | O | O | O | O | O | O |
| Ph2 | Inspiration | Solenoid valves V3 and V12 open, and Proportional valve V10 opening is adjusted by the PLC in order to comply with VT set by operator | Time, Pressure or Volume | O | O | O | O | O | O | O |
| Ph3 | Post-inspiratory Pause | Time elapsed between inpiration's end and expiration's beginning, PPL measurement | Time | O | O | O | O | O | O | O |
| Ph4 | Expiration | Solenoid valves V4, V5, V6, V21 and V23 are open Soleniod valves V3 and V12 are closed by PLC when the time, pressure or flow are met | Time, Pressure or Volume | O | O | O | O | O | O | O |

FIG. 38

BEST AVAILABLE IMAGE

210

210

900

RESPIRATORY VENTILATORY DEVICE AND METHOD OF OPERATING SAME

CROSS-REFERENCE TO RELATED APPLICATION

This application is a continuation-in-part of U.S. patent application Ser. No. 17/830,093, filed Jun. 1, 2022, which is a continuation of U.S. patent application Ser. No. 17/387,537, filed Jul. 28, 2021 (Now U.S. Pat. No. 11,369,763, issued Jun. 28, 2022), which claims the benefit of Provisional Patent Application Ser. No. 63/059,636, filed Jul. 31, 2020, and claims the benefit of Provisional Patent Application Ser. No. 63/359,268, filed Jul. 8, 2022, the disclosures of which are incorporated by reference in their entirety for all purposes.

FIELD OF THE DISCLOSURE

The present invention relates to a respiratory ventilator device for use with patients. More specifically, the present invention relates to a respiratory ventilator device for use with patients requiring it as continuous ventilator support, both invasive and non-invasive. This is happening in much greater numbers since the COVID-19 Pandemic started

BACKGROUND

Known treatment protocols for patients diagnosed with coronavirus disease 2019 (COVID-19) caused by a novel coronavirus includes the use of respirator ventilators to assist patients with breathing. The current need for ventilators and the worldwide shortage of these devices due to the spread of COVID-19 and related Pneumonia, added to the regular need for these devices for non-covid-19 related Pneumonia. Known respirator ventilators are costly, putting them beyond most of world population reach. There are thousands of cases worldwide in which patients with pneumonia, covid related and not, cannot be connected to a ventilator due to all available being already in use resulting in an increase in deaths that could be avoided. It is not easy and or quick to ramp up production because ventilators currently in use are made in highly specialized facilities, which points to the need for a ventilator that can be quickly manufactured in large quantities without highly specialized labor, machinery or equipment.

The present invention is aimed at one or more of the problems identified above.

SUMMARY OF INVENTION

In one aspect of the present invention, a respiratory ventilator device is provided. The respiratory ventilator device includes an inhaled air assembly, an exhaled air assembly, and a control system operatively coupled to the inhaled air assembly and the exhaled air assembly. The inhaled air assembly is coupled to a patient respiratory circuit and configured to channel a volume of inhalation air to a patient's lungs to assist in patient inhalation. The exhaled air assembly is coupled to the respiratory circuit and configured to remove air from the patent's lungs to assist in a patient exhalation. The control system is configured to operate the respiratory ventilator system in an inhalation mode and an exhalation mode. The control system operates the inhaled air assembly to generate a positive air pressure to channel the volume of inhalation air to the patient's lungs during the inhalation mode and operates the exhaled air assembly to generate a negative air pressure to remove the air from the patent's lungs during the exhalation mode.

In another aspect of the present invention, a method of operating a respiratory ventilator device is provided. The respiratory ventilator device includes an inhaled air assembly coupled between a supply of oxygenated air and a patient respiratory circuit and an exhaled air assembly coupled between the patient respiratory circuit and an exhaust air outlet connector assembly. The method includes operating the inhaled air assembly to generate a positive air pressure to channel a volume of inhalation air to the patient's lungs during an inhalation mode and operating the exhaled air assembly to generate a negative air pressure to remove the air from the patent's lungs during an exhalation mode.

BRIEF DESCRIPTION OF THE FIGURES

Non-limiting and non-exhaustive embodiments of the present invention are described with reference to the following figures. Other advantages of the present disclosure will be readily appreciated, as the same becomes better understood by reference to the following detailed description when considered in connection with the accompanying drawings wherein:

FIGS. 37-39 are flow charts illustrating algorithms executed by the control system for use in operating the respirator ventilator device, according to one embodiment of the present invention.

Corresponding reference characters indicate corresponding components throughout the several views of the drawings.

DETAILED DESCRIPTION

Figure 1:
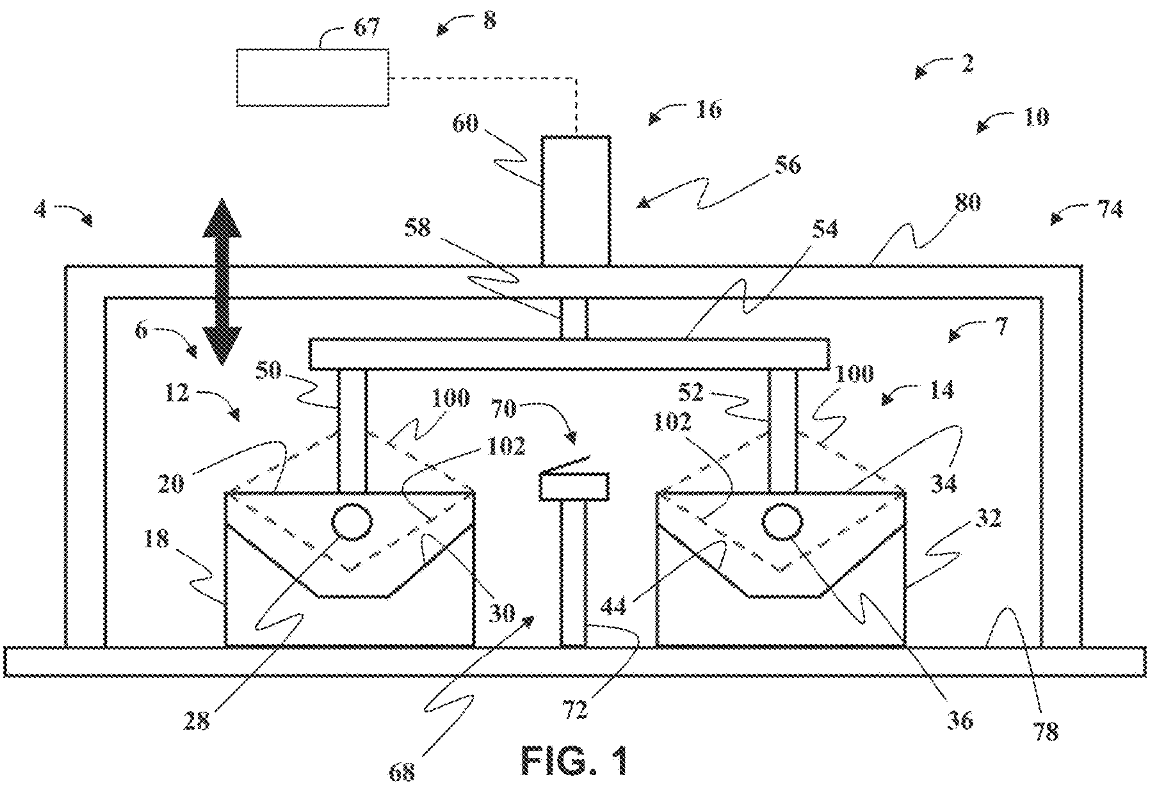
FIG. 1 is a front schematic view of a respirator ventilator device, according to the present invention.
Figure 2:
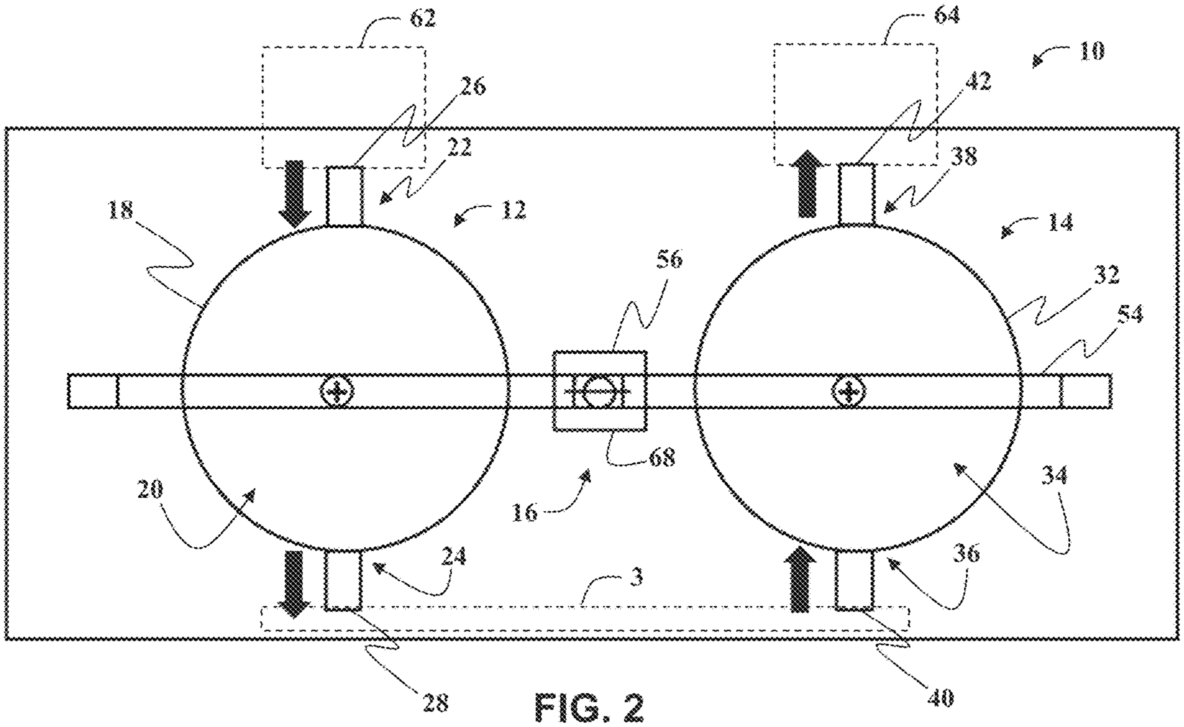
FIG. 2 is a top schematic view of the respirator ventilator device shown in FIG. 1.
Figure 3:
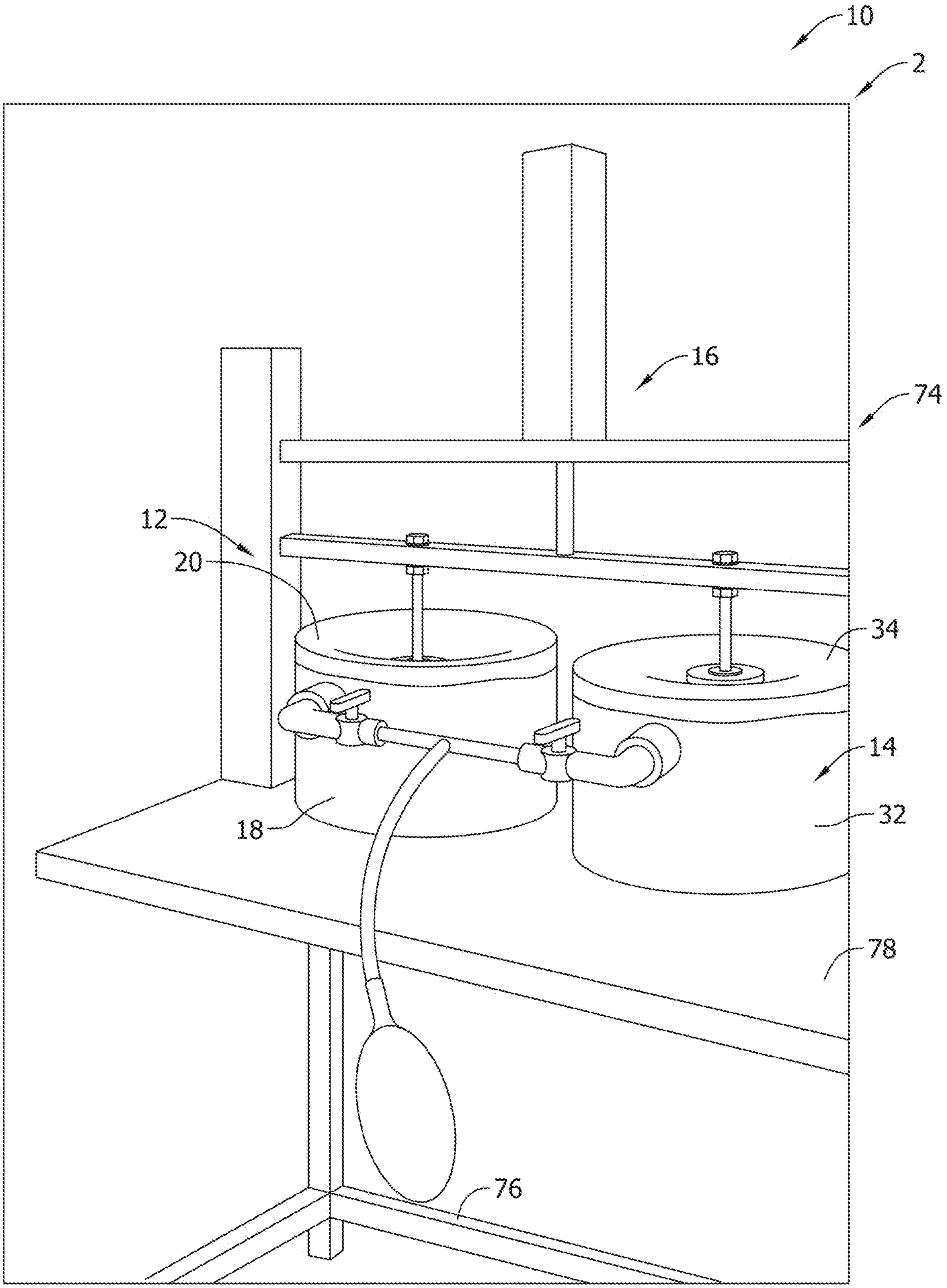
FIG. 3 is a perspective view of the respirator ventilator device, according to embodiments of the present invention.

With reference to the drawings and in operation, the present invention provides a respiratory ventilator device that includes a low-cost ventilator device for respiratory support for treatment of patients suffering from pneumonia and/or COVID-19, and non-COVID-19 patients suffering from other respiratory diseases. The respiratory ventilator system 10 provides respiratory support that replicates the human breathing mechanism for patients that require it, because of illnesses such as pneumonia, COVID-19 related or not, at low cost and with ease of fabrication.

The present invention solves the cost problem of known ventilators by providing a respiratory ventilator system that can be easily made in a metal workshop without specialized or complex machinery, equipment, and tooling, making feasible its immediate production. Additional advantages of the present invention include a respiratory ventilator system that replicates the natural mechanism of human respiration for both inhalation and exhalation, making it safe and reliable.

The specification utilizes medical terminology currently in use in the mechanical ventilation field, e.g., inspiration in place of inhalation, and expiration in place of exhalation; Tidal Volume or VT, referring to the volume of each inspiration, and Respiratory Rate RR, to the number of respirations (operating cycles of the device) per minute. Also there are Peak Pressure PPK referring to the maximum pressure in the patient's airway during inspiration, Plateau Pressure PPL, referring to the patient's airway pressure during the pause between inspiration end and expiration beginning, and Post Expiratory End Pressure PEEP, the patient's airway pressure during the pause between expiration end and inspiration beginning.

Referring to FIGS. 1-18, in the illustrated embodiment, the present invention includes a respiratory ventilator device 2 including a respiratory ventilator system 10 that is coupled to a patient respiratory circuit 3 for providing air to a patient's lungs to facilitate breathing. The respiratory ventilator system 10 is mounted within a housing 4 and includes an inhaled air assembly 6, an exhaled air assembly 7, and a control system 8. The inhaled air assembly 6 is coupled to the patient respiratory circuit 3 and is configured to channel a volume of inhalation air to a patient's lungs via the patient respiratory circuit 3 to assist in patient inhalation. The volume of inhalation air may be drawn from ambient air and/or may be supplemented with oxygen. The exhaled air assembly 7 coupled to the patient respiratory circuit 3 and is configured to remove air from the patent's lungs via the patient respiratory circuit 3 to assist in a patient exhalation. The control system 8 is operatively coupled to the inhaled air assembly 6 and the exhaled air assembly 7 and configured to operate the respiratory ventilator device in an inhalation mode and an exhalation mode.

In some embodiments, the respiratory ventilator system 10 includes the inhaled air assembly 6 including an injector diaphragm assembly 12, the exhaled air assembly 7 including an extractor diaphragm assembly 14, and the control system 8 including a reciprocating assembly 16 coupled to the injector diaphragm assembly 12 and the extractor diaphragm assembly 14.

The injector diaphragm assembly 12 includes an injector diaphragm housing 18 and an air injection diaphragm 20 coupled to a top portion of the injector diaphragm housing 18. For example, the injector diaphragm housing 18 may include a cylindrical tank (or any other shaped tank such as conical, spherical, pyramidal, etc.) having an open top end. The air injection diaphragm 20 may include a flexible silicone rubber assembly (or any other suitable flexible material) that is attached to the open top end of the cylindrical tank of the injector diaphragm housing 18 to define an adjustable volume within the injector diaphragm housing 18. The injector diaphragm housing 18 includes an injector inlet port 22, an injector outlet port 24, an injector check valve assembly 26 coupled to the injector inlet port 22, and an injector solenoid valve assembly 28 coupled to the injector outlet port 24. The injector diaphragm housing 18 may also include an injector volume reduction member 30 positioned within an interior of the injector diaphragm housing 18 for reducing the internal volume of injector diaphragm housing 18. For example, the injector volume reduction member 30 may include a conic metal piece located inside the cylindrical tank of the injector diaphragm housing 18 for reducing the internal volume of injector cylindrical tank. The injector volume reduction member 30 may also have any suitable shape such as, for example, conical, spherical, pyramidal, etc., and be formed of any suitable material such as metal, plastic, or any other suitable material.

The extractor diaphragm assembly 14 includes an extractor diaphragm housing 32 and an air extraction diaphragm 34 coupled to a top portion of the extractor diaphragm housing 32. For example, the extractor diaphragm housing 32 may include a cylindrical tank (or any other shaped tank such as conical, spherical, pyramidal, etc.) having an open top end. The air extraction diaphragm 34 may include a flexible silicone rubber assembly (or any other suitable flexible material) that is attached to the open top end of the cylindrical tank of the extractor diaphragm housing 32 to define an adjustable volume within the extractor diaphragm housing 32. The air extraction diaphragm 34 is attached to the open top end of the cylindrical tank to define an adjustable volume within the extractor diaphragm housing 32. The extractor diaphragm housing 32 includes an extractor inlet port 36, an extractor outlet port 38, an extractor solenoid valve assembly 40 coupled to the extractor inlet port 36, and an extractor check valve assembly 42 coupled the extractor outlet port 38. The extractor diaphragm housing 32 may also include an extractor volume reduction member 44 positioned within an interior of the extractor diaphragm housing 32 for reducing the internal volume of extractor diaphragm housing 32. For example, the extractor volume reduction member 44 may include a conic metal piece located inside the cylindrical tank of the extractor diaphragm housing 32 for reducing the internal volume of extractor cylindrical tank. The extractor volume reduction member 44 may also have any suitable shape such as, for example, conical, spherical, pyramidal, etc., and be formed of any suitable material such as metal, plastic, or any other suitable material.

The reciprocating assembly 16 coupled to the injector diaphragm assembly 12 and the extractor diaphragm assembly 14 and is configured to operate the respiratory ventilator system 10 between an inhalation mode 46 during which air is injected into a patient's lungs, and an exhalation mode 48 during which air is extracted from the patient's lungs.

The reciprocating assembly 16 includes an air injection diaphragm pusher 50, an air extraction diaphragm pusher 52, a support bar 54 coupled to the air injection diaphragm pusher 50 and the air extraction diaphragm pusher 52, and a reciprocating motor assembly 56 coupled to the support bar 54. The reciprocating motor assembly 56 includes a cylinder rod 58 coupled to the support bar 54 and a motor 60 coupled to the cylinder rod 58 to cause the cylinder rod 58 and support bar 54 to move in a reciprocating motion. The motor 60 may include, for example, a pneumatic cylinder, and/or any other reciprocating mechanism suitable to implement a reciprocating motion.

The air injection diaphragm pusher 50 is coupled to the support bar 54 and the air injection diaphragm 20 such that movement of the support bar 54 causes movement of the air injection diaphragm 20. Similarly, the air extraction diaphragm pusher 52 is coupled to the support bar 54 and the air extraction diaphragm 34 such that movement of the support bar 54 causes movement of the air extraction diaphragm 34.

Figure 14:
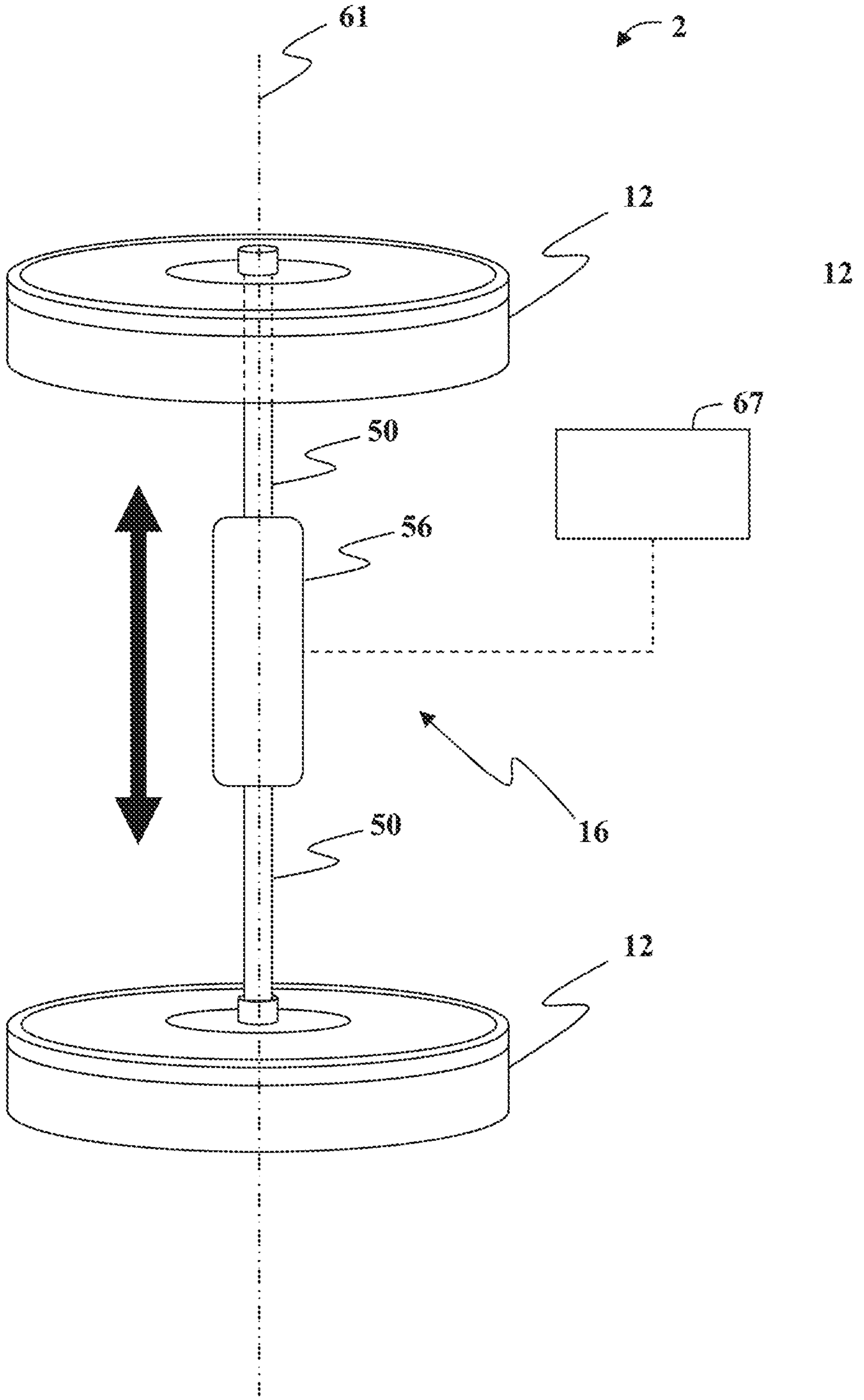
FIGS. 14 and 15 are schematic views of the respirator ventilator device.

In some embodiments, as shown in FIGS. 5-14, the injector diaphragm assembly 12 and the extractor diaphragm assembly 14 may be orientated along a centerline axis 61 with the air injection diaphragm pusher 50 coaxially aligned with the air extraction diaphragm pusher 52 along a centerline axis 61. In some embodiments, the injector diaphragm assembly 12 and the extractor diaphragm assembly 14 may be orientated in a vertically stacked arrangement as shown in FIG. 14. In other embodiments, the injector diaphragm assembly 12 and the extractor diaphragm assembly 14 may be orientated in a horizontal arrangement.

In some embodiments, an inlet air supply connector assembly 62 may be coupled to the air injector inlet port 22 for providing a supply of air to the injector diaphragm assembly 12. In other embodiments, the injector inlet port 22 may be configured to channel ambient air to the injector diaphragm assembly 12. In addition, in some embodiments, an exhaust air outlet connector assembly 64 may be coupled to the extractor outlet port 38 for receiving and/or collecting a volume of air being exhausted from the extractor diaphragm assembly 14. For example, the exhaust air outlet connector assembly 64 may include an air filtration system for filtering the air exhausted from the extractor diaphragm assembly 14. A patient respiratory circuit 3 is coupled to the injector outlet port 24 and the extractor inlet port 36 for channeling air from the injector diaphragm assembly 12 to the patient's lungs and for channeling air from the patient's lungs to the extractor diaphragm assembly 14.

The respiratory ventilator system 10 also includes the control system 8 including a controller 67 for operating the respiratory ventilator system 10. The controller 67 is operatively coupled to a micro switch assembly 68 that is coupled to the solenoid valve assemblies 28, 40 and the reciprocating motor assembly 56. The micro switch assembly 68 includes a micro switch 70 and a vertically adjustable micro switch support 72 coupled to the micro switch 70 for adjusting a vertical position of the micro switch 70. For example, in the illustrated embodiment, the micro switch 70 is positioned to allow the support bar 54 to periodically contact the micro switch 70 as the support bar 54 is moved through a reciprocating motion. The function of the micro switch assembly 68 may also be performed by other type of switches such as magnetic or proximity switches.

The respiratory ventilator system 10 may also include the housing 4 including a support assembly 74 for supporting the injector diaphragm assembly 12, an extractor diaphragm assembly 14, and/or the reciprocating assembly 16 from a ground surface. The support assembly 74 may include a base frame 76 mounted on the ground surface, a support plate 78 coupled to the base frame 76, and a cylinder support frame 80 mounted to the support plate 78 and/or the base frame 76. The cylinder support frame 80 is coupled to the reciprocating assembly 16 for supporting the reciprocating assembly 16 from the support plate 78 and/or the base frame 76. The injector diaphragm assembly 12 and the extractor diaphragm assembly 14 may each be mounted onto the support plate 78 to support the injector diaphragm assembly 12 and the extractor diaphragm assembly 14 from the base frame 76. The vertically adjustable micro switch support 72 is mounted onto the support plate 78 and positioned to allow the support bar 54 to periodically contact the micro switch 70 as the support bar 54 is moved through a reciprocating motion.

The components of the respiratory ventilator system 10 may be built with materials suitable for sanitary and medical purposes, such as stainless steel, including pneumatic fittings. The support structure of the device (support assembly, frame, base, etc.) can be built of carbon steel with a suitable finish such as powder coat paint. The diaphragms 20, 34 may be made, for example, with silicone rubber.

During operation, the respiratory ventilator system 10 operates to cyclically inject fresh air to the patient lungs and alternatively extracting spent air from patient lungs, using fittings and tubing commonly used in hospital patient respiratory circuits, that can be connected to the respiratory ventilator system 10.

For example, during the inhalation mode 46, at cycle's beginning diaphragms 20, 34 are in a first position 100. The motor 60, which is attached firmly to frame 74, pushes down the support bar 54 and cylinder rod 58, which in-turn, causes the diaphragm pushers 50, 52 to push downwards onto the air injection diaphragm 20 and the air extraction diaphragm 34 to reduce the internal volumes of the injector diaphragm housing 18 and the extractor diaphragm housing 32, respectively, and forcing air out of the respiratory ventilator system 10.

During the inhalation mode 46, air contained within the injector diaphragm assembly 12 flows through the injector solenoid valve assembly 28 (which may also be replaced by a check valve) to the patient respiratory circuit 3, which with appropriate tubing and fittings, will be injected into patient's lungs. At the same time, the extractor diaphragm assembly 14 pushes spent air, previously extracted from the patient's lungs in a previous cycle, out through extractor check valve assembly 42 to the exhaust air outlet connector assembly 64. This spent air can be filtered and or sterilized downstream in a suitable machine for that purpose to render it harmless.

When the cylinder rod 58 of the motor 60 reaches a bottom position 102, the respiratory ventilator system 10 transitions to operate in the exhalation mode 48. For example, as the cylinder rod 58 reaches the bottom position 102, the support bar 54 activates the micro switch 70, which reverses the direction of the pneumatic cylinder movement, causing the cylinder rod 58, support bar 54, diaphragm pushers 50, 52, and the air injection diaphragm 20 and the air extraction diaphragm 34 to move upwards.

As the air injection diaphragm 20 moves in an upward direction, the injector diaphragm assembly 12 draws in fresh air from the inlet air supply connector assembly 62 through the injector check valve assembly 26. Simultaneously, as the air extraction diaphragm 34 moves in the upward direction, the extractor diaphragm assembly 14 will suction spent air from patient's lungs through extractor solenoid valve assembly 40.

Fresh air can be treated upstream prior to entering injector check valve assembly 26 with suitable devices and/or machines and connections for filtering, humidifying, oxygenating, etc. When the motor 60 reaches the top position 100, the cycle repeats itself, injecting fresh air and alternatively extracting spent air from patient lungs.

Device air volume displaced per cycle may be adjusted either by reducing the distance separating bar 54 from diaphragms 20, 34 at the pushers 50, 52 and/or adjusting the height of micro switch assembly 68 which will reduce the length of the cylinder stroke, and consequently the volume displaced in each cycle.

Cycle time can be modified to desired frequency per minute (respiratory rate) manually by adjusting the cylinder exhaust valves and cylinder pressure, or by installing an electronic/electric timer on the machine, or by means of a computer controlled proportional flow valve.

As was mentioned above, in either fresh air suction through injector check valve assembly 26 and or spent air expulsion through extractor check valve assembly 42 required accessories such as UV air sterilizers, humidifiers, heaters, filters, can be installed.

In the illustrated embodiment, the inhaled air assembly 6 is coupled to the patient respiratory circuit 3 and is configured to channel a volume of inhalation air to a patient's lungs via the patient respiratory circuit 3 to assist in patient inhalation. The exhaled air assembly 7 is coupled to the patient respiratory circuit 3 and is configured to remove air from the patent's lungs via the patient respiratory circuit 3 to assist in a patient exhalation. In some embodiments, the patient respiratory circuit 3 may include a patient face mask 110, a y-junction assembly 112 coupled to a ventilator pressure and flow sensor 113 and to the face mask 110 or to an endotracheal tubing, an inspiratory tubing 114, and an expiratory tubing 116. The inspiratory tubing 114 is coupled between the inhaled air assembly 6 and the y-junction assembly 112 to provide air to the face mask 110 or endotracheal tubing. The expiratory tubing 116 is coupled between the y-junction assembly 112 and the exhaled air assembly 7 for channeling exhaled air from the face mask 110 to the exhaled air assembly 7. In some embodiments, the patient respiratory circuit 3 may include a humidifier assembly 118 coupled to the inhaled air assembly 6 and the inspiratory tubing 114 for regulating the humidity of the inhalation air.

The control system 8 is operatively coupled to the inhaled air assembly 6 and the exhaled air assembly 7 and is configured to operate the respiratory ventilator device 2 in an inhalation mode 46 and an exhalation mode 48. The control system 8 operates the inhaled air assembly 6 to generate a positive air pressure to channel the volume of inhalation air to the patient's lungs during the inhalation mode 46 and operates the exhaled air assembly 7 to generate a negative air pressure to remove the air from the patent's lungs during the exhalation mode 48.

Figure 15:
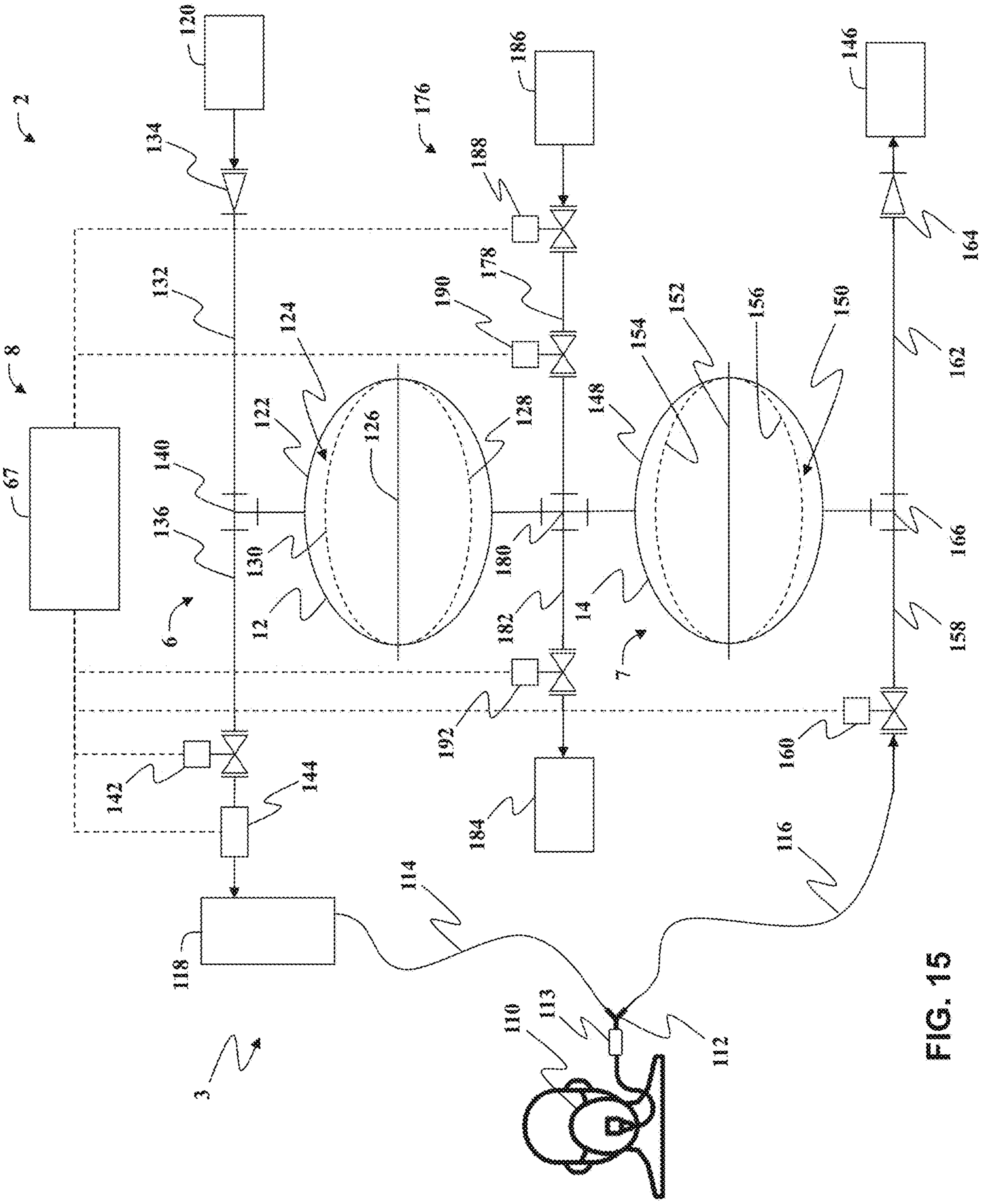
Figure 16:
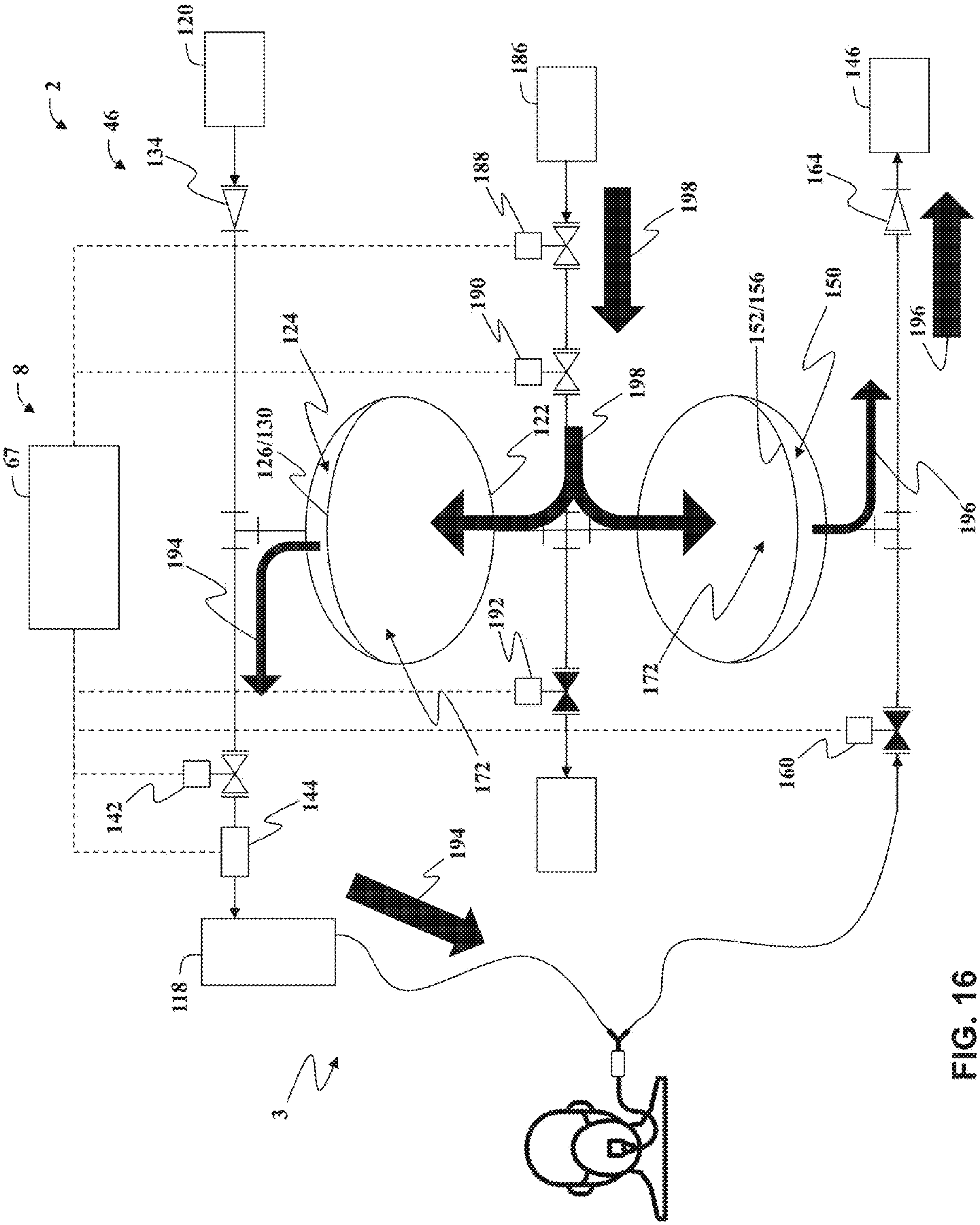
FIG. 16 is a schematic view of the respirator ventilator device operating in an inhalation mode.

Referring to FIG. 15, in some embodiments, the inhaled air assembly 6 includes an injector diaphragm assembly 12 that is coupled between the patient respiratory circuit 3 and a supply of inhalation air 120 for receiving the volume of inhalation air from the supply of inhalation air 120 and delivering the volume of inhalation air to the patient respiratory circuit 3. The injector diaphragm assembly 12 includes an injector diaphragm housing 122 that includes an inner surface defining an inhalation air chamber 124 and an inhalation diaphragm 126 that is coupled to the injector diaphragm housing 122 to enclose the inhalation air chamber 124. The inhalation diaphragm 126 is moveable between a first inhalation position 128 and a second inhalation position 130 to adjust a volume of the inhalation air chamber 124. The inhalation air chamber 124 defines a first volume of the inhalation air chamber 124 with the inhalation diaphragm 126 in the first inhalation position 128 (shown in FIG. 17) and defines a second volume of the inhalation air chamber 124 with the inhalation diaphragm 126 in the second inhalation position 130 (shown in FIG. 16). The first volume of the inhalation air chamber 124 is greater than the second volume of the inhalation air chamber 124.

The injector diaphragm assembly 12 also includes an inhalation inlet line 132 that is coupled to the injector diaphragm housing 122 and is configured to receive the volume of inhalation air from the supply of inhalation air 120 into the injector diaphragm housing 122. An inhalation check valve assembly 134 is coupled to the inhalation inlet line 132 and is positioned between the supply of inhalation air 120 and the injector diaphragm housing 122. An inhalation outlet line 136 is coupled to the injector diaphragm housing 122 and is configured to deliver the volume of inhalation air to the patient respiratory circuit 3 from the injector diaphragm housing 122. An inhalation tee fitting 140 is coupled between the inhalation inlet line 132, the inhalation outlet line 136, and the injector diaphragm housing 122 such that the inhalation inlet line 132, the inhalation outlet line 136, and the injector diaphragm housing 122 are in fluid communication.

An inhalation solenoid valve (or check valve) assembly 142 is coupled to the inhalation outlet line 136 and positioned between injector diaphragm housing 122 and the patient respiratory circuit 3 to selectively channel fresh air (oxygenated or not) from the injector diaphragm housing 122 to the patient respiratory circuit 3. A sensor assembly 144 may be coupled between the inhalation solenoid valve assembly 142 and the patient respiratory circuit 3 for sensing an air pressure, air flow, and/or oxygen % content being delivered to patient respiratory circuit 3. A sensor assembly may also be installed between y-junction and face mask or endotracheal tubing, which has the additional advantage of taking measurements closer to the patient.

The exhaled air assembly 7 includes an extractor diaphragm assembly 14 that is coupled between the patient respiratory circuit 3 and an exhaust air collection system 146 for receiving a volume of exhaled air from the patient respiratory circuit 3 and delivering the volume of exhaled air to the exhaust air collection system 146. In some embodiments, the exhaust air collection system 146 may include an air filtration system. The extractor diaphragm assembly 14 includes an extractor diaphragm housing 148 that includes an inner surface defining an exhalation air chamber 150. An exhalation diaphragm 152 is coupled to the extractor diaphragm housing 148 to enclose the exhalation air chamber 150. The exhalation diaphragm 152 is moveable between a first exhalation position 154 and a second exhalation position 156 to adjust a volume of the exhalation air chamber.

The exhalation air chamber 150 defines a first volume of the exhalation air chamber 150 with the exhalation diaphragm 152 in the first exhalation position 154 and defines a second volume of the exhalation air chamber 150 with the exhalation diaphragm 152 in the second exhalation position 156. The first volume of the exhalation air chamber 150 is greater than the second volume of the exhalation air chamber 150.

The exhaled air assembly 7 also includes exhalation inlet line 158, an exhalation solenoid valve assembly 160, an exhalation outlet line 162, and an exhalation check valve assembly 164. The exhalation inlet line 158 is coupled to the extractor diaphragm housing 148 and is configured to receive the volume of exhaled air from the patient respiratory circuit 3 into the extractor diaphragm housing 148. The exhalation solenoid valve assembly 160 is coupled to the exhalation inlet line 158 and is configured to selectively channel exhaled air from the patient respiratory circuit 3 into the extractor diaphragm housing 148. The exhalation outlet line 162 is coupled to the extractor diaphragm housing 148 and is configured to deliver the volume of exhaled air to the exhaust air collection system 146. The exhalation check valve assembly 164 is coupled between the exhalation outlet line 162 and the exhaust air collection system 146. An exhalation tee fitting 166 is coupled between the exhalation inlet line 158, the exhalation outlet line 162, and the extractor diaphragm housing 148 such that the exhalation inlet line 158, the exhalation outlet line 162, and the extractor diaphragm housing 148 are in fluid communication.

In the illustrated embodiment, the control system 8 includes a controller 67 that includes a processor that is coupled to a memory device that stores an operating program that includes computer executable instructions that, when executed by the processor, cause the processor to operate the respiratory ventilator system 10 in the inhalation mode 46 and the exhalation mode 48. In some embodiments, the control system 8 may also include a display assembly 168 that is mounted to the housing 4 and coupled to the processor. The processor is programmed to display computer generated graphic user interface on the display assembly 168 to enable a user to operate the respiratory ventilator system 10 and/or display various status icons and messages related to the operation of the respiratory ventilator system 10. The control system 8 may also include a control panel 170 having one or more input buttons that enables the user to operate the respiratory ventilator system 10.

Figure 4A:
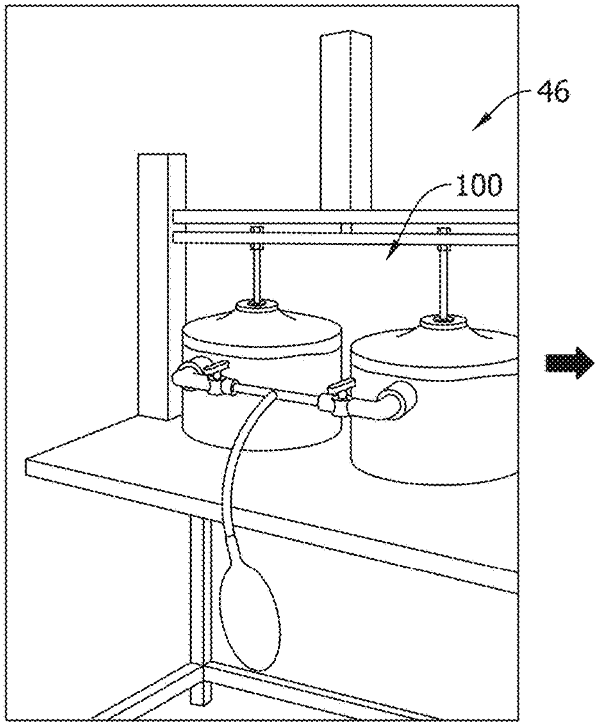
FIGS. 4A-4D are perspective views of the respirator ventilator device during operation.
Figure 4B:
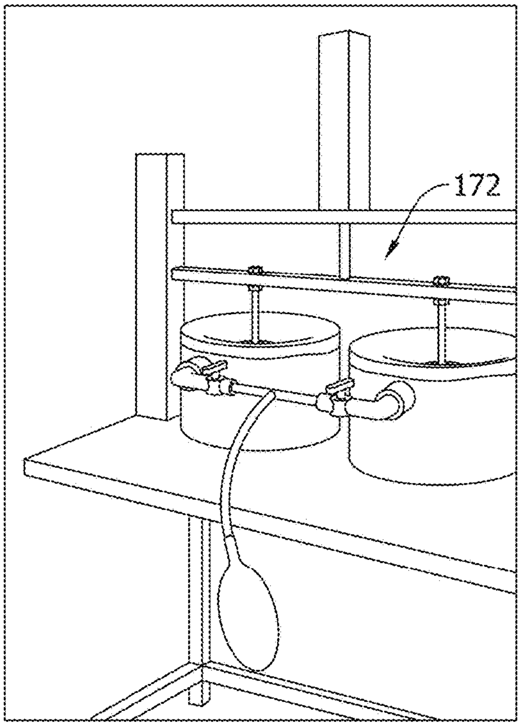
Figure 4C:
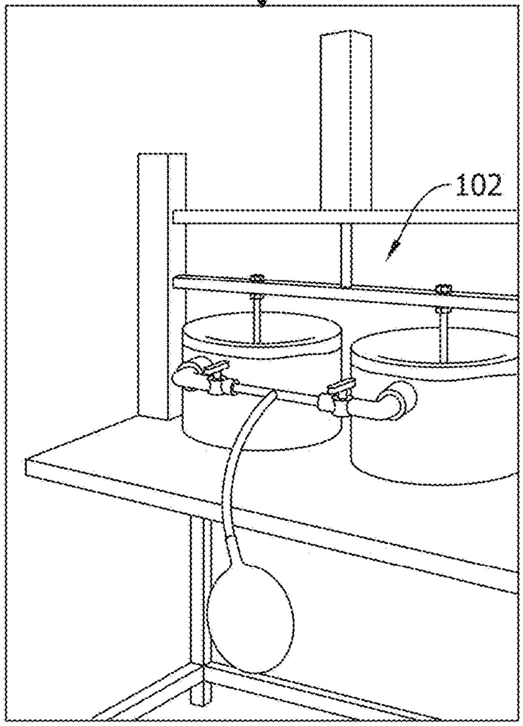
Figure 4D:
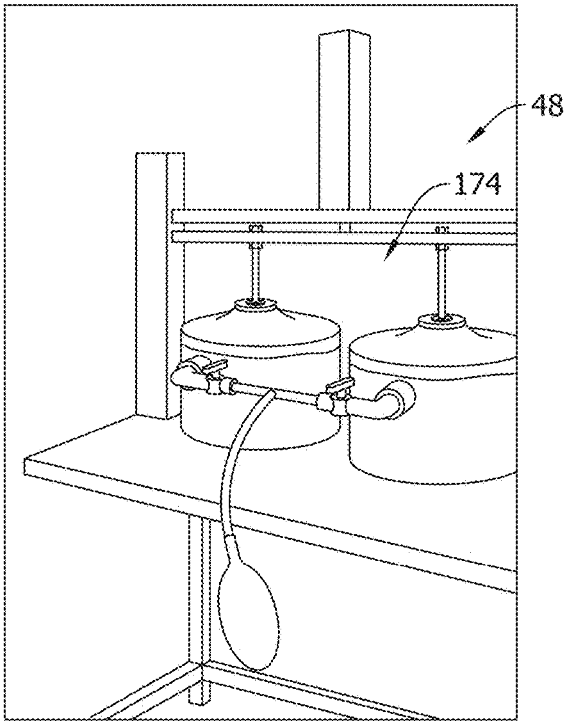
Figure 5:
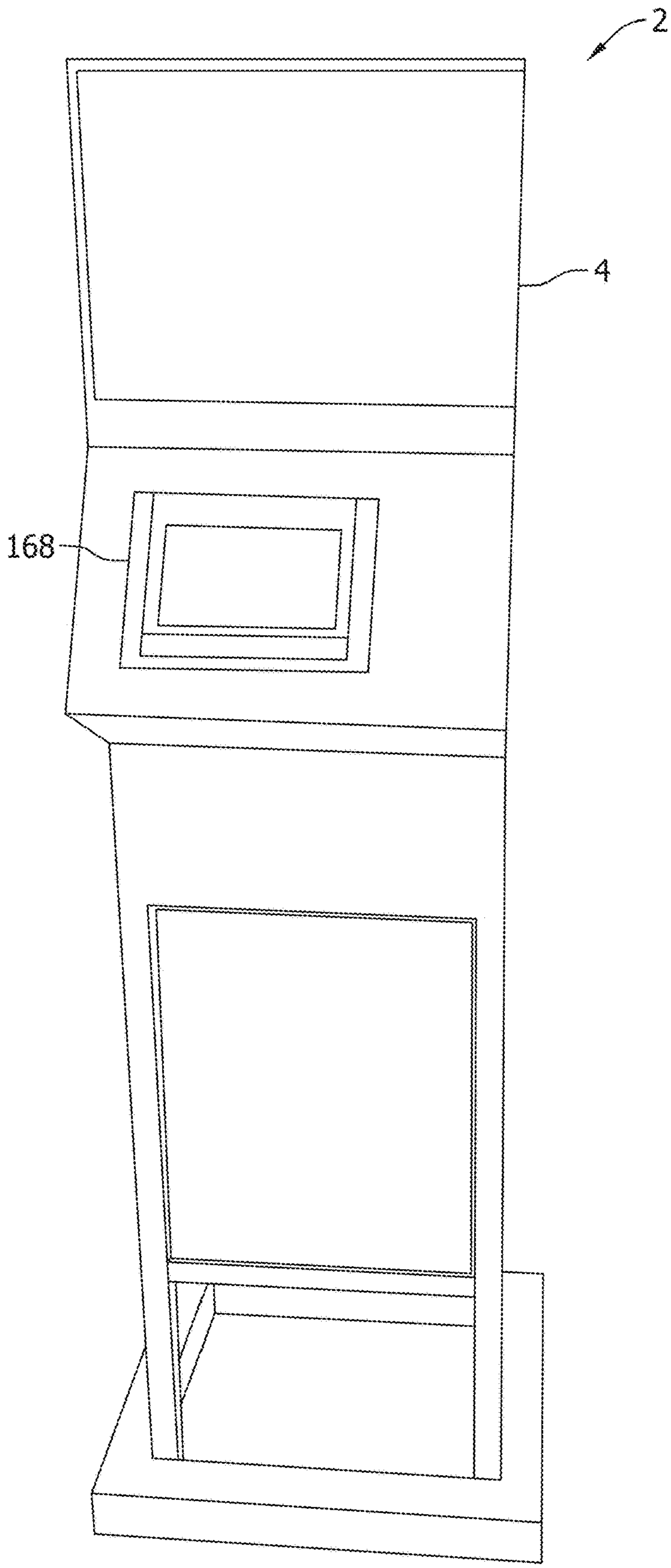
FIGS. 5-13 are perspective views of the respirator ventilator device, according to embodiments of the present invention.
Figure 6:
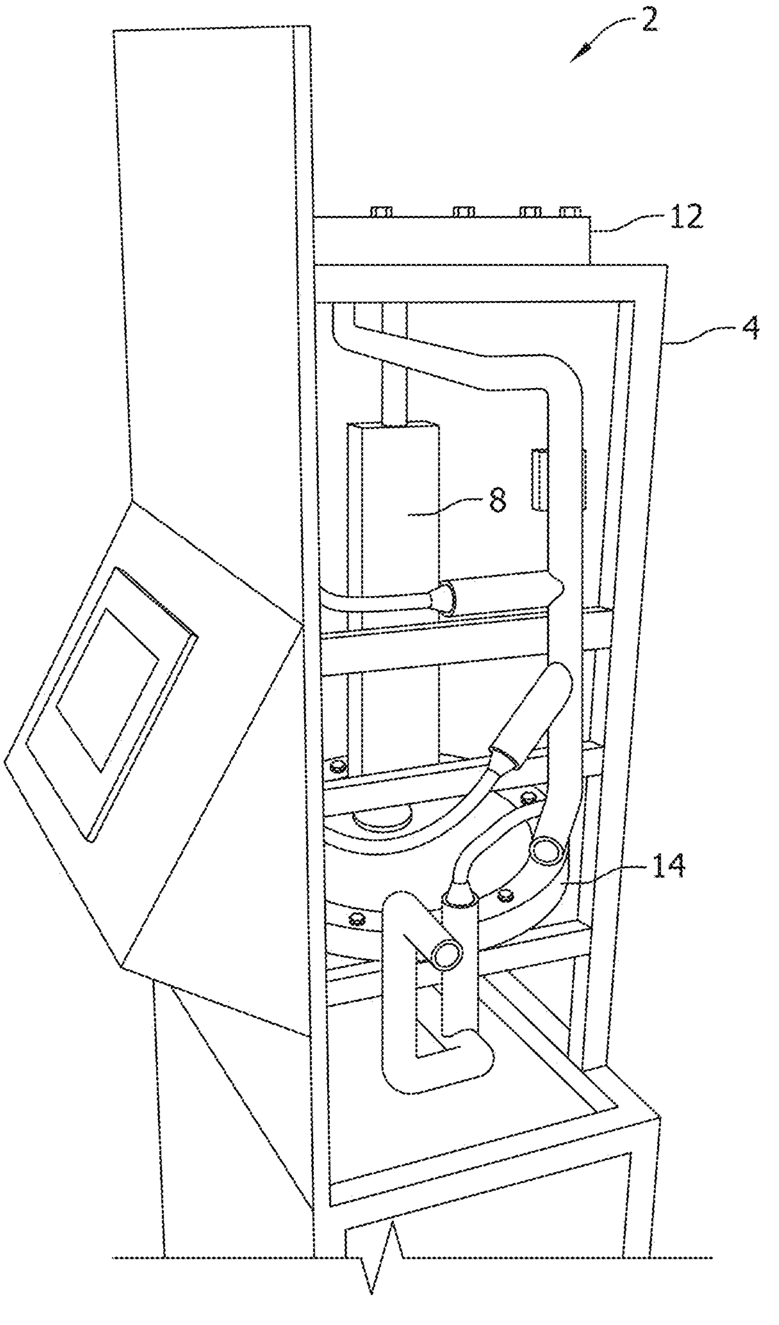
Figure 7:
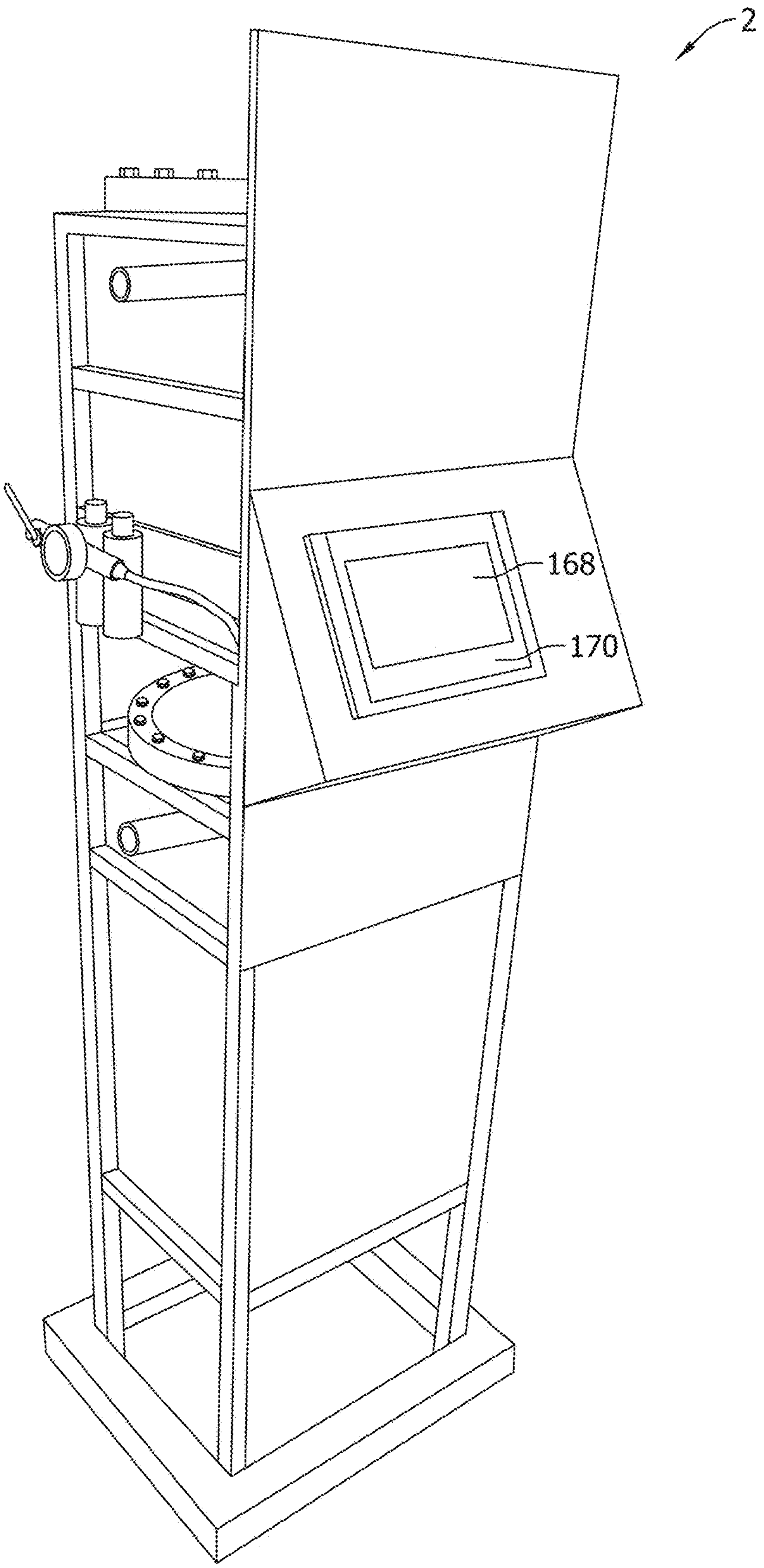
Figure 8:
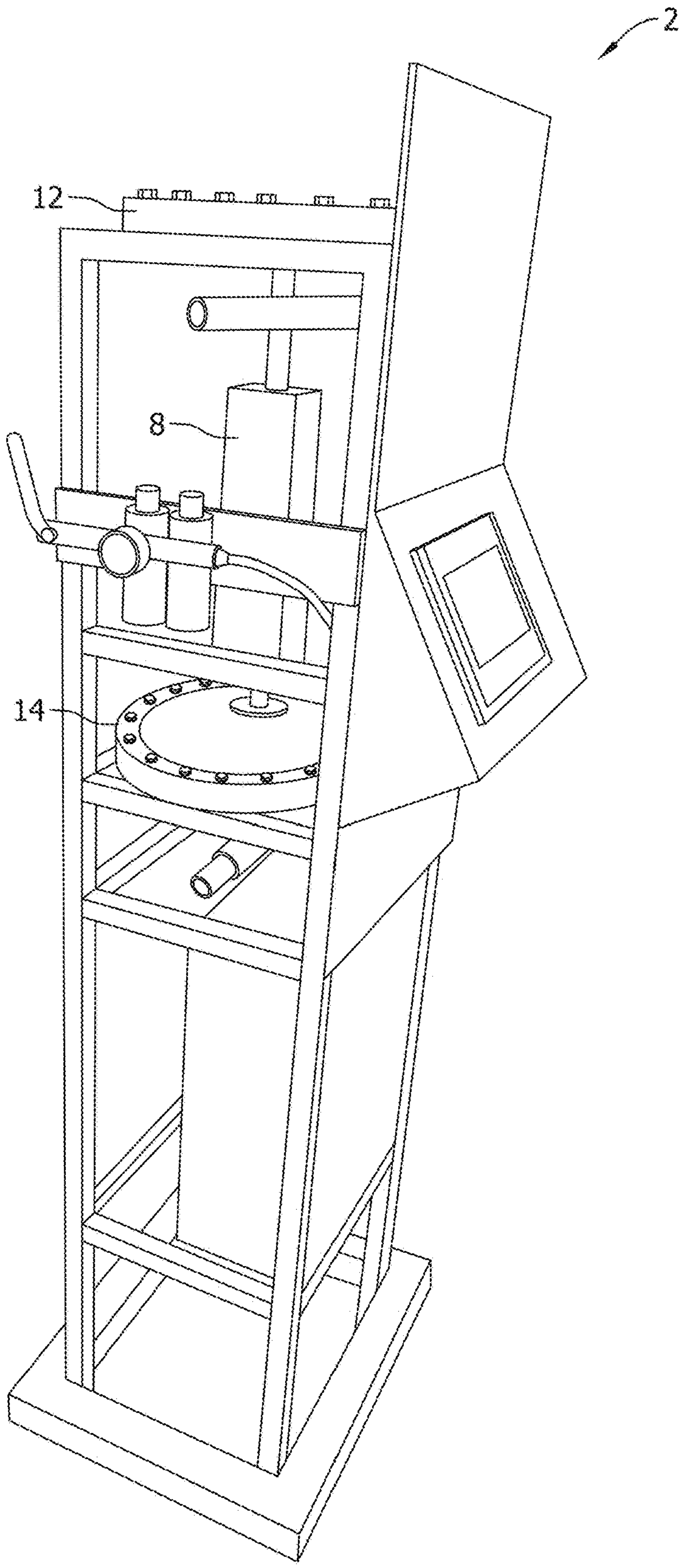
Figure 9:
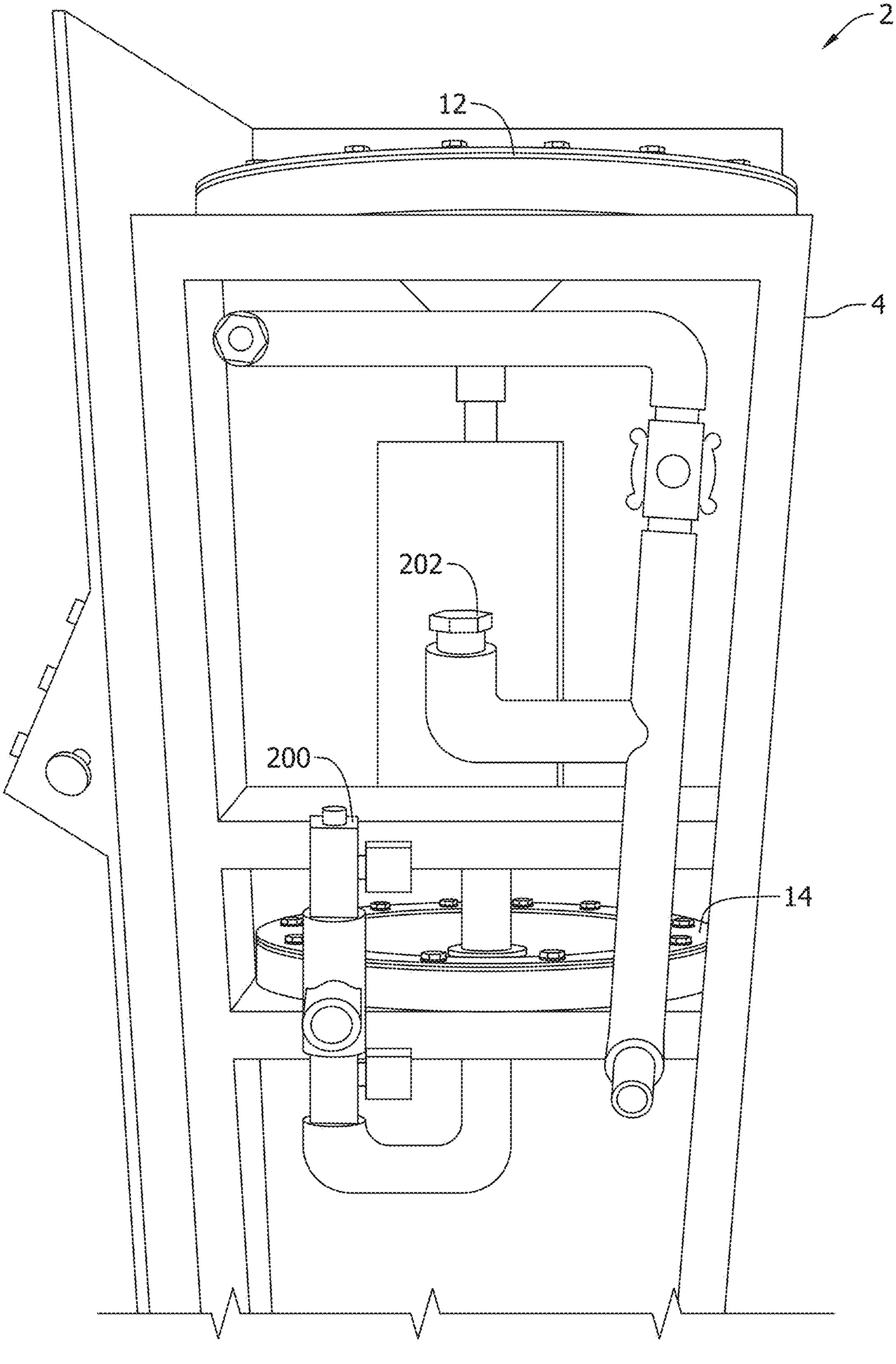
Figure 10:
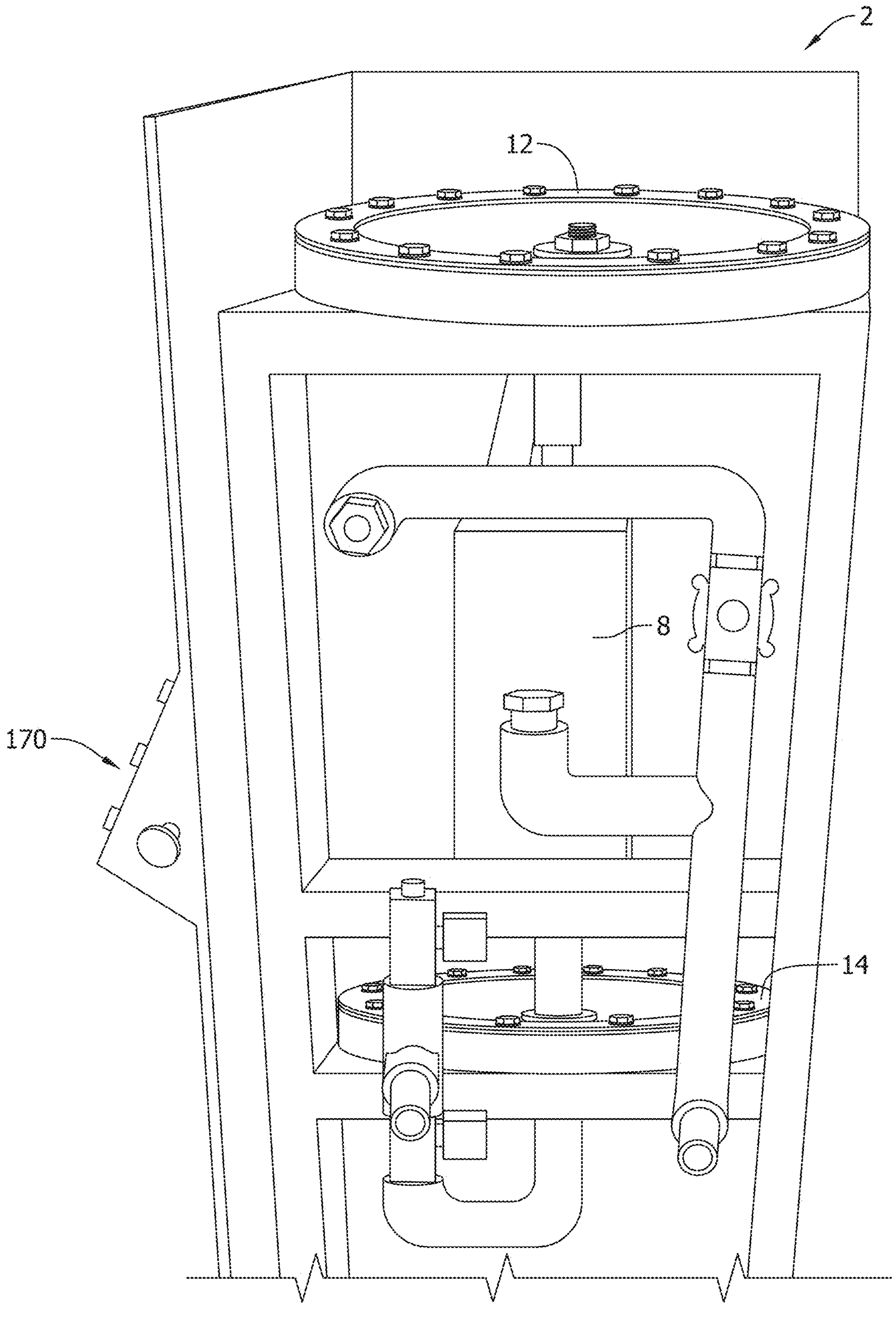
Figure 11:
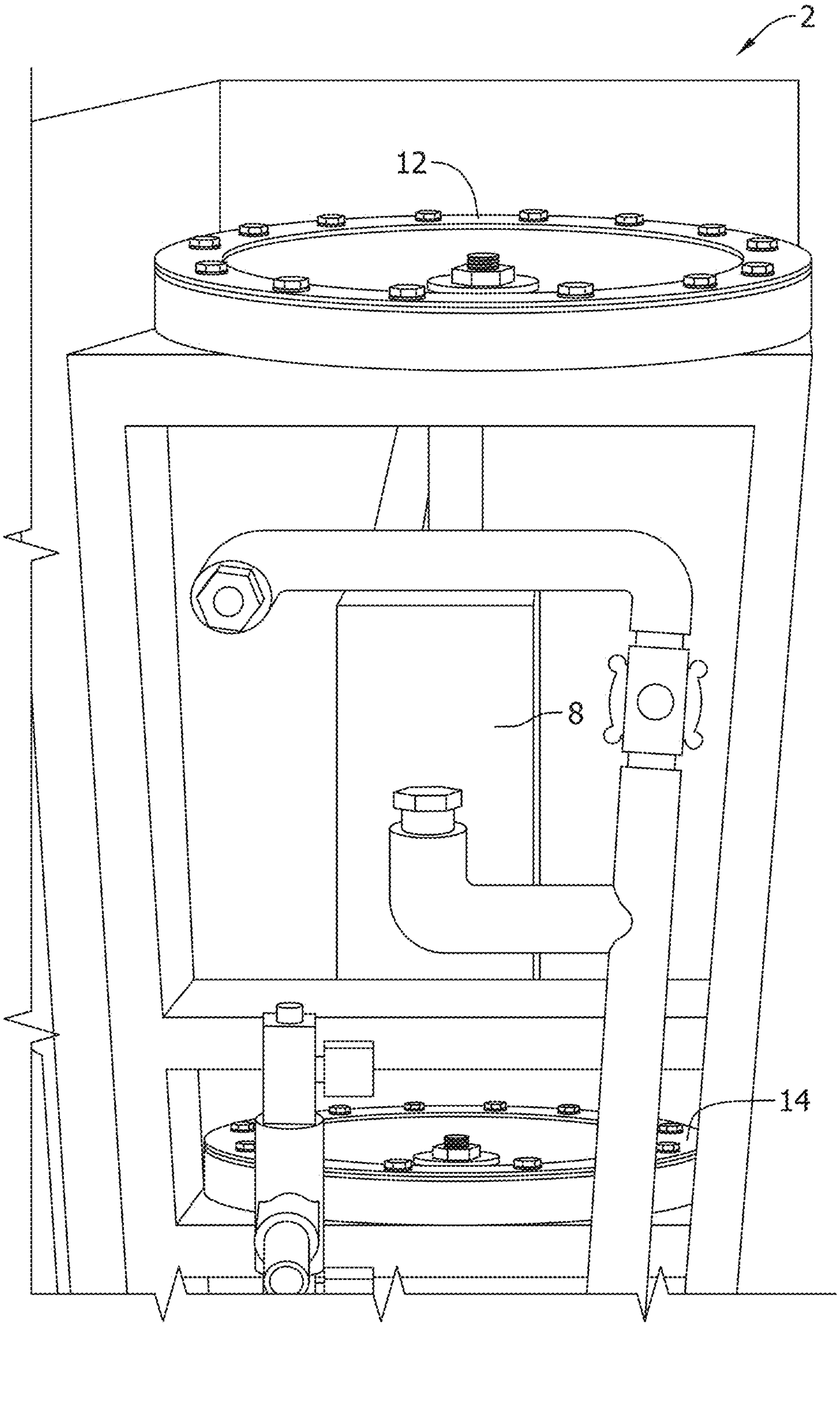
Figure 12:
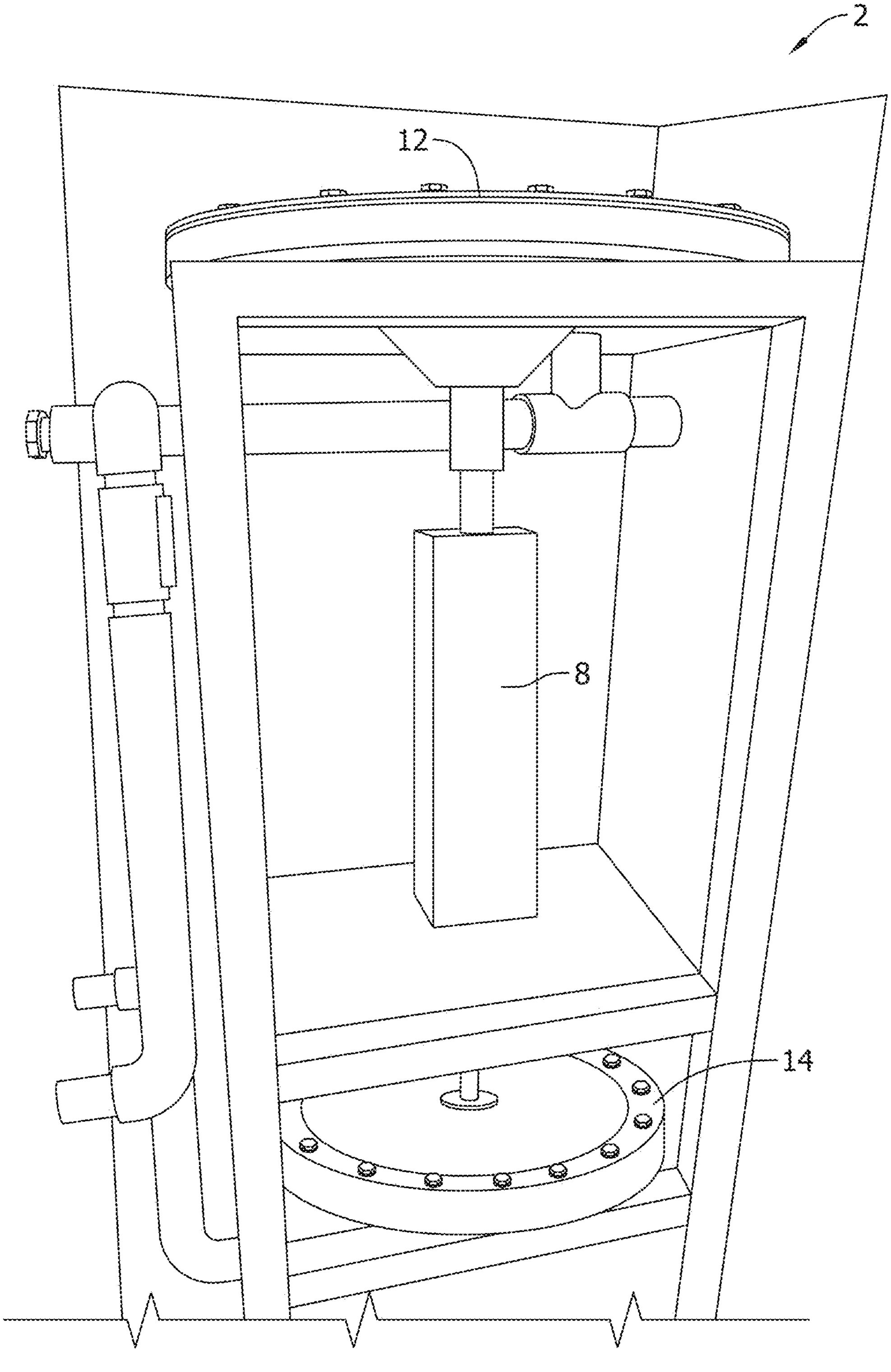
Figure 13:
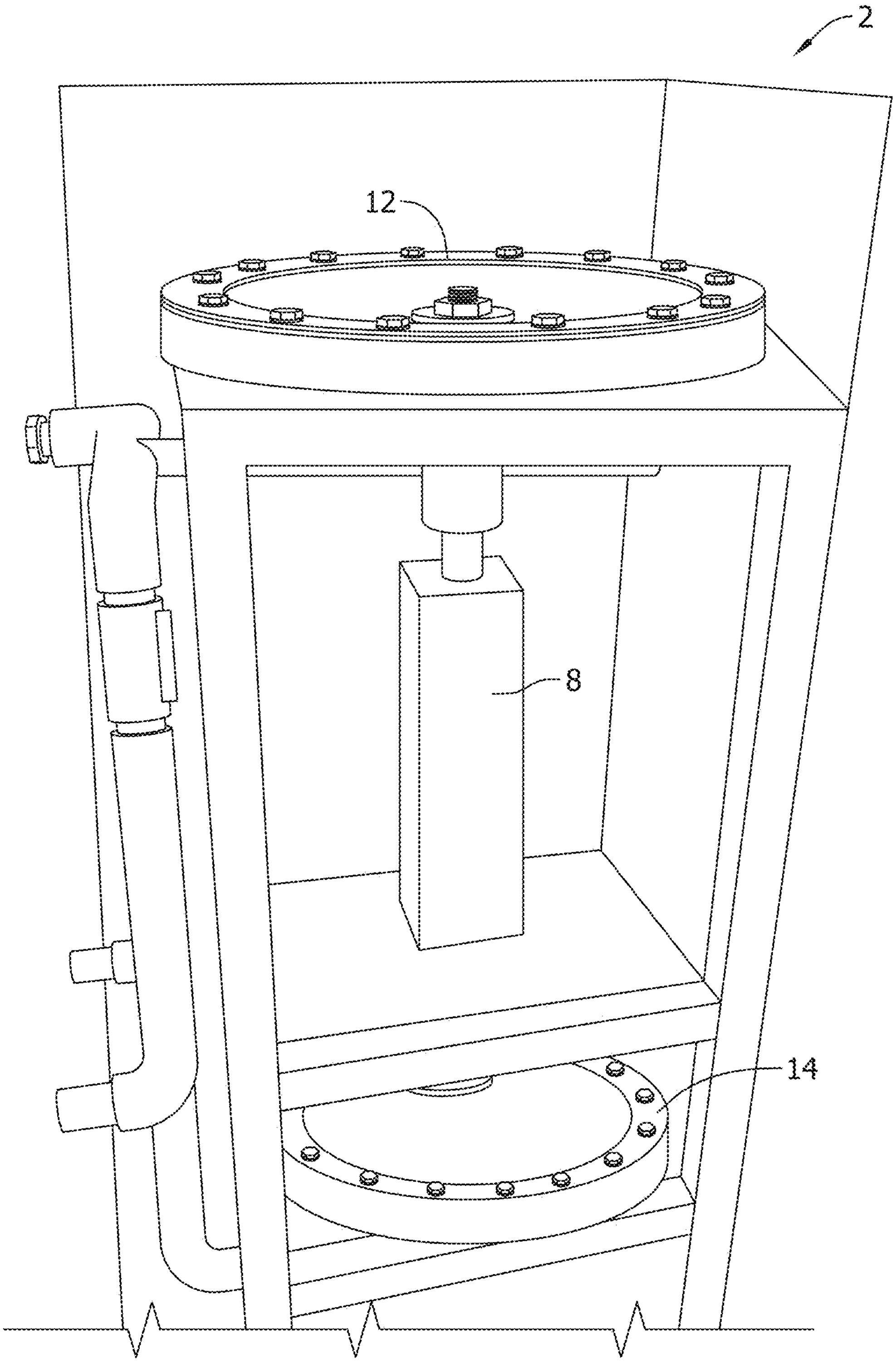
Figure 17:
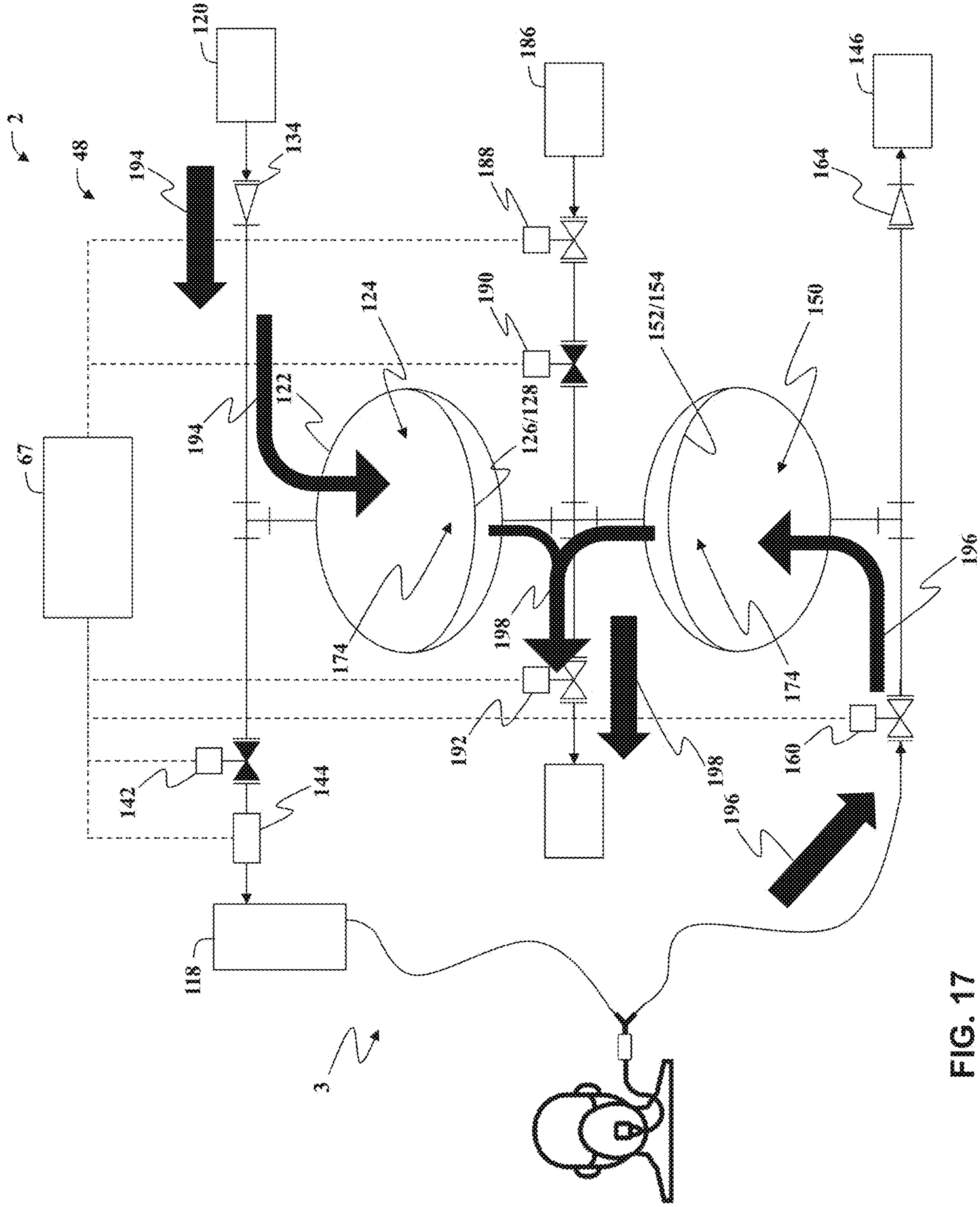
FIG. 17 is a schematic view of the respirator ventilator device operating in an exhalation mode.
Figure 18:
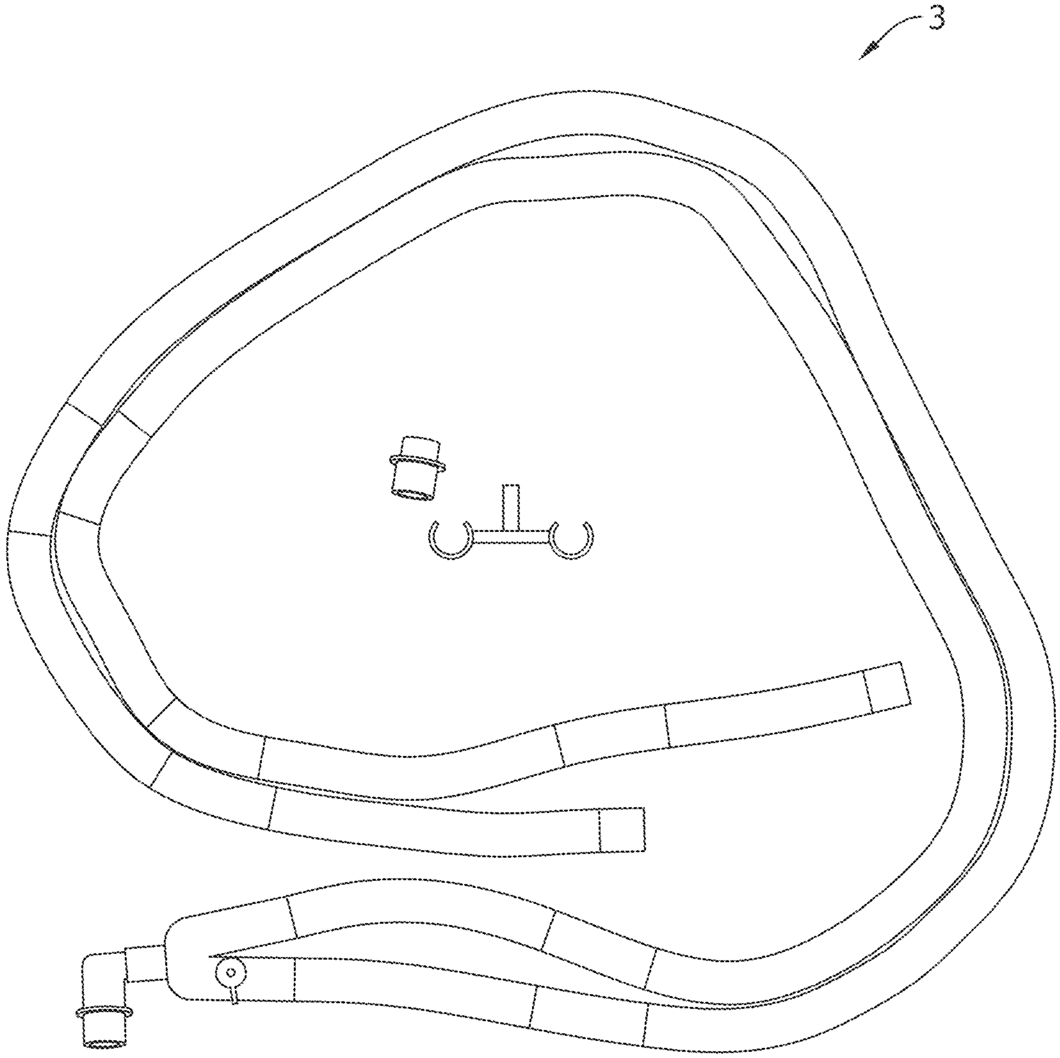
FIG. 18 is a partial perspective view of a patient respiratory circuit that may be used with the respirator ventilator device.

The control system 8 is configured to operate the inhaled air assembly 6 and the exhaled air assembly 7 in an operating cycle that includes a compression phase 172 (shown in FIGS. 4B and 16) and an expansion phase 174 (shown in FIGS. 4D and 17).

The control system 8 is configured to operate the inhaled air assembly 6 in the compression phase 172 to move the inhalation diaphragm 126 from the first inhalation position 128 to the second inhalation position 130 to reduce the volume of the inhalation air chamber 124 to deliver the volume of inhalation air to the patient respiratory circuit 3. In the compression phase 172, the control system 8 simultaneously operates the exhaled air assembly 7 to move the exhalation diaphragm 152 from the first exhalation position 154 to the second exhalation position 156 to reduce the volume of the exhalation air chamber 150 and deliver the volume of exhaled air to the exhaust air collection system 146.

The control system 8 is also configured to operate the inhaled air assembly 6 in the expansion phase 174 to move the inhalation diaphragm 126 from the second inhalation position 130 to the first inhalation position 128 to increase the volume of the inhalation air chamber 124 to receive the volume of inhalation air from the supply of inhalation air 120. The control system 8 also simultaneously operates the exhaled air assembly 7 in the expansion phase 174 to move the exhalation diaphragm 152 from the second exhalation position 156 to the first exhalation position 154 to increase the volume of the exhalation air chamber 150 to remove the air from the patent's lungs.

In some embodiments, the control system 8 includes the reciprocating assembly 16 coupled to the inhaled air assembly 6 and the exhaled air assembly 7 for operating the inhaled air assembly 6 and the exhaled air assembly 7 through the compression phase 172 and the expansion phase 174.

Referring to FIG. 15, in some embodiments, the control system 8 includes a pneumatic compressed air assembly 176 that is coupled to the inhaled air assembly 6 and the exhaled air assembly 7 for operating the inhaled air assembly 6 and the exhaled air assembly 7 through the compression phase 172 and the expansion phase 174. The pneumatic compressed air assembly 176 includes a compressed air inlet line 178 that is coupled to the inhaled air assembly 6 for channeling compressed air to the inhaled air assembly 6 to move the inhalation diaphragm 126 between the first and second inhalation positions 128, 130. The compressed air inlet line 178 is also coupled to the exhaled air assembly 7 for channeling compressed air to the exhaled air assembly 7 to move the exhalation diaphragm 152 between the first and second exhalation positions 154, 156. The pneumatic compressed air assembly 176 includes a cross fitting 180 coupled to the compressed air inlet line 178 and to the inhaled and exhaled air assemblies 6, 7 for channeling compressed air to the inhaled and exhaled air assemblies 6, 7. The pneumatic compressed air assembly 176 may also include a compressed air outlet line 182 coupled between the cross fitting 180 and a compressed air outlet 184 for channeling compressed air from the inhaled and exhaled air assemblies 6, 7. The pneumatic compressed air assembly 176 also includes the compressed air inlet line 178 coupled to a source of compressed air 186, a proportional solenoid valve 188 that is coupled to the compressed air inlet line 178, an inlet solenoid valve 190 that is coupled between the proportional solenoid valve 188 and the cross fitting 180, and outlet solenoid valve 192 that is coupled between the cross fitting 180 and the compressed air outlet 184.

During the inhalation mode 46, the control system 8 operates the inhaled air assembly 6 and the exhaled air assembly 7 in the compression phase 172 to operate the inhaled air assembly 6 to generate a positive air pressure to channel the volume of inhalation air 194 from the injector diaphragm assembly 12 to the patient's lungs and operate the exhaled air assembly 7 to channel the exhaled air 196 stored in the extractor diaphragm assembly 14 to the exhaust air collection system 146. In the compression phase 172, the control system 8 operates the pneumatic compressed air assembly 176 with the proportional solenoid valve 188 and the inlet solenoid valve 190 in an open position to channel compressed air 198 to the inhaled and exhaled air assemblies 6, 7, and with the outlet solenoid valve 192 operated in a closed position to prevent compressed air being channeled through the compressed air outlet 184. The control system 8 also operates the inhalation solenoid valve assembly 142 in an open position to channel oxygenated air from the injector diaphragm housing 122 to the patient respiratory circuit 3, and operates the exhalation solenoid valve assembly 160 in a closed position to prevent air from entering the exhaled air assembly 7.

During the exhalation mode 48, the control system 8 operates the inhaled air assembly 6 and the exhaled air assembly 7 in the expansion phase 174 to operate the exhaled air assembly 7 to generate a negative air pressure to remove exhaled air 196 from the patent's lungs and into the extractor diaphragm assembly 14 and operate the inhaled air assembly 6 to receive the volume of inhalation air 194 from the supply of inhalation air 120 through inhalation check valve assembly 134 and into the injector diaphragm assembly 12.

In the expansion phase 174, the control system 8 operates the pneumatic compressed air assembly 176 with the inlet solenoid valve 190 in a closed or partially closed position to limit compressed air channeled into the inhaled and exhaled air assemblies 6, 7, and with the outlet solenoid valve 192 operated in an open position to channel compressed air from the inhaled and exhaled air assemblies 6, 7 to the compressed air outlet 184. The control system 8 also operates the inhalation solenoid valve assembly 142 in a closed position to limit oxygenated air from being channeled to the patient respiratory circuit 3, and operates the exhalation solenoid valve assembly 160 in an open position to generate a negative air pressure to remove exhaled air 196 from the patent's lungs and into the extractor diaphragm assembly 14.

The respiratory ventilator device 2 provides a low cost ventilator device for respiratory support for Pneumonia, COVID-19, and non-COVID-19 patients with the purpose of the device to give respiratory support for patients in ICU. The medical parameters can be configured and controlled with the control system through standard electric/electronic equipment, such as PLC's, relay's, counters, timers, etc.

During the inhalation mode 46, compressed air is supplied through the compressed air inlet line 178 and flows through the proportional solenoid valve 188 which controls the flow rate, and through the inlet solenoid valve 190 which controls time with the outlet solenoid valve 192 closed. Afterwards, compressed air flows through the cross fitting 180 to a cavity below the inhalation diaphragm 126 and to a cavity above the exhalation diaphragm 152. This causes the diaphragms 126, 152 to expel air contained in the other side of each diaphragm 126, 152. On the inhalation diaphragm 126, air is expelled through a fitting and inhalation solenoid valve assembly 142 is open, and sensor assembly 144 monitors air pressure and flowrate or oxygenated air delivered to the patient. At the same time, air from previous exhalation in lower cavity of exhalation diaphragm 152 is expelled through a fitting and through exhalation check valve assembly 164.

During exhalation mode, as the inhalation and exhalation diaphragms 126, 152 reach their top and bottom positions respectively, solenoid valves 142, 190 close and solenoid valves 160, 192, open permitting compressed air to escape through compressed air outlet 184 allowing diaphragms 126, 152 to return to their center positions, with diagram 126 sucking fresh air through inhalation check valve assembly 134, and diaphragm 152 discharging air from patient. In a case that more volume capacity is required, outlet 184 can be connected to a vacuum line so diaphragms 126, 152 will move beyond their middle position and draw more air—fresh for inhalation and spent from exhalation. In other embodiments, diaphragms 126, 152, may include a coil spring attached to their centers on one end, and attached to the inner center of housings 122 and 148, making them return beyond their respective center positions when solenoid valve 192 opens.

In some embodiments, the control system 8 may also include an automatic solenoid relief valve 200 (shown in FIG. 9) that is operated by the controller 67 to control excess pressure at different phases of respiratory cycle without affecting flow rate or volume. Automatic excess pressure may be reduced with a mechanical relief valve 202, with interchangeable seals precision calibrated for different pressures. The control system 8 may also include large pilot lights in two different colors to indicate if ventilator is operating in inhalation or exhalation, on display assembly 168 independent from screen, visible from several meters distance. The display assembly 168 may include a large emergency stop push button that instantaneously stops ventilator operation opening all inhalation and exhalation valves, thus allowing patient to breath from surrounding air, preventing patient choking. The control system 8 may include an instantaneous stop push button for interrupting operation in any point of respiratory cycle, and resuming instantaneously operation at stopping cycle point. This is very useful for ventilator operator for checking with more detail pressures and other parameters, and also for performing short recruitment maneuvers. The control system 8 may also include visible and audible alarms with mute mode for audible possible; measurement and displaying of spontaneous respirations percentage in ventilation modes that permit, along with mandatory, spontaneous respirations from patient, and Recruitment Maneuver easily configured and performed, with several safety features.

The diaphragms can be orientated vertically, horizontally, or offset with the following advantages: 1) Eccentric loads are avoided, simplifying mechanical design and increasing life of diaphragms and actuator, 2) The external dimensions of ventilator are greatly diminished; with diaphragms in tandem, double space is required perpendicularly to diaphragms axis; 3) In a vertical fashion, one on top of 2-rod actuator and the other in the bottom, ventilator occupies the same space or even a little less than ventilators currently in use; 4) If, during use, you want to get "spent" air from patient away from the room in which the ventilator is, it can be done but it is not necessary or usual practice; in most cases they discharge "spent" air into same room prior passage through a filter. In the design in which compressed air pushes the diaphragms, if you have available a vacuum line it would double ventilator capacity. This means that the ventilator could be smaller for a certain capacity than without a vacuum line. It is because without a vacuum line after inspiration, diaphragm returns to its central position, and with a vacuum line it would return all the way down to the opposite casket, in fact duplicating air volume displaced;

and 5) can arrange stacked diaphragms horizontally or vertically. This can also be achieved with the coil spring as described above.

Additional benefits of the respiratory ventilator system 10 include: 1) Ease of fabrication in a minimally equipped metal fabricating shop. 2) Fabrication can be initiated almost immediately because no special tooling is required. 3) Replicates the natural human breathing mechanism, both in inhalation and exhalation, which will surely prove to be of therapeutic benefit. 4) All necessary parts and equipment such as valves, switches, pneumatic cylinder, fittings, tubing, timers, adjustable automatic slide, etc. are low cost and manufactured massively, and many companies carry them in stock. 5) Simple design that facilitates maintenance or repair easily and with basic electricity and mechanics knowledge. 6) Respiratory volume and frequency easily adjustable. 7) Simultaneous and or parallel use of diaphragms or any other air injection/extraction mechanism for inhalation and exhalation. 8) Use of any kind of three dimensional figure both regular and or irregular—cylinder, cube, prism, cone, pyramid, etc. with a diaphragm attached to perform, simultaneously or not, inhalation and exhalation functions. 9) Use of any kind of elastic material, natural or synthetic, in any shape, simultaneously or alternatively for reproducing the natural mechanism of human breathing. 10) Minimum risk of supplying or extracting air with excessive pressure or vacuum to the patient.

The respiratory ventilator device 2 also provides reconfiguration or redesign of two-diaphragm pumps to work as previously described ventilator device with the placement of diaphragms on the same axle, vertical, horizontal and otherwise, and also in a tandem configuration. The respiratory ventilator device 2 may also use any air or fluid movement device (e.g. apparatus, machine other than diaphragms such as fans, turbines, bellows, pumps, etc.) to work in the same two movements sequence of operation of the ventilator device herein described: first movement, in injection inhalation-side, fresh air is moved, blown, and/or impulsed towards patient and simultaneously spent air, that is extracted from patient in previous movement, is expelled from device in extraction exhalation-side. In second movement, fresh air is suctioned, blown, and/or impulsed, injected into chamber on injection side, and simultaneously exhaled air from patient is suctioned, extracted, into chamber on extraction side.

The respiratory ventilator device 2 also provides 1) ease of fabrication; practically all components can be purchased from stock or easily made in a metal working shop with basic metal working equipment; 2) Inhalation and exhalation mechanisms are almost equal to human respiration mechanism; 3) No motors, fans, bellows or actuators; 4) No mechanisms to convert circular motion to reciprocating; 5) Minimum moving parts which makes it more reliable and durable; 6) Control equipment and components are of common use throughout the world in several industries, which makes it cheaper, reliable, and easily replaceable; and 7) simplicity which reduces downtime for repairs and maintenance.

In some embodiments, the present invention includes a respiratory ventilator device 2 that replicates the human breathing mechanism. The respiratory ventilator device 2 includes, (FIG. 19) but is not limited to, the inhaled air assembly 6, the exhaled air assembly 7, both having an air impelling mechanism based on two diaphragms 122, 148 encased each one in a casket semispherical housing-one being the injector diaphragm housing 122 and the second the extractor diaphragm housing 148 and a mechanical and electrical/electronic control system operatively coupled to the inspiration air system and the expiration air system. The respiratory ventilator device inspiration connector 204 can be connected to the inspiratory tubing 114 which is an external accessory to the device and not a part of the present invention- and configured to supply a Tidal Volume of inspiration air to a patient to provide continuous respiratory support in patients requiring it. The exhaled air inlet 206 is coupled to the expiratory tubing 116 and configured to assist in a patient expiration. The control system is configured to operate the respiratory ventilator system cyclically in 4 respiratory phases: 1) a post-expiratory pause phase, 2) an inspiration phase 3) a post-inspiratory pause phase and 4) an expiration phase. The control system operates the ventilator device so inspiration and expiration volumes, pressures, flow rates, respiratory frequencies, phase times and Oxygen content in breathing air can be configured and operated accordingly to the patient's therapeutic needs.

In another aspect of the present invention, a method of configuring mechanical and electrical/electronic components/parts for operating a respiratory ventilator device according to the modes, parameters and their values most utilized in mechanical ventilation therapy is provided.

In yet another aspect of respiratory ventilator device is its ease of manufacturing, due to the use of materials, components and parts widely available and used in industry all over the world; also because its design, configuration and parts don't require any special tooling or machinery so it can be manufactured immediately in large quantities in a standardly equipped sheet metal working shop.

Figure 19:
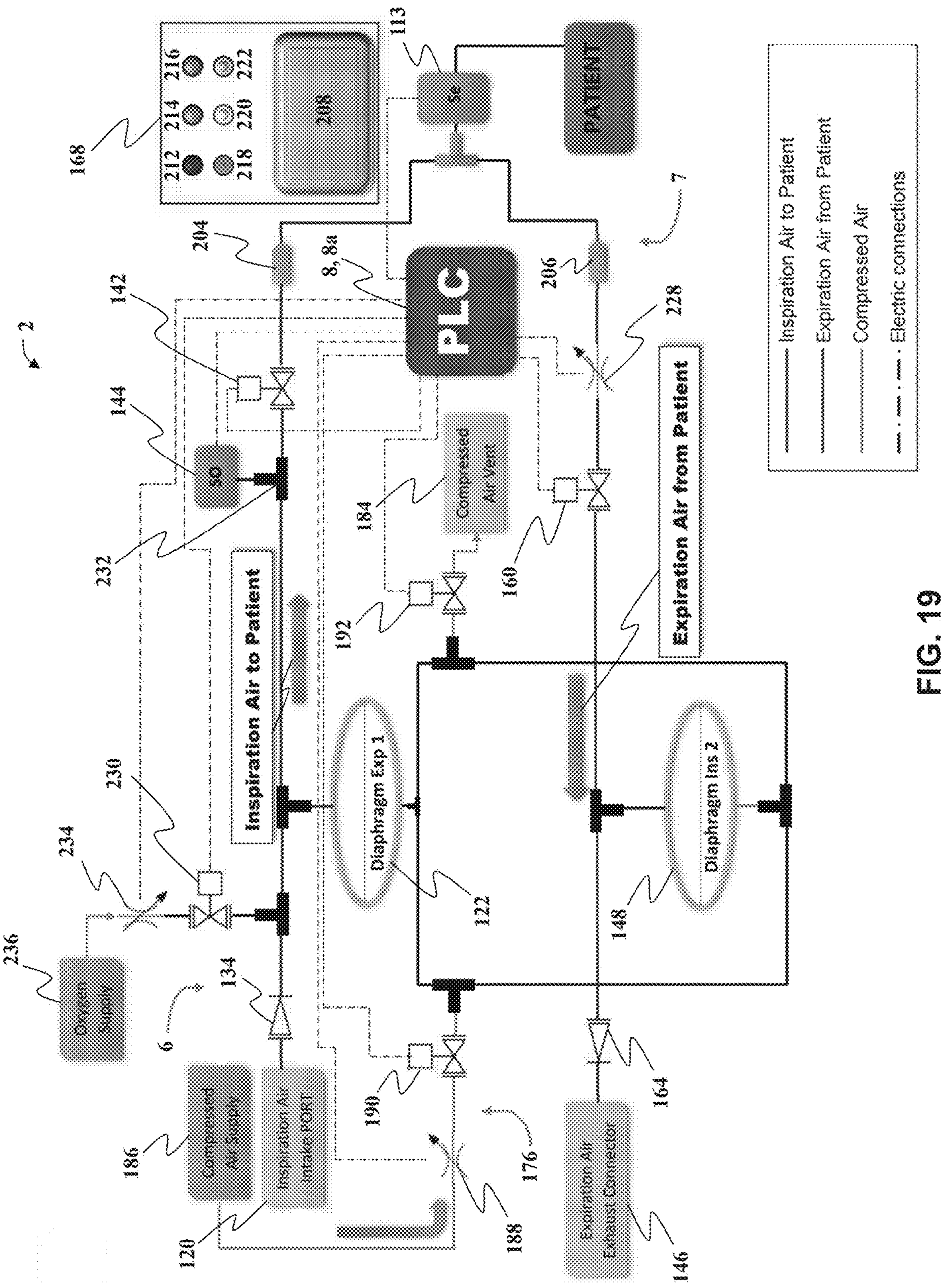
FIG. 19 is another schematic illustration of the respirator ventilator device, according to embodiments of the present invention.

FIG. 19 represents schematically the physical configuration of the mechanical and electric/electronic control system, which operates cyclically the ventilator in four phases of each cycle, being these: Phase 1, Post Expiratory End Pause; Phase 2, inspiratory Phase; Phase 3, Post Inspiratory Pause; Phase 4, Expiratory Phase.

FIGS. 37-39, 42, 45, 48, 51, and 53 are flow charts of methods 300, 400, 500, 600, 700, 800, 900, and 1000 illustrating the algorithms executed by the processor of controller 67 for operating the respiratory ventilator device 2. The methods include a plurality of steps. Each method step may be performed independently of, or in combination with, other method steps. Portions of the methods may be performed by any one of, or any combination of, the components of the control system 8.

The control system 8 includes a Programmable Logic Controller (PLC) 8*a*. PLC 8*a* is the CPU in charge of controlling the entire operation of the respiratory ventilator device 2, through which it receives and sends signals from sensors, switches, solenoid valves and valves that are in the respiratory ventilator device 2 and these signals are used through proprietary software to carry out the correct operation of the device.

In some embodiments, the display assembly 168 includes a touchscreen 208 that displays a plurality of graphical user interface (GUI) configuration screens 210 for use in setting operational parameters and displaying status indicators for operating the respiratory ventilator device 2. The display assembly 168 may also include an Alarm Pilot Light 212 indicating an alarm, an Expiration Pilot Light 214 indicating an expiration phase, an Inspiration Pilot Light 216 indicating an inspiration phase, a Hold Stop Push Button 218, a Stop Emergency 220, and a Buzzer 222. The PLC 8*a* subsequently sends signals to a touchscreen 208 for the operator to be able to visualize the operation. The touchscreen 208 will display all the parameters and ventilation modes, such as the PPK, PPL, PEEP pressures, Tidal Volume, times, Respiratory Rate, Inspiration/Expiration phase. The configuration is also carried out on touch screen. The Emergency Stop button 220 has the function of completely stopping the operation of the respiratory ventilator device 2 in case there is a fault or simply when the operator decides it is convenient to stop the respiratory ventilator device 2. The Push Button Stop 218 functions for carrying out a small instantaneous stop for visualizing parameters and performing recruitment maneuvers. The sensors 113, 144 transmit signals to the PLC 8*a* for operation and control through software. The sensor assembly 144 is used to measure FiO2 (Fraction Inspired by Oxygen), which measures the concentration of oxygen in breathed air-O2 mixture. The Flow & Pressure Sensor 113 measures flow rate and air way pressure.

In the illustrated embodiment, in method step 302, the processor of controller 67 displays configuration screens 210 on the touchscreen 208 including a tidal volume input button 224 and a time input button 226 (shown in FIGS. 21, 22, 40, and 41). The processor of controller 67 then receives a Tidal Volume value and/or a time value from an operator via the touchscreen 208 and establishes a tidal volume limit and/or a time limit for operation of the respiratory ventilator device 2.

In method step 304, the processor of controller 67 then operates the respiratory ventilator device 2 in a Phase 1 Post-Expiratory Pause. For example, in some embodiments, the processor of controller 67 may measure Post-Expiratory End Pressure (PEEP) via sensor 113 and determine if PEEP pressure is below the set minimum, The PLC 8*a* will partially close the Proportional Valve 228 (shown in FIG. 19) for the next Expiration in the amount required to increase PEEP pressure. The diaphragms 122, 148 are in a central/neutral position, and solenoid valves 190, 192, 160, 230, 142 are operated in closed position. The processor of controller 67 may operate the respiratory ventilator device 2 in the Phase 1 Post-Expiratory Pause for 100 milliseconds, in Assist/Control (A/C) 6000/RR milliseconds, and/or in Intermittent Mandatory Minute Volume Ventilation (IMMVV) and SPN specified by operator. If APC is activated, PLC 8*a* opens valve 228 in case PEEP exceeds its maximum until AWP is 1 cm below PEEP Max. The processor of controller 67 executes a Phase change at the end of Phase time, or when APW is below trigger pressure (TP).

For example, in Phase 1, both diaphragms 122, 148, are in center—rest—position. Solenoid valves 190, 192, 160, 230, 142 are in closed position. Sensor 113, with a response time of 1.8 milliseconds, measures airway pressure, known in the medical field as Post Expiratory End Pressure or PEEP, through a signal sent to PLC 8*a*; PLC 8*a* sends PEEP value to Touchscreen 208 to be displayed. The trigger for ending Phase 1 and initiating Phase 2 can be time, patient inspiration effort—sensed by sensor 113 as a drop in pressure—or both—either one can be first—; these conditions are specified by operator in the configuration screen (FIGS. 21-22, 40-41) of ventilation mode chosen by operator in Touchscreen 208.

In method step 306, the processor of controller 67 then operates the respiratory ventilator device 2 in a Phase 2 Inspiration Phase. In the Inspiration Phase, the processor of controller 67 operates valves 142 and 190 open and adjusts valve 188 in order to deliver the Tidal Volume specified by operator as measured by sensor 113. The processor of controller 67 also operates valves 142 and 190 close when a predefined and/or operator designated Time, Pressure, or Flow & Pressure are reached. The processor of controller 67 also operates Inspiration pilot light 216 on Ventilator front panel 168 to light up during this phase, indicating that inspiration is being carried out.

Figure 40:
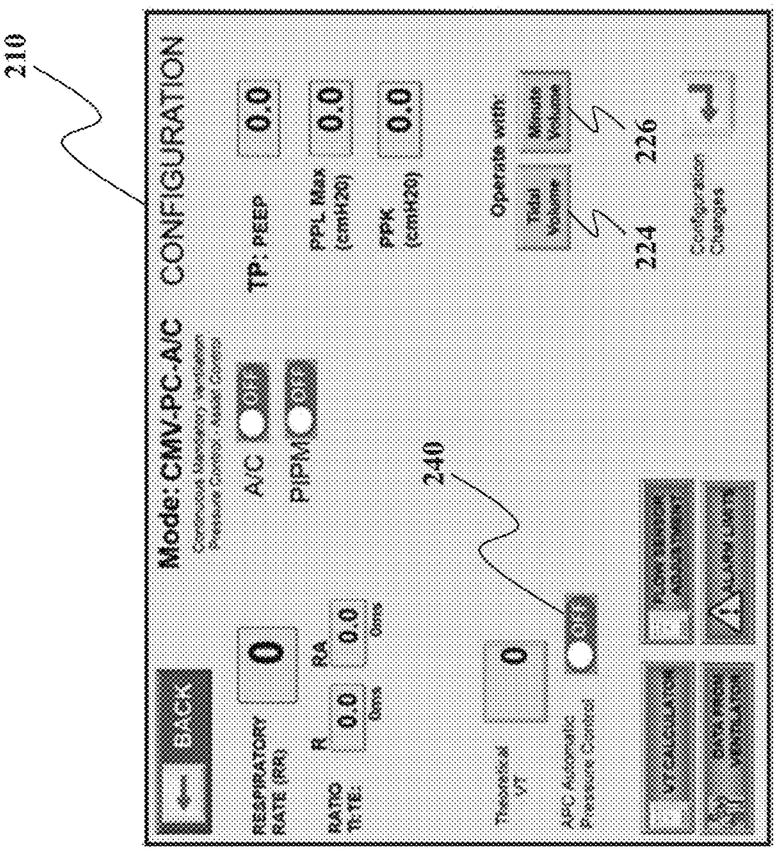
FIGS. 40-41 are schematic illustration of graphical user interfaces that may be displayed by the control system when executing the algorithms shown in FIGS. 37-39.
Figure 41:
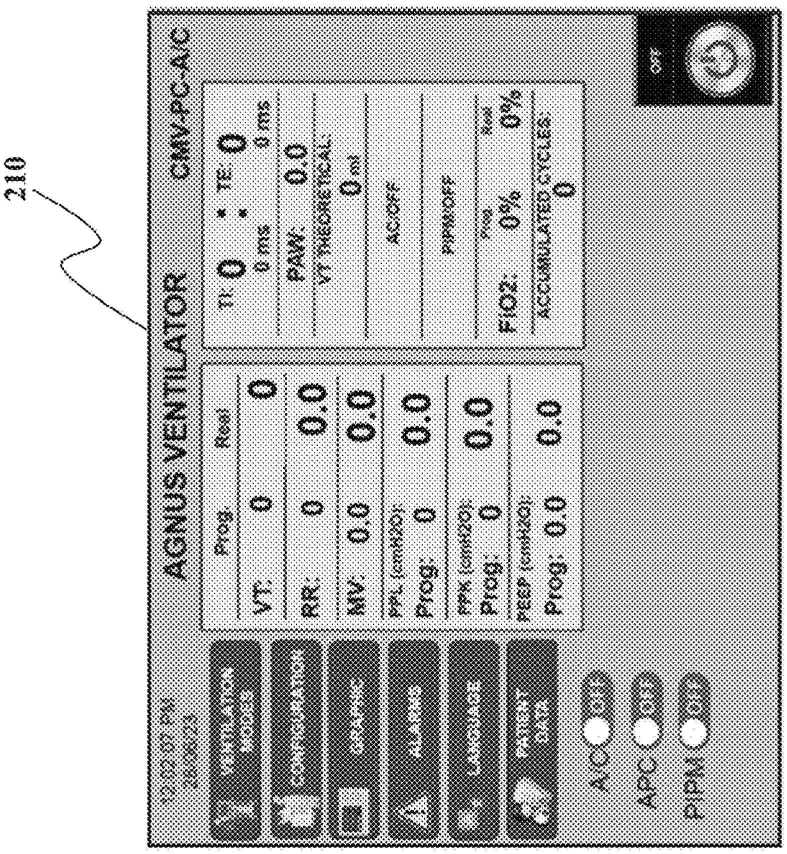
Figure 42:
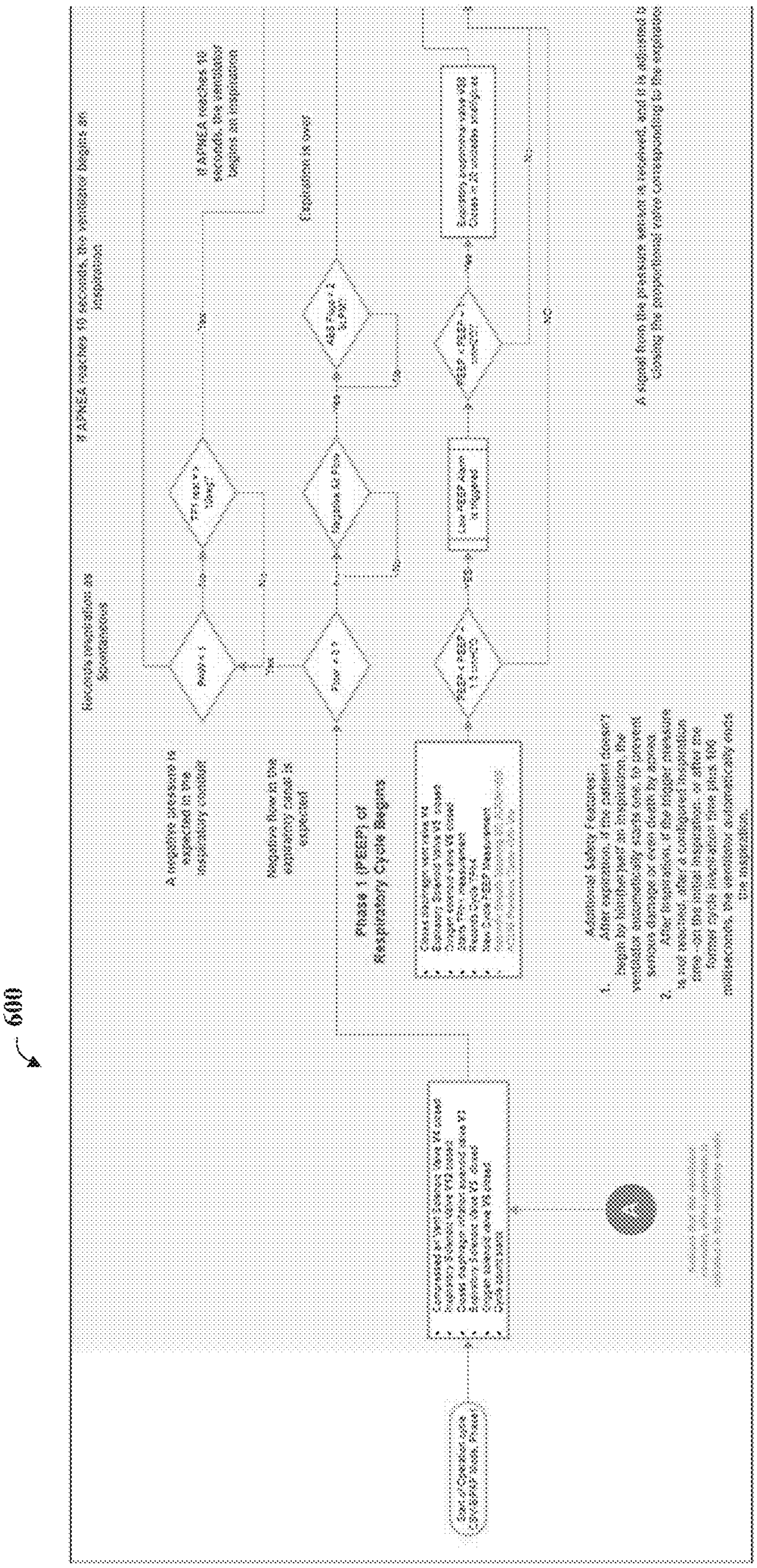
FIG. 42 is a flow chart illustrating another algorithm executed by the control system for use in operating the respirator ventilator device, according to one embodiment of the present invention.
Figure 42:
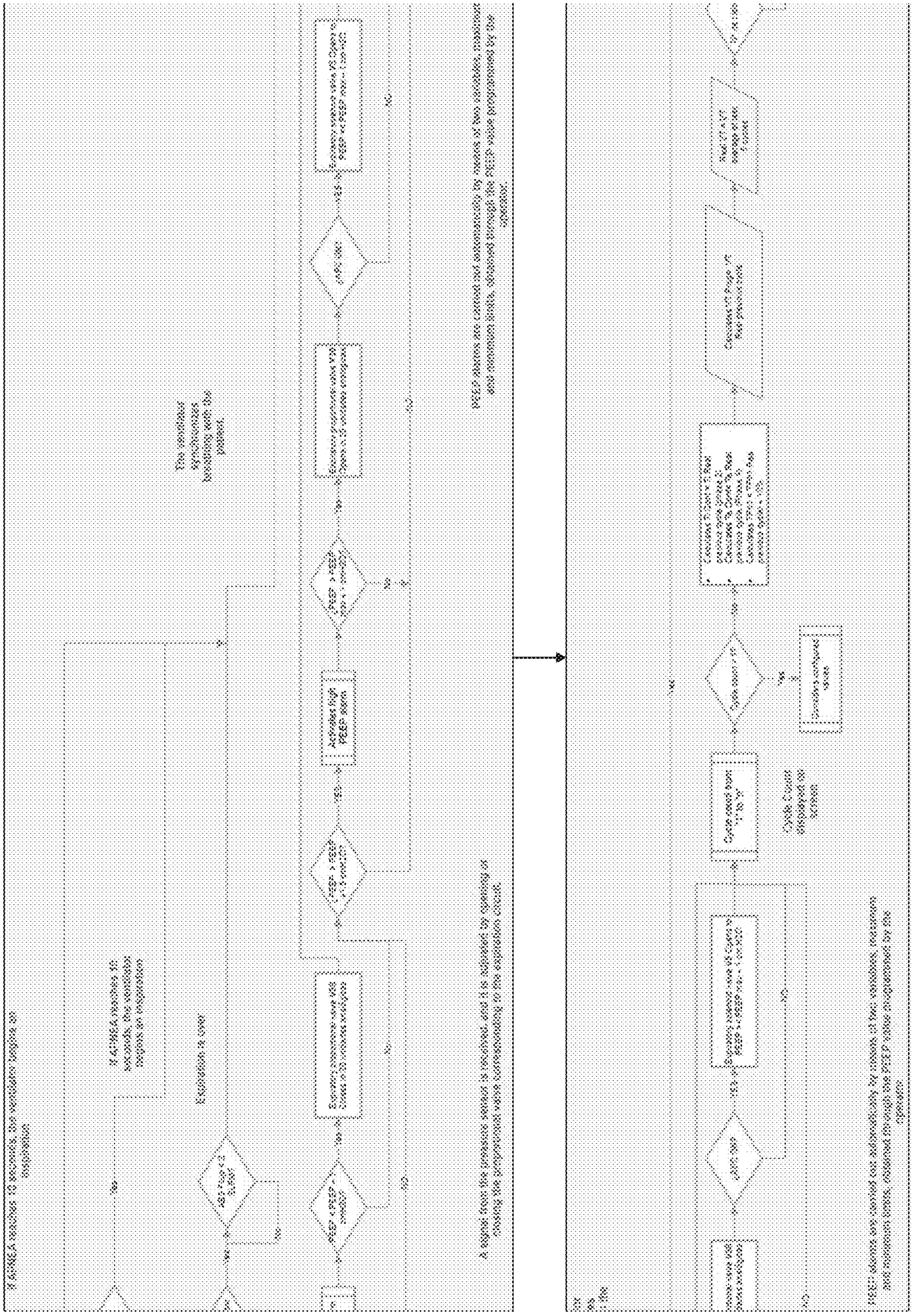
Figure 42:
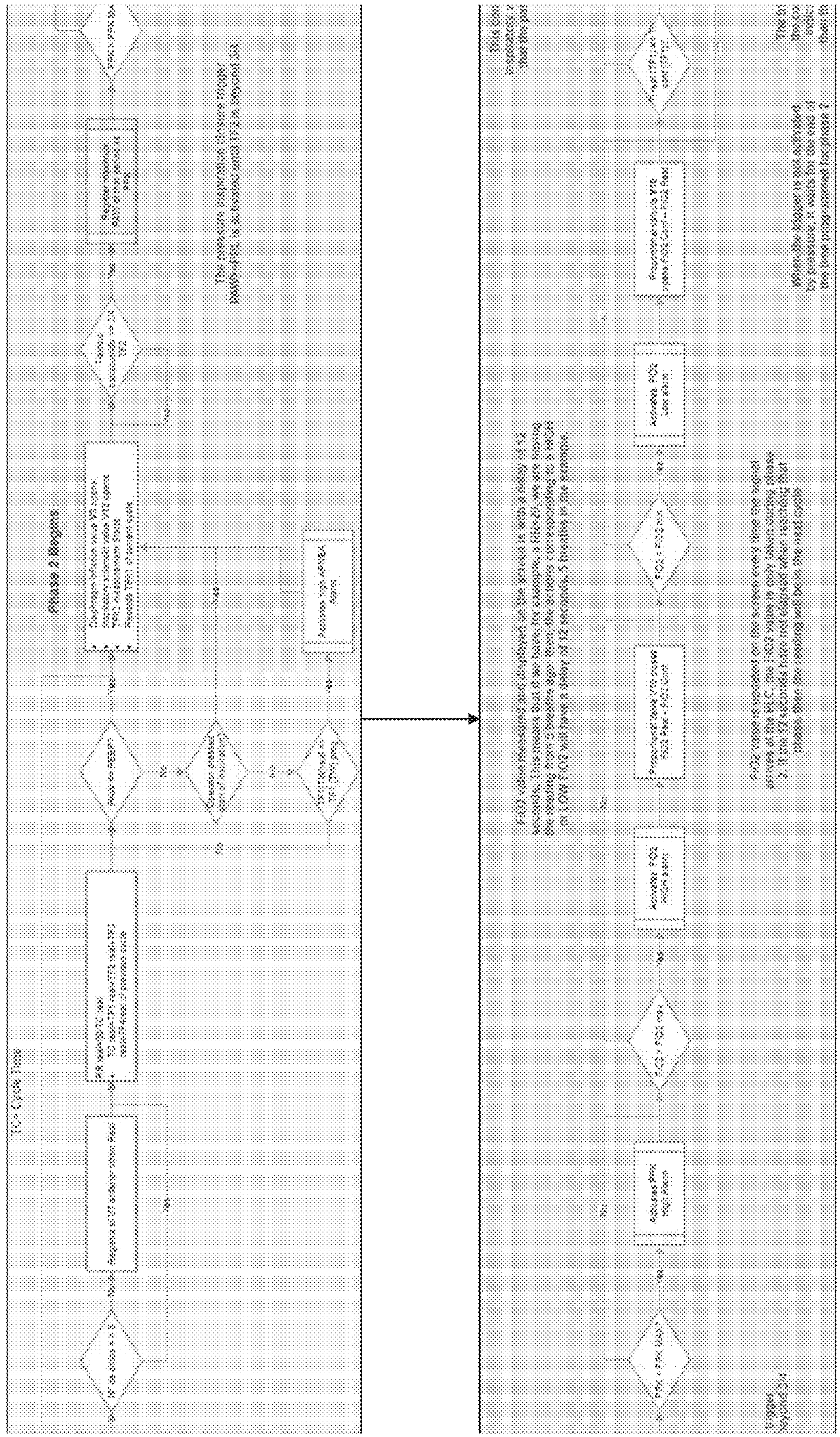
Figure 42:
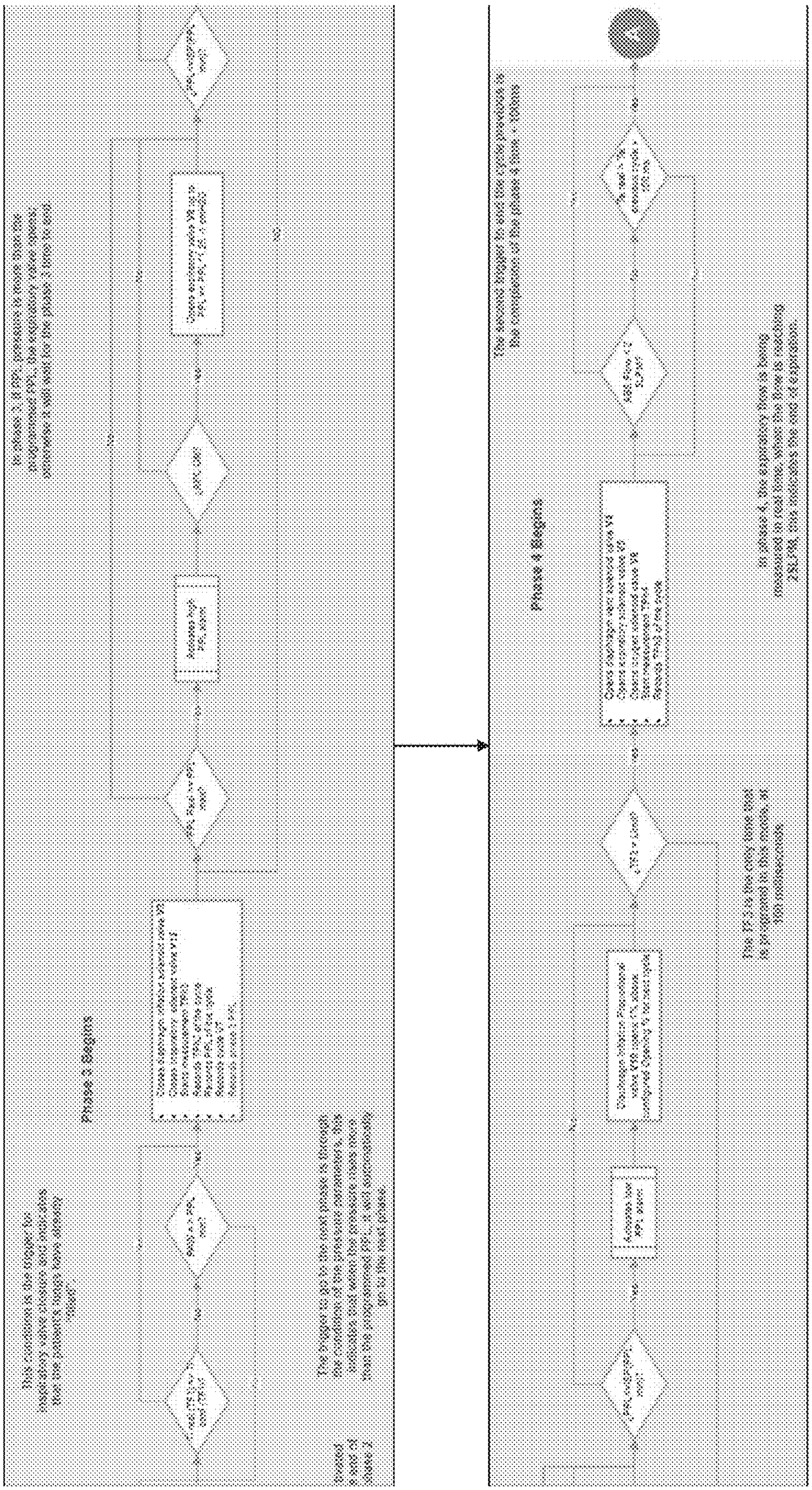
Figure 44:
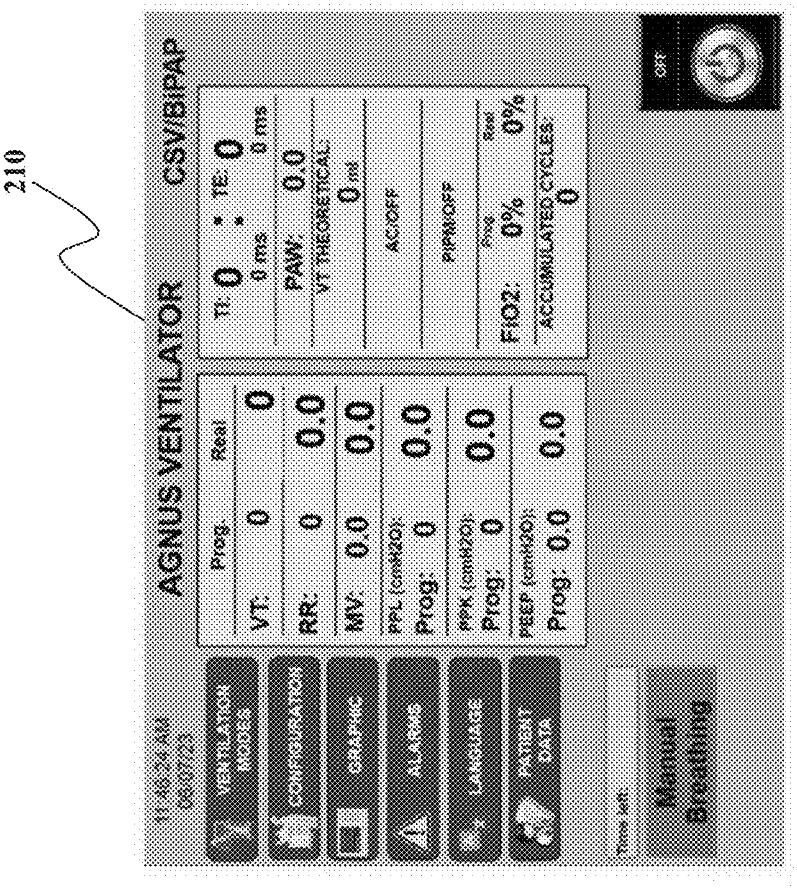
FIGS. 43-44 are schematic illustration of graphical user interfaces that may be displayed by the control system when executing the algorithms shown in FIG. 42.
Figure 43:
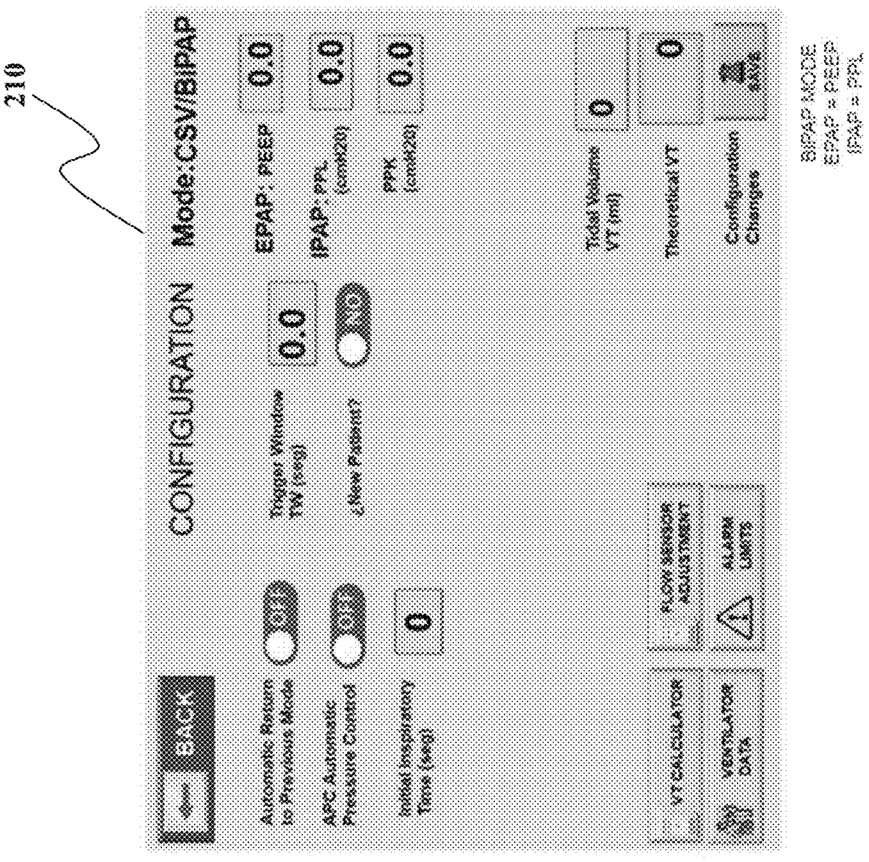
Figure 45:
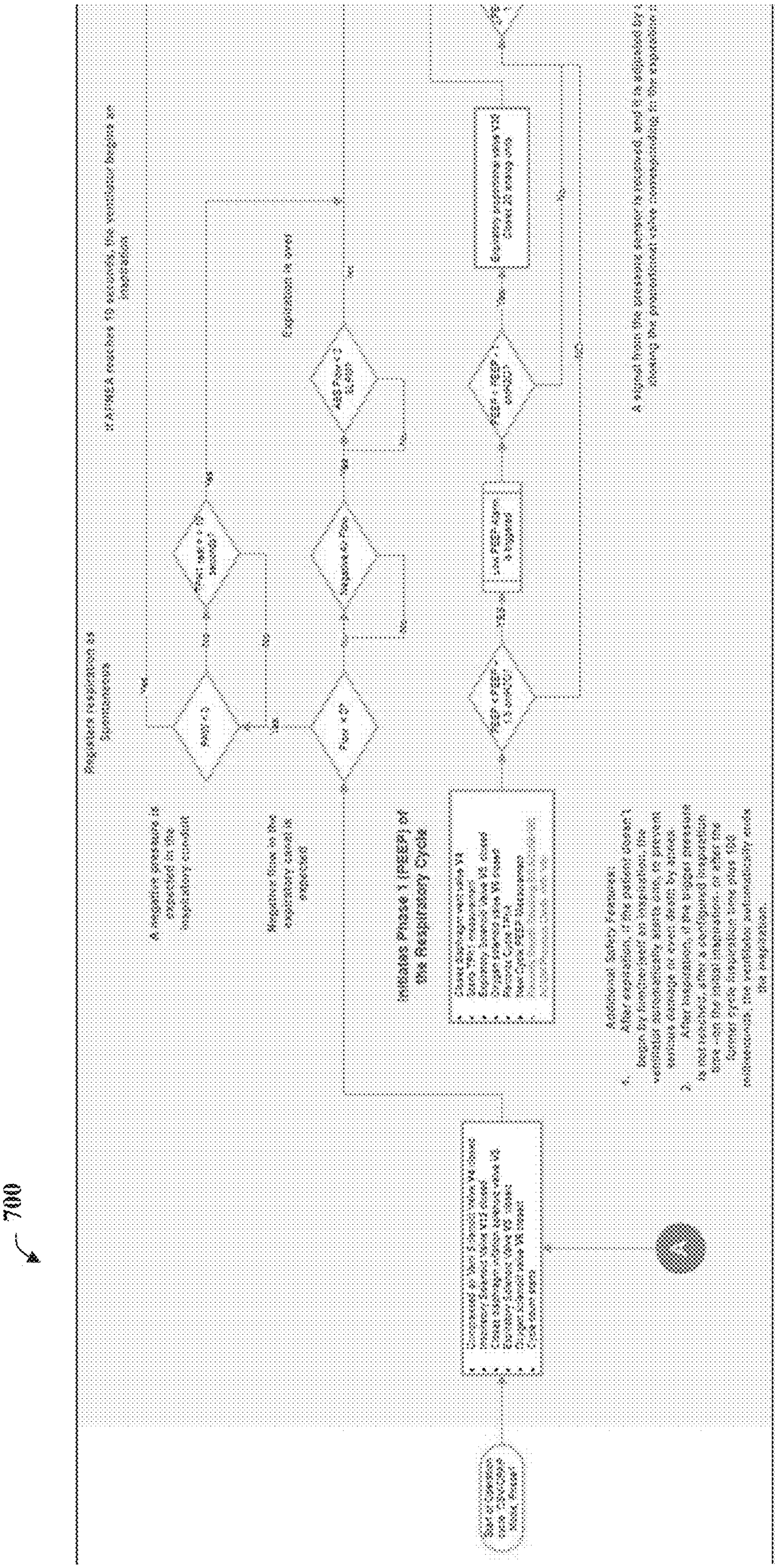
FIG. 45 is a flow chart illustrating another algorithm executed by the control system for use in operating the respirator ventilator device, according to one embodiment of the present invention.
Figure 45:
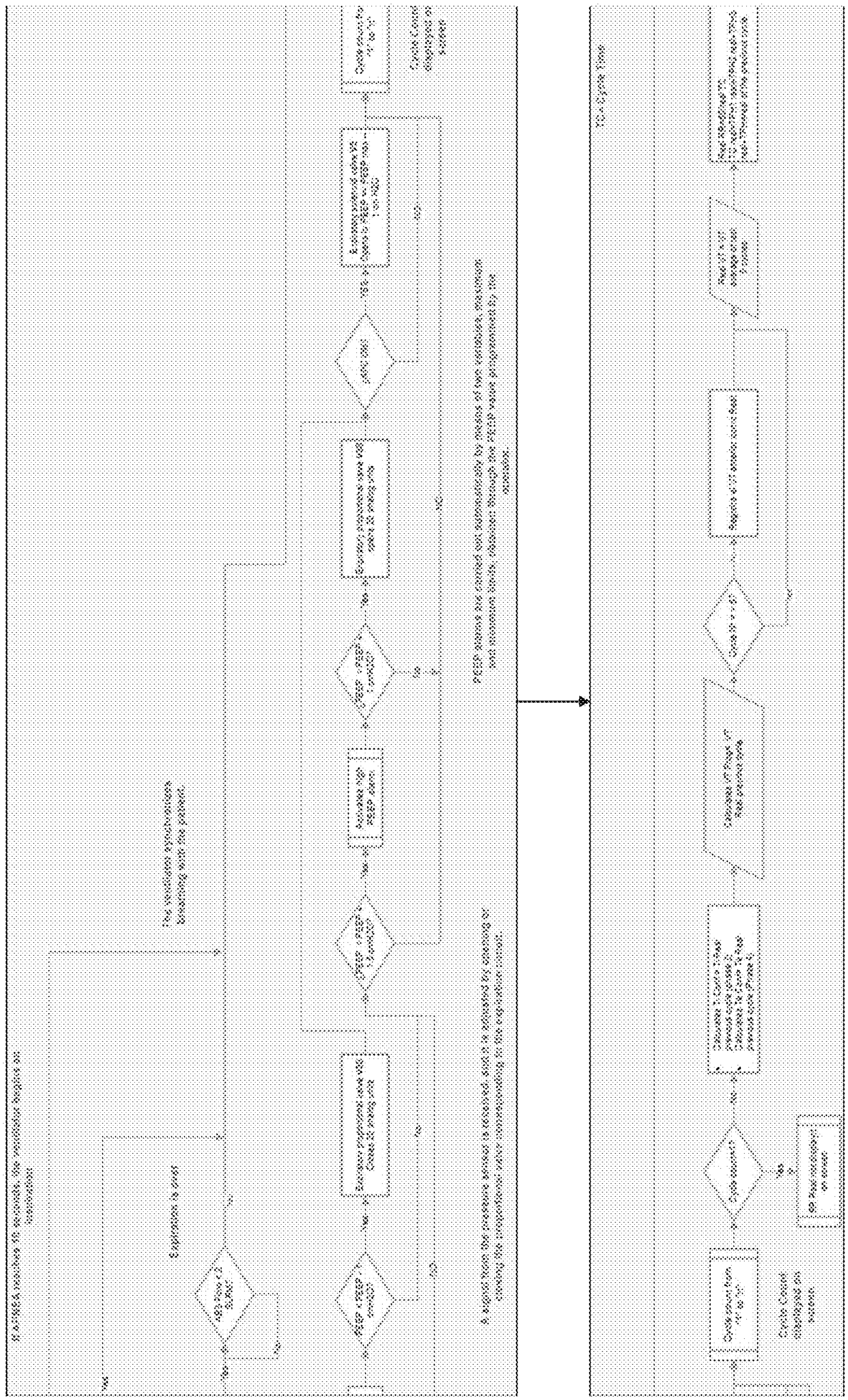
Figure 45:
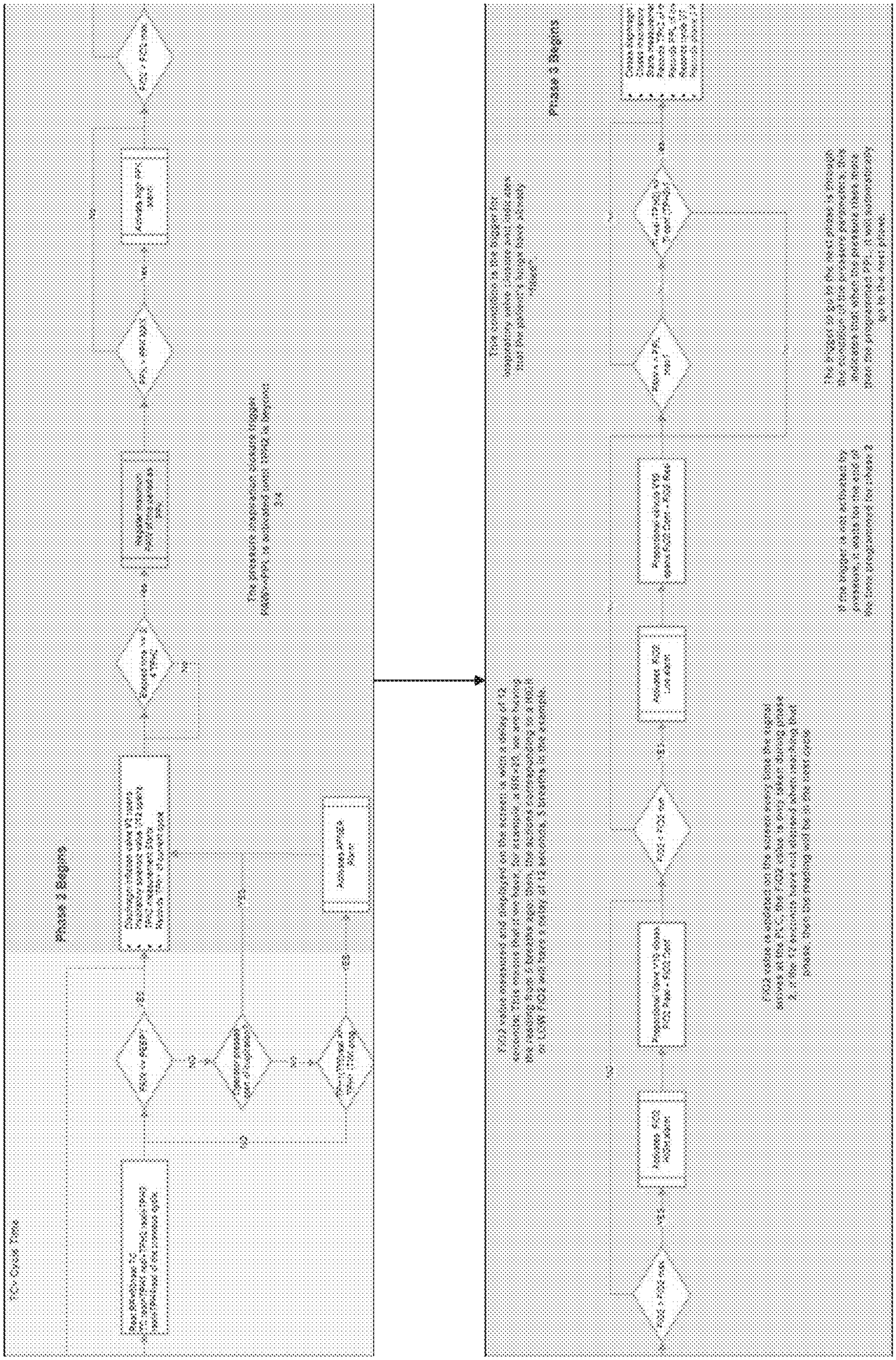
Figure 45:
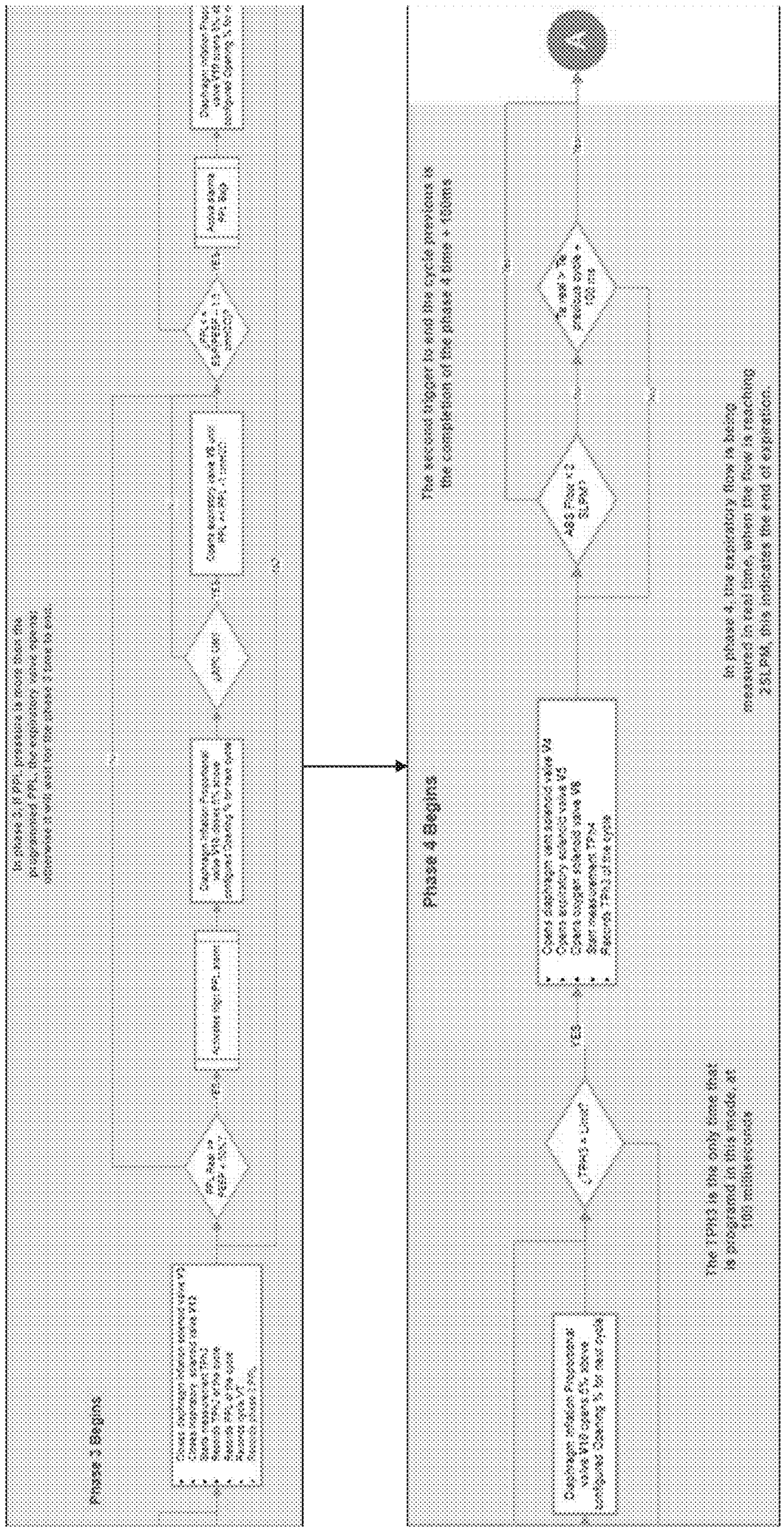
Figure 47:
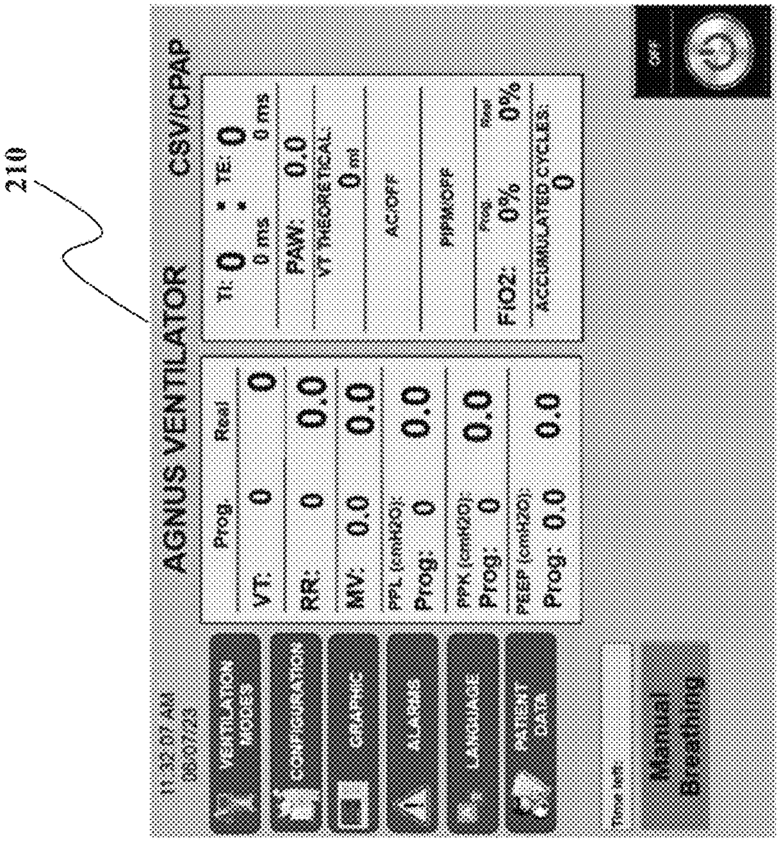
FIGS. 46-47 are schematic illustration of graphical user interfaces that may be displayed by the control system when executing the algorithms shown in FIG. 45.
Figure 46:
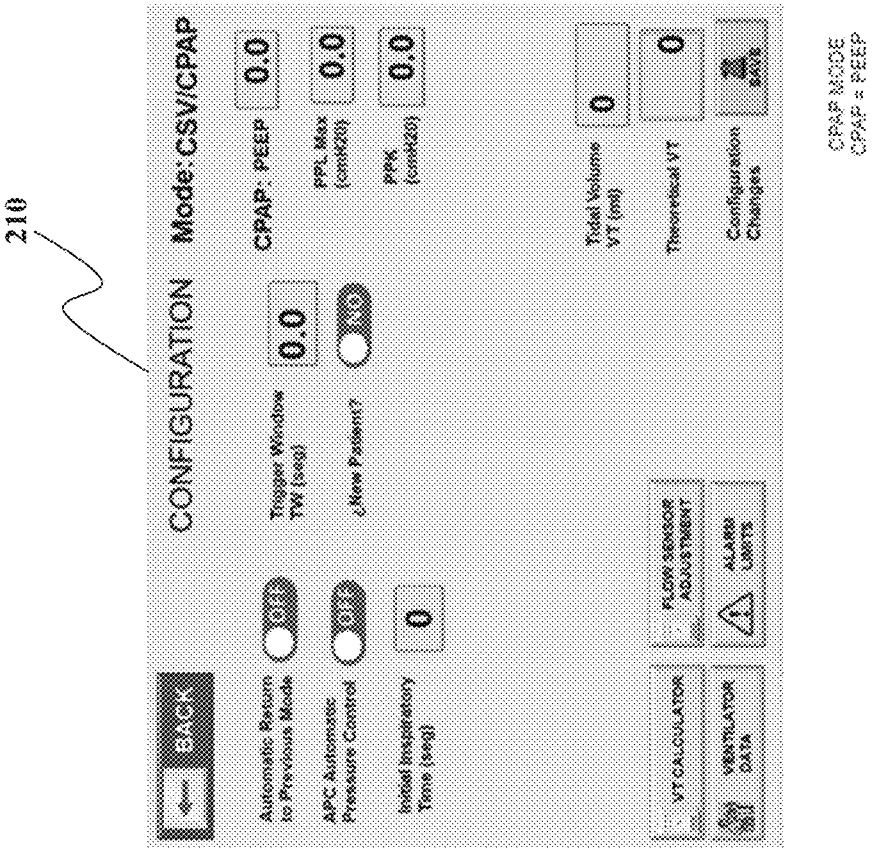
Figure 48:
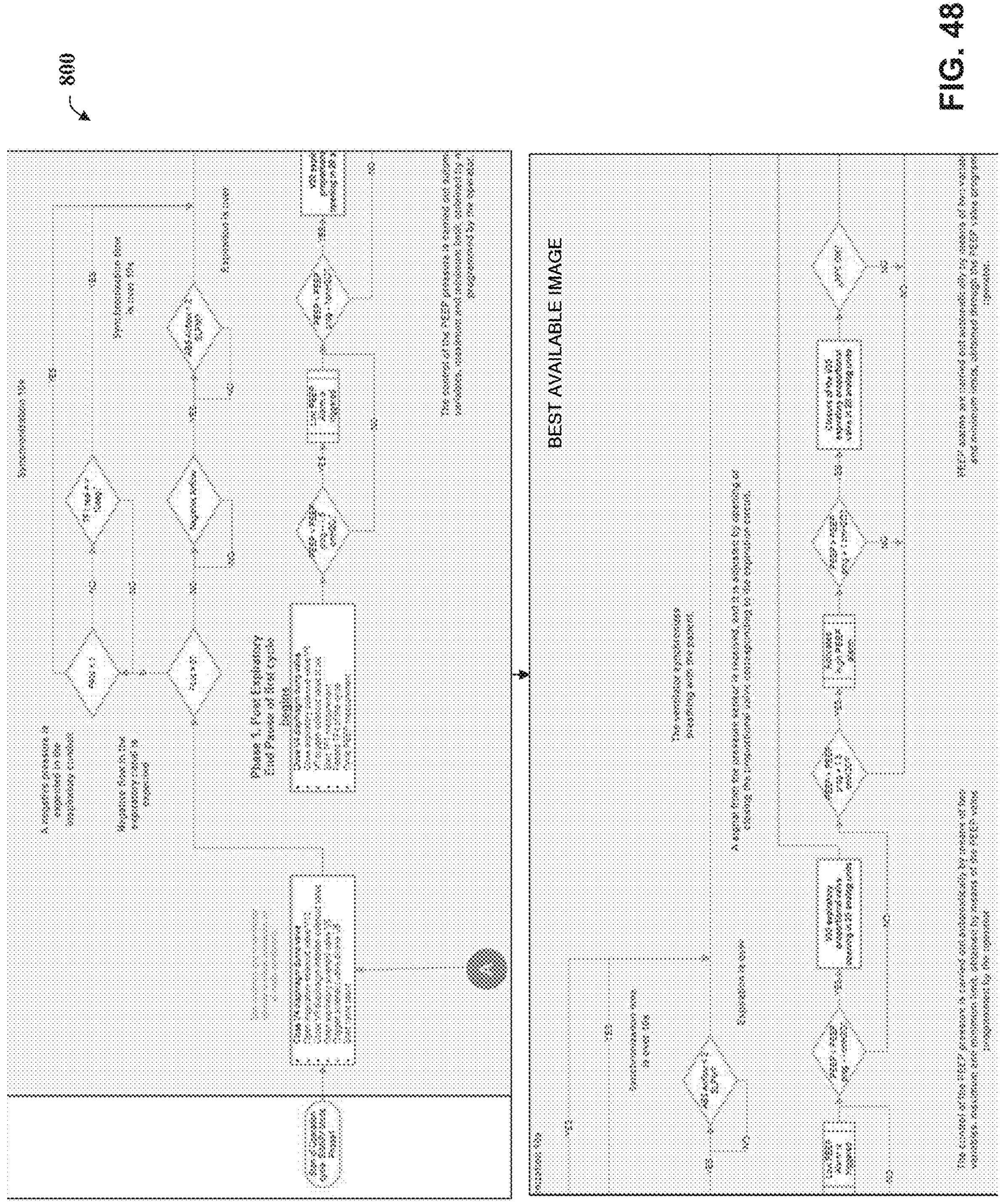
FIG. 48 is a flow chart illustrating another algorithm executed by the control system for use in operating the respirator ventilator device, according to one embodiment of the present invention.
Figure 48:
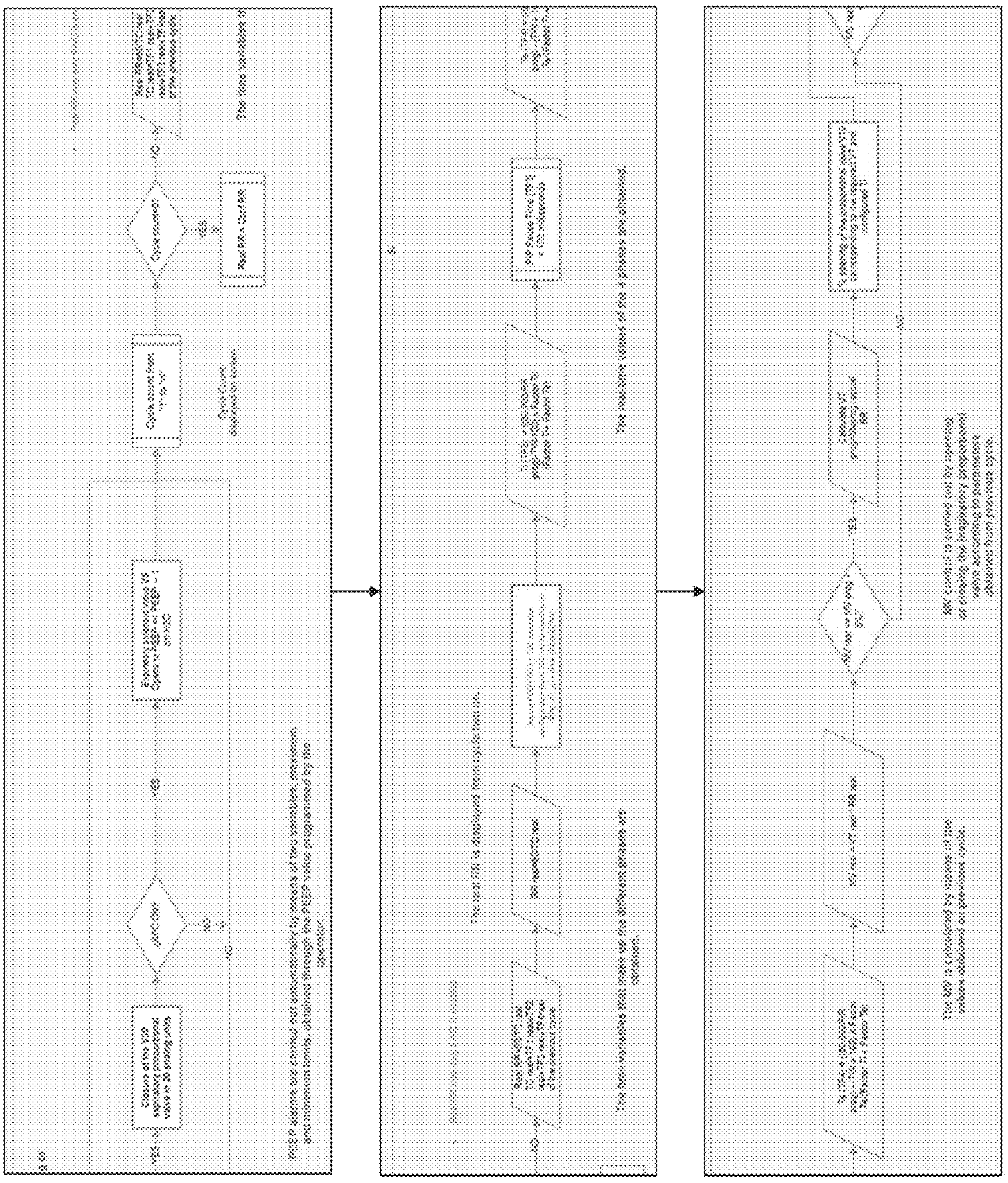
Figure 48:
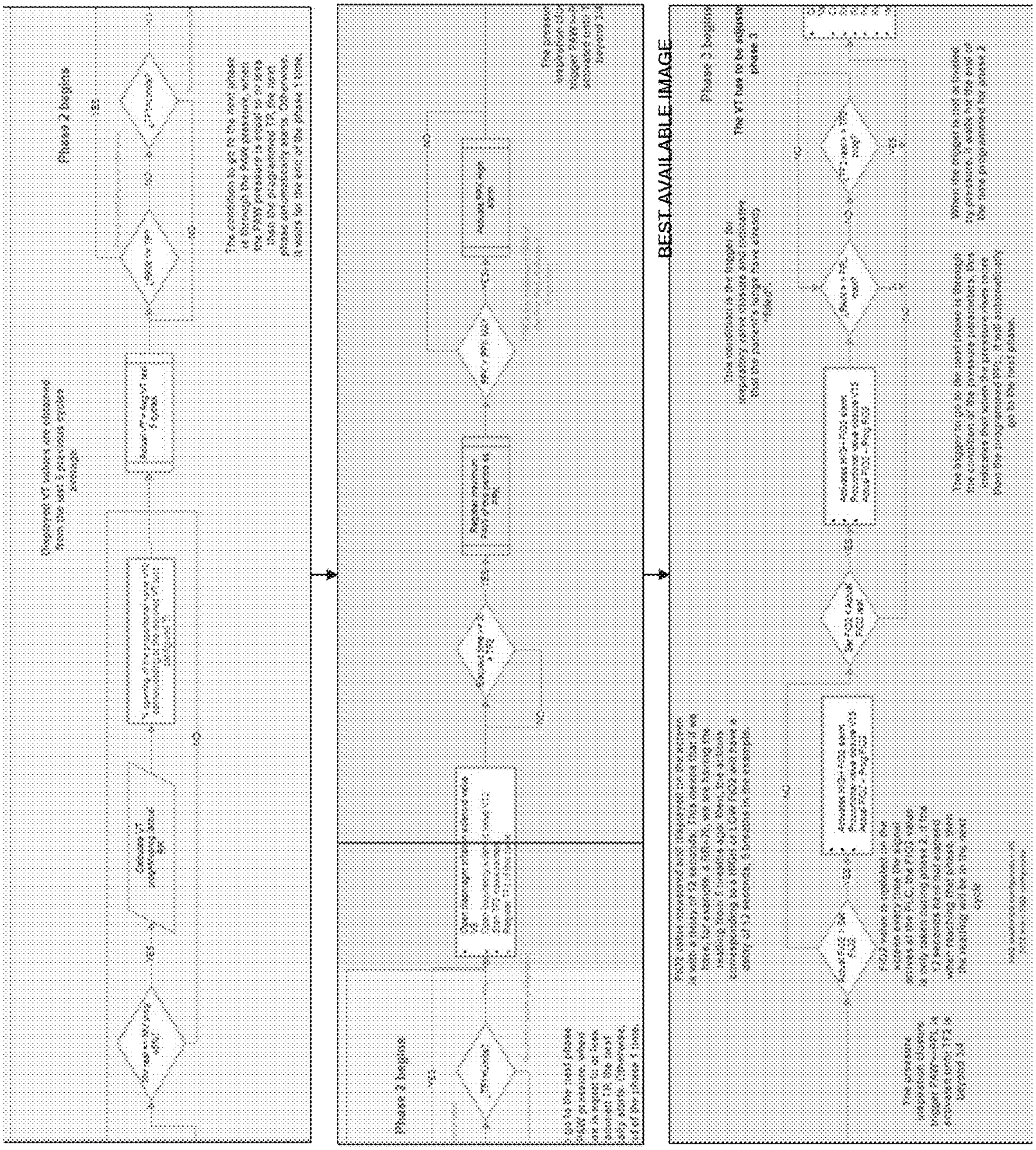
Figure 48:
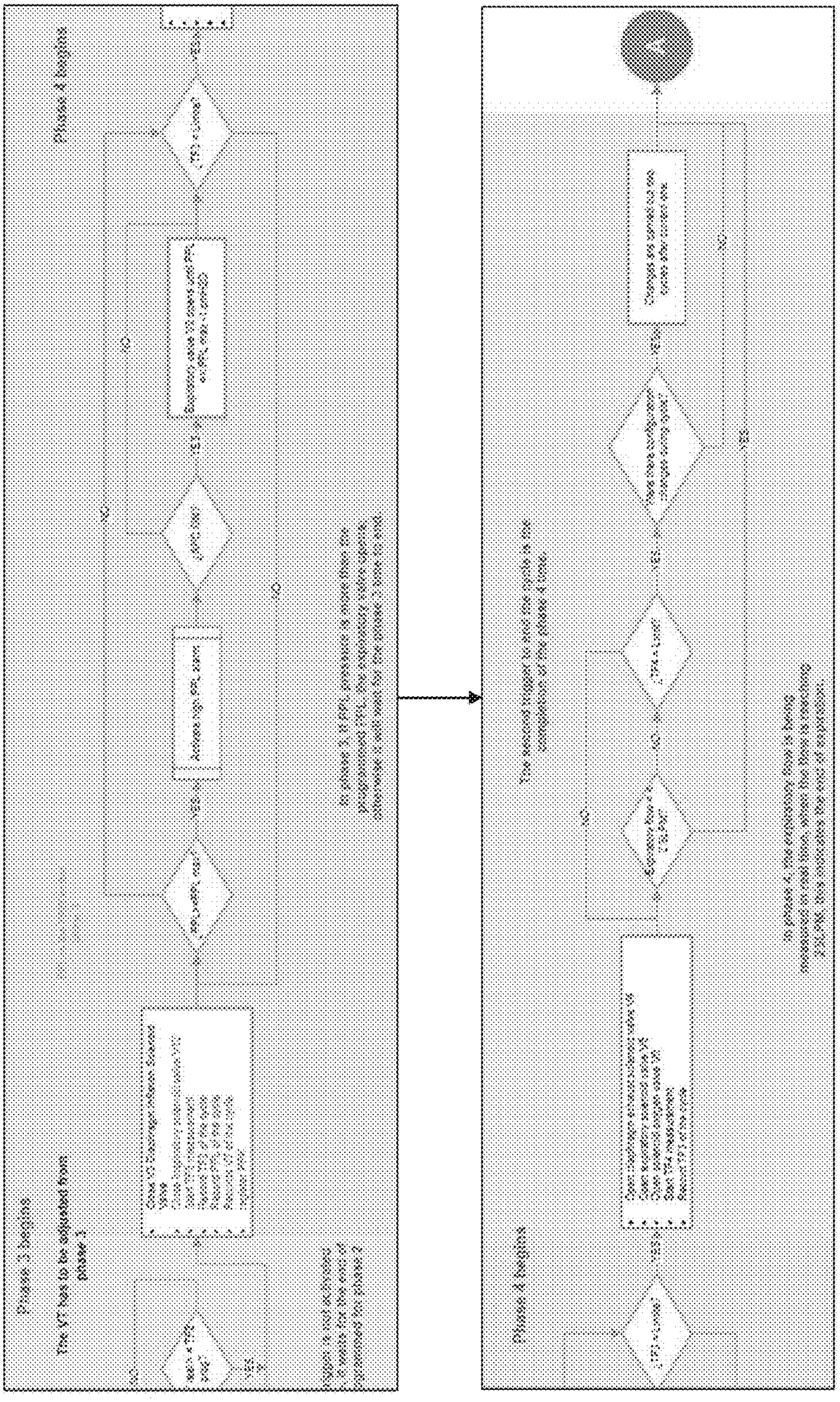
Figure 50:
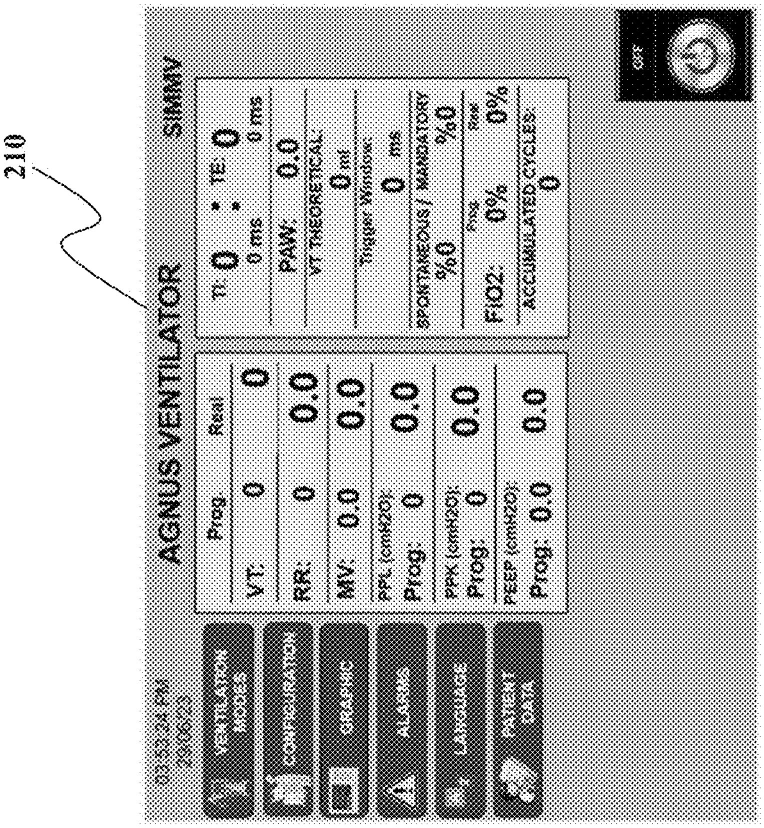
FIGS. 49-50 are schematic illustration of graphical user interfaces that may be displayed by the control system when executing the algorithms shown in FIG. 48.
Figure 49:
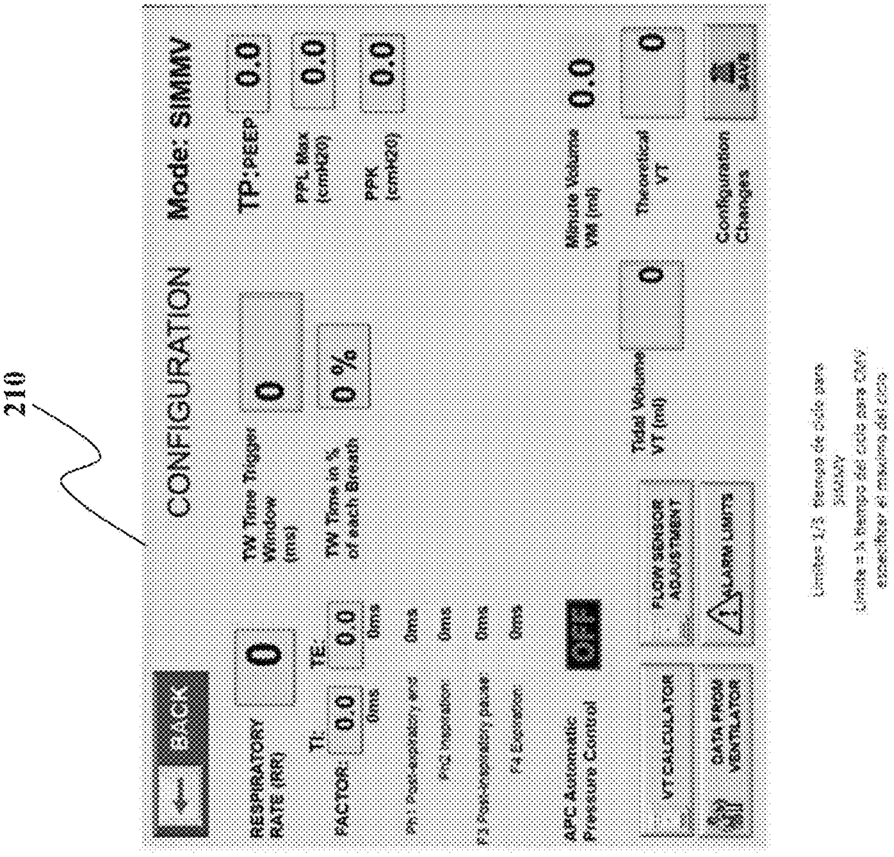
Figure 51:
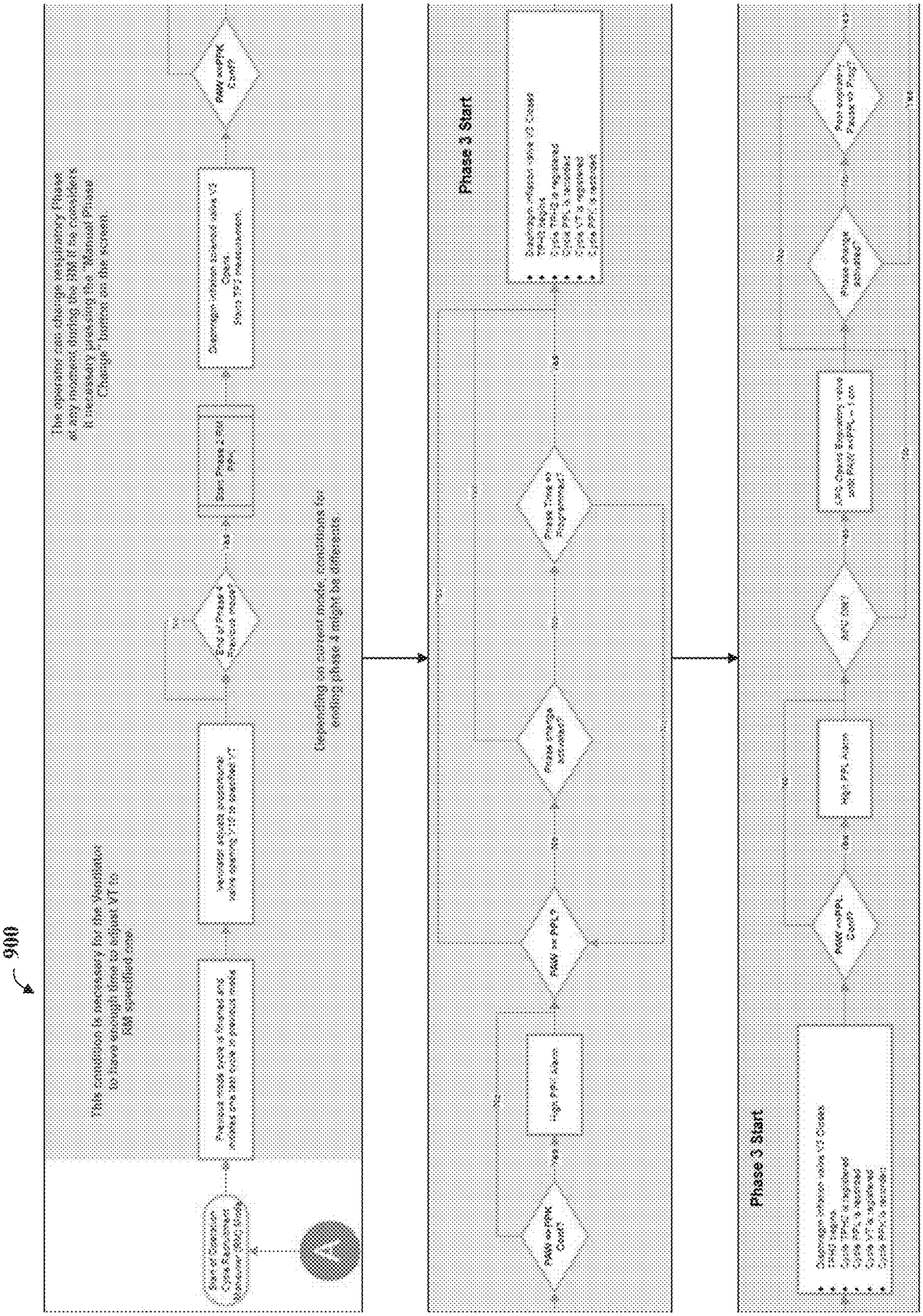
FIG. 51 is a flow chart illustrating another algorithm executed by the control system for use in operating the respirator ventilator device, according to one embodiment of the present invention.
Figure 51:
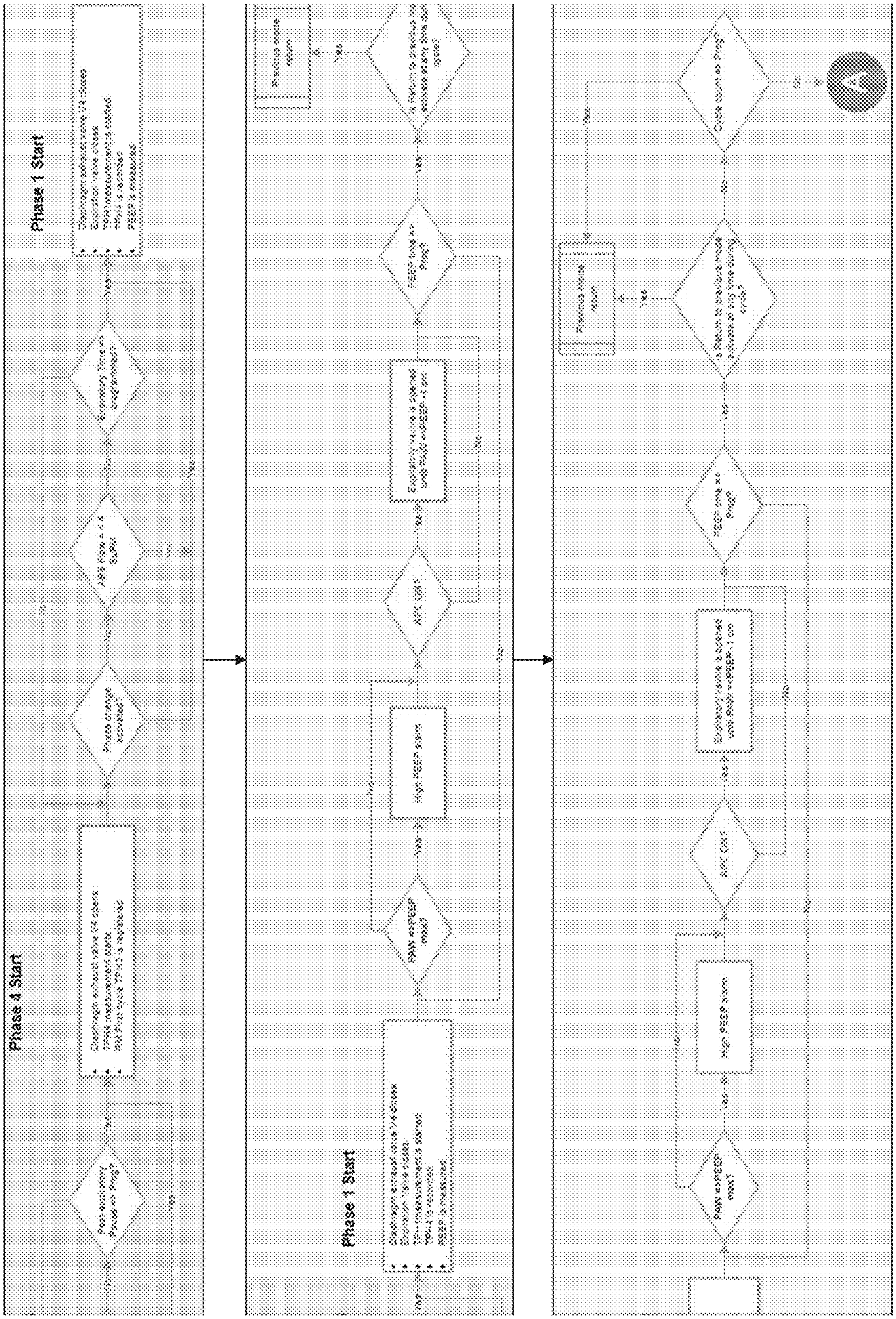
Figure 52:
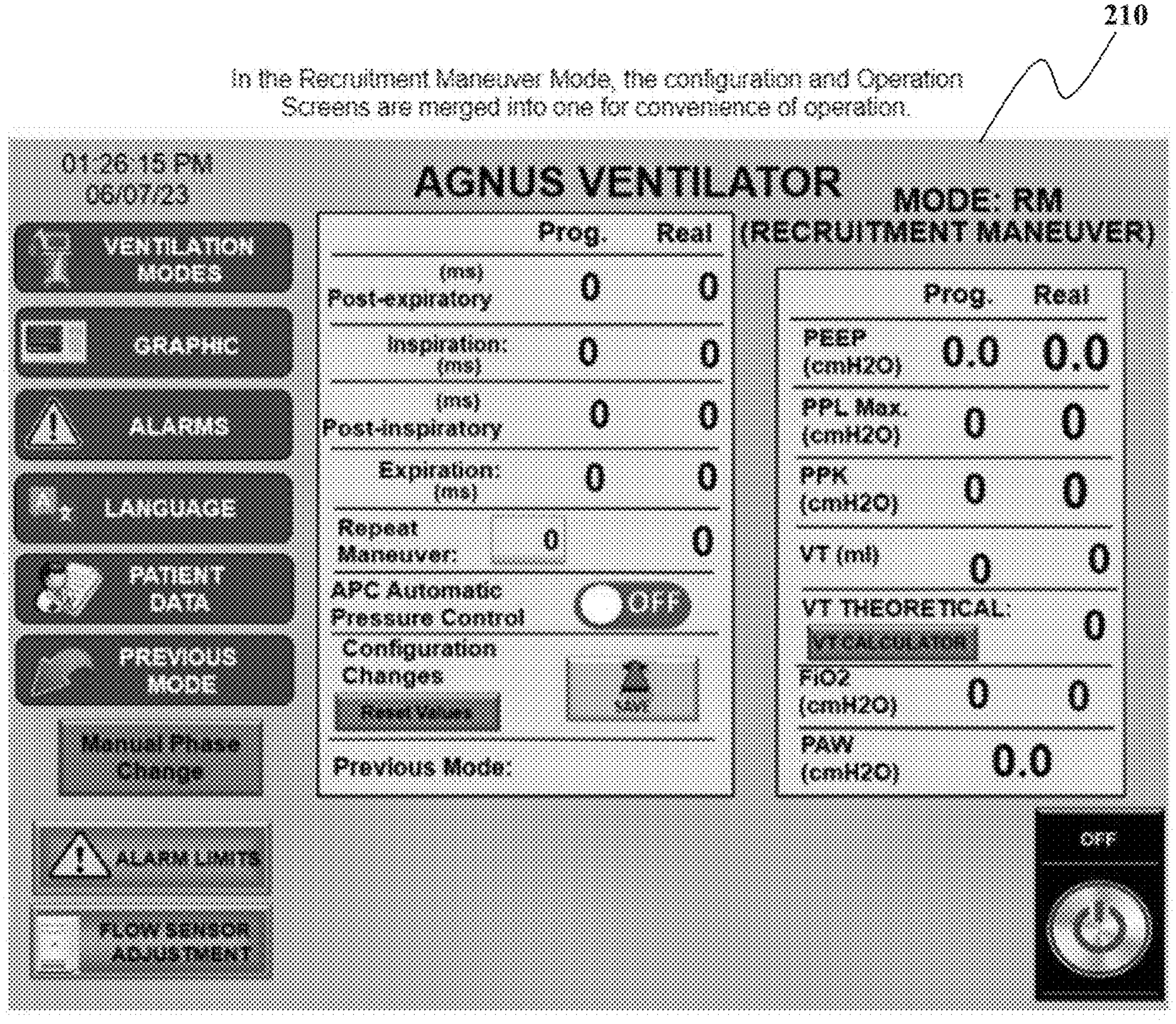
FIG. 52 are schematic illustration of graphical user interfaces that may be displayed by the control system when executing the algorithms shown in FIG. 51.
Figure 53:
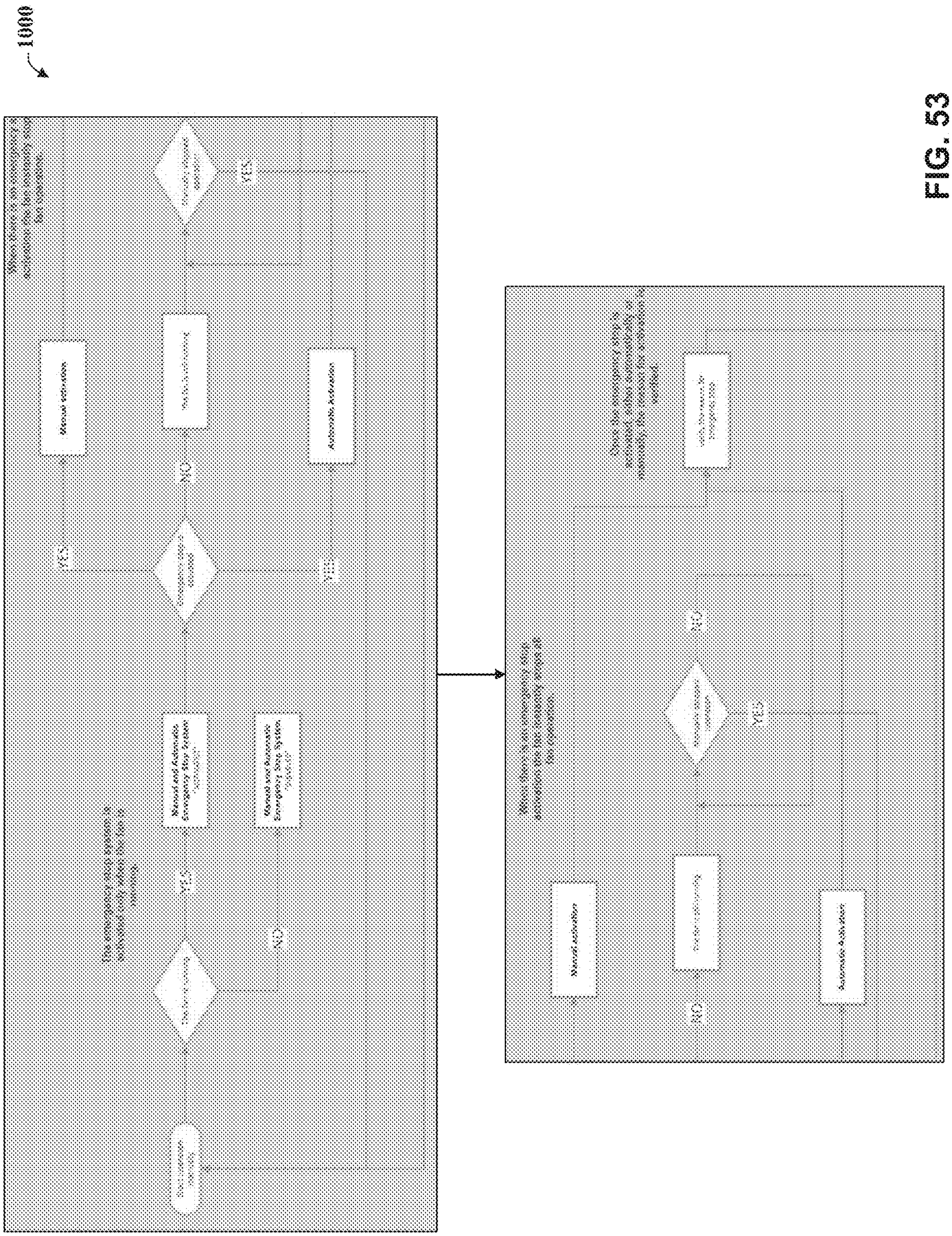
FIG. 53 is a flow chart illustrating another algorithm executed by the control system for use in operating the respirator ventilator device, according to one embodiment of the present invention.

For example, in Phase 2, solenoid valve 190 opens with a signal received from PLC 8*a* and solenoid valves 192, 160, 230 remain closed; Compressed air flows through solenoid valve 190 and proportional valve 188, which flow rate is adjusted by a signal from PLC 8*a*, to move diaphragm 122 upwards the distance necessary to deliver the Tidal Volume which has been previously set by the operator in a chosen mode configuring screen 210 in field 224 (FIG. 40) in touchscreen 208. The maximum airway pressure during this phase, known in the medical field as Peak Pressure or PPK, is measured by PLC 8*a* from several measurements sent as a signal by sensor 113 throughout this phase, and shown in touchscreen 208 operation screen (FIG. 41). The Tidal Volume displaced by diaphragm 122 as it is pushed upwards flows through Tee pipe fitting 140 towards patient passing through check valve 142, connector 204, inspiratory tubing 114 of respiratory circuit 3—respiratory circuit not being a part of this device—and through flow and pressure Sensor 113.

As inspiration air flows through tee pipe fitting 232, sensor assembly 144 sends a signal to PLC 8*a* which measures the percentage of oxygen in inspiration air—known in the medical field as Fraction of inspired oxygen ($FiO_2$)—, compares it with the $FiO_2$ set by operator in the appropriate ventilation mode configuration screen (FIG. 21-22, 40-41), and adjusts proportional valve 234 to deliver the amount of oxygen—$FiO_2$—set by operator from an oxygen supply 236.

The diaphragm 148, as it moves upwards, pushes remaining air exhaled by patient in Phase 4 of previous respiratory cycle through check valve 164 and exhaust air collection system 146 out of ventilator.

The Inspiration pilot light 216, which is 22 mm in diameter and clearly visible even from a distance of several meters, is turned on by PLC 8*a* during this phase to indicate that the patient is inhaling.

The trigger for ending Phase 2 and initiating Phase 3 can be time—measured by PLC 8*a*, pressure or tidal volume in the inspiratory airway; last two sensed by sensor 113 in 1.8 milliseconds—any one of the three parameters can be first; these conditions and the order in which they can trigger the phase change are specified by operator in the appropriate ventilation mode configuring screen (FIGS. 21-22, 40-41) chosen by operator in touchscreen 208.

In method step 308, the processor of controller 67 then operates the respiratory ventilator device 2 in a Phase 3 Post-inspiratory Pause. In phase 3, the processor of controller 67 operates all valves are closed and begins a counter, and after 100 milliseconds begins operation of phase 4. For example, in Phase 3, solenoid valve 190 closes and the rest of solenoid valves remain closed. This phase lasts 100 milliseconds. Sensor 113 sends in 1.8 milliseconds a signal to PLC 8*a* that measures airway pressure which in Phase 3 is known in the medical field as Plateau Pressure or PPL, and displays it on Touchscreen 208 in operation screen. The trigger for ending Phase 3 and initiating Phase 4 is time, 100 milliseconds measured by PLC 8*a*.

In method step 310, the processor of controller 67 operates the respiratory ventilator device 2 in a Phase 4 Expiration. In Phase 4, processor of controller 67 operates valves 192 and 160 to open allowing expiration air from the patient. The processor of controller 67 then operates valves 192 and 160 close when time, pressure, or Flow & Pressure are reached. At this point one respiration cycle ends and begins another. The processor of controller 67 operates the expiration pilot light 214 on the ventilator front panel 168 to light up during this phase, indicating that expiration is being carried out. For example, in phase 4, solenoid valves 190 and 230 remain closed and solenoid valves 192, 160 open; solenoid valve 160 allowing expiration air from patient to flow through it, and solenoid valve 192 allowing compressed air on the undersides of both diaphragms 122 and 148 to vent out of the compressed air conduit of ventilator inside its housing through connector 184, which also functions as cooling for solenoid and proportional valves inside the ventilator housing. Both diaphragms 122, 148 return to their central positions, diaphragm 122 allowing fresh air to flow in its casket housing through inhalation check valve assembly 134 and Oxygen through solenoid valve 230. Diaphragm 148 assists patient in expiration—this term is preferred instead of exhalation in the medical field—so as to overcome the resistance to flow that the expiration conduit presents, and also from the filters that can be installed in said conduit. As can be seen in FIG. 19, once solenoid valve 160 is open, the expiration airway is open from patient through check valve 164 to exhaust air collection system 146.

During phase 4, the expiration pilot light 214, which is 22 mm in diameter and clearly visible even from a distance of several meters, is on during this phase to indicate that the patient is expirating.

The trigger for ending Phase 4 and initiating Phase 1 can be time—measured by PLC 8*a*—, pressure or tidal volume in the expiratory airway; last two sensed by sensor 113 in 1.8 milliseconds-any one of the three can be first-; these conditions and the order in which they can trigger the phase change are specified by operator in the appropriate ventilation mode configuring screen chosen by operator in touchscreen 208.

The processor of controller 67 is also programmed to initiate a plurality of Alarms. For example, a visual and audio buzzer are activated when parameters go out of their specified values or there is a failure in compressed air supply. The buzzer can be silenced by operator; alarm pilot light will remain on until deviation is corrected.

The processor of controller 67 is also programmed to initiate an Emergency Stop in which the PLC 8*a* closes valve 190 and opens valves 142, 192, 160. When deactivated and the ventilator is re-started, the processor of controller 67 will resume at the point in which it had stopped.

The processor of controller 67 is also programmed to initiate a Momentaneous Stop, which is initiated by the operator by push-button and while pressed, the processor operates valves 142, 192, 190, 234, 160 to remain closed. When released the ventilator reassumes operation at the exact point where it stopped.

When APC is on, valve 160 opens in case AWP exceeds set value in a certain phase.

Figure 23:
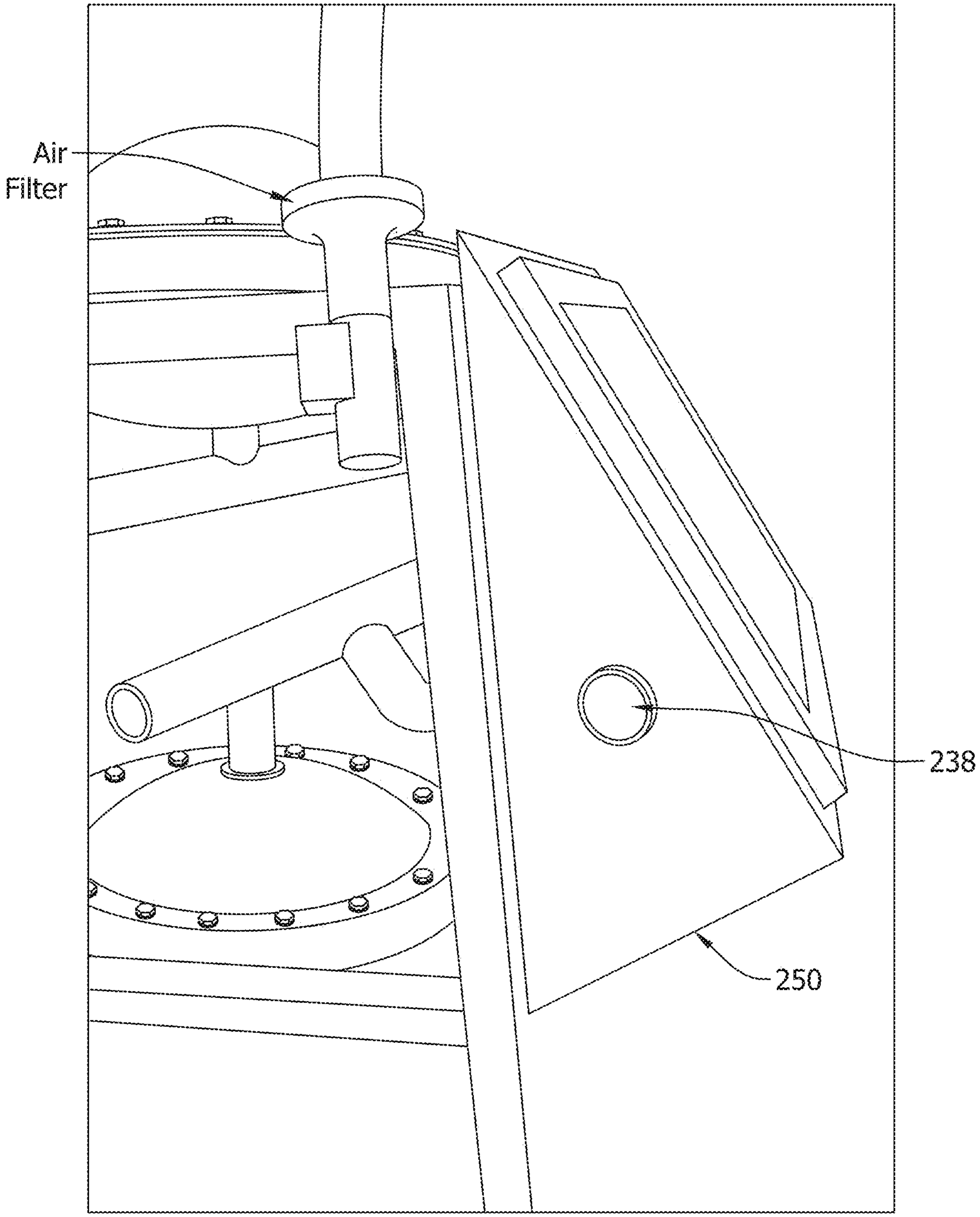
FIGS. 23-36 are perspective views of the respirator ventilator device, according to embodiments of the present invention.

In FIG. 23, on the left triangular panel of the Touchscreen 208, there is a push button 238 measuring 22 mm in diameter, making it easily findable even by tact only that, when pressed, stops instantly the ventilator's operation at the exact point of the respiratory cycle in which it was when pressed, closing all Solenoid valves. This is very useful for the operator for checking pressures at any phase, and, especially important from a medical point of view, to perform so called in medical terms recruitment maneuvers to get collapsed alveoli back in function, thus increasing oxygenation of patient and improving patient's recovery chances. It is outside the scope of the present application to delve deeper into this medical issue.

When said push button 238 is released, the ventilator reassumes operation at the exact point of the respiration cycle where it was before the push button 238 was pressed. One advantage of this configuration is that the respiratory therapist operating the ventilator does not have to waste valuable time looking for how to perform recruitment maneuvers in the ventilator screen as commands or buttons, as currently happens with ventilators in use.

Figure 24:
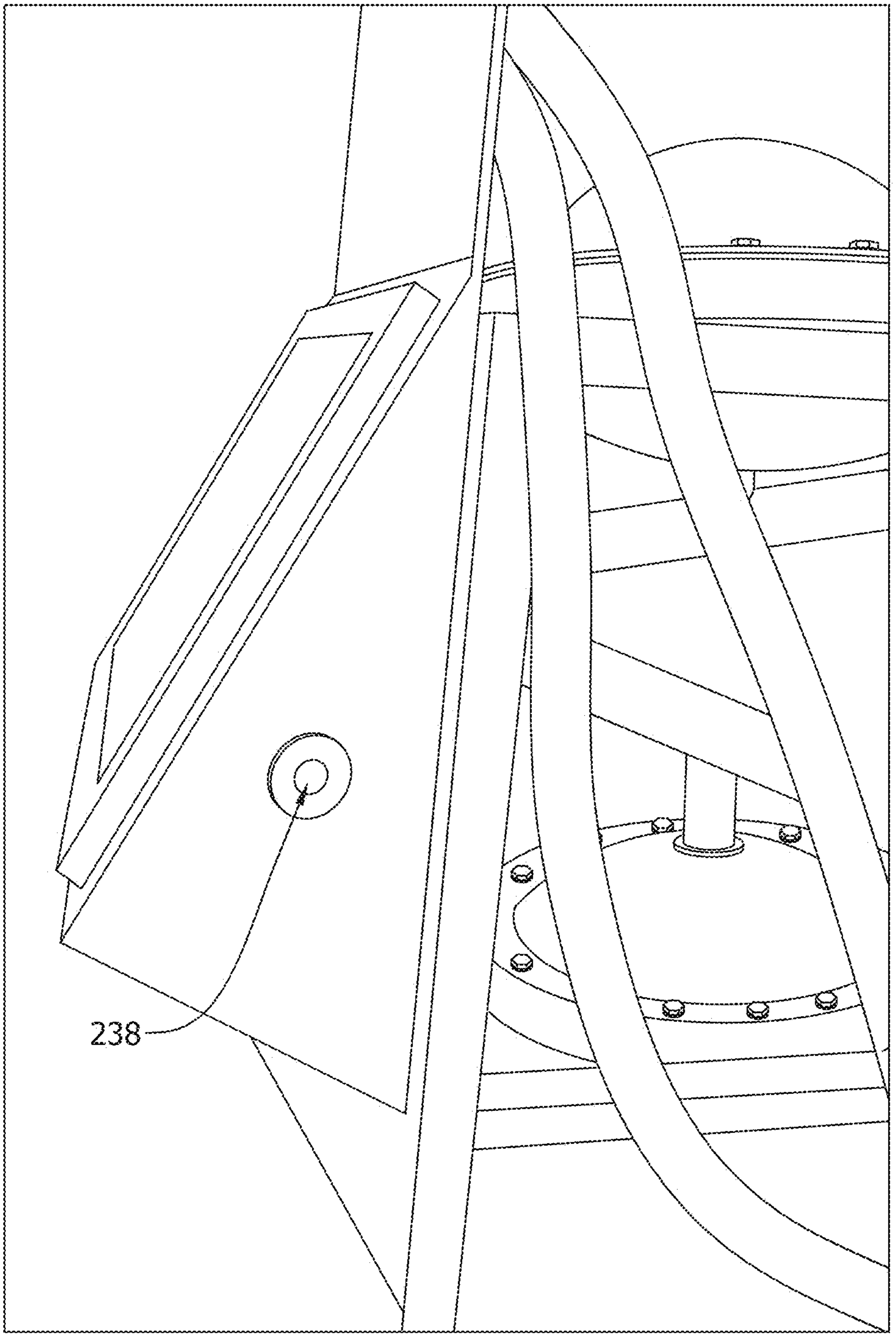
Figure 25:
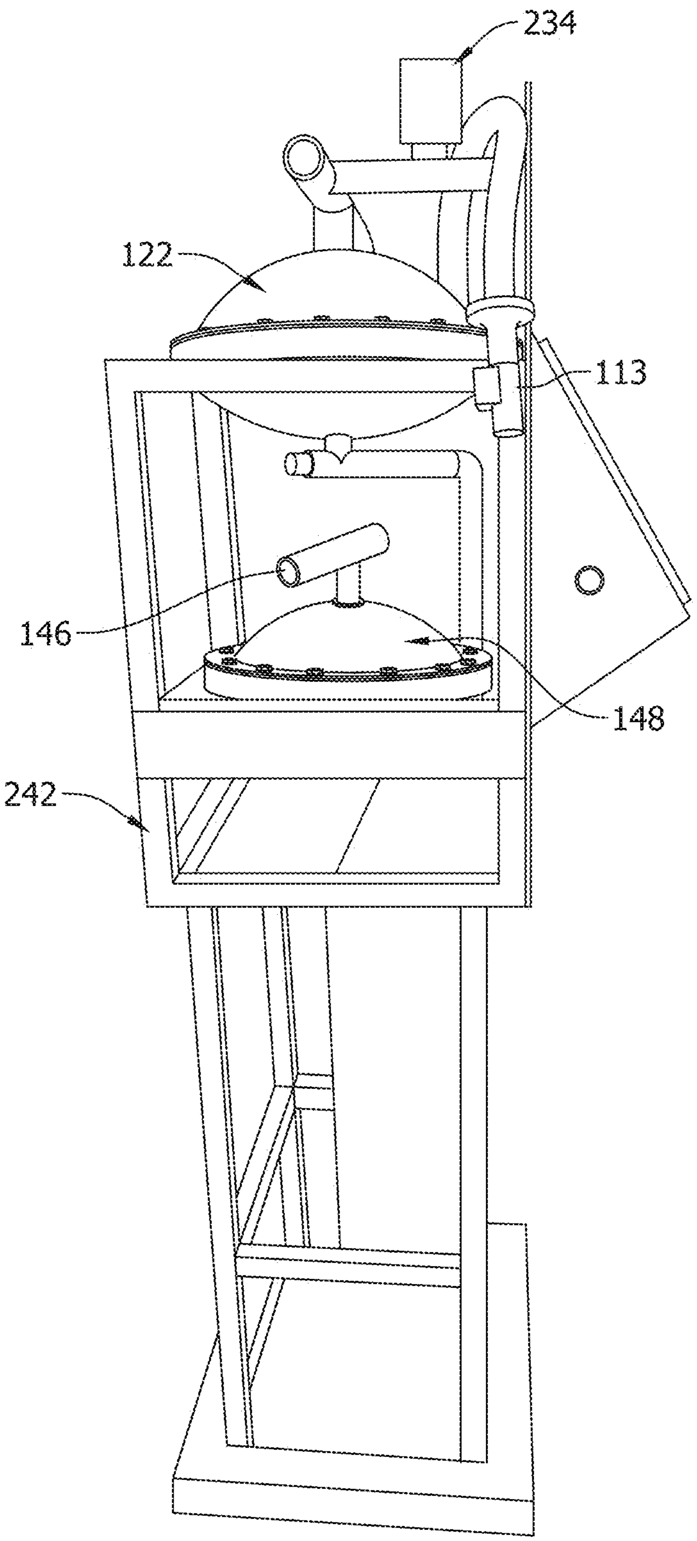
Figure 26:
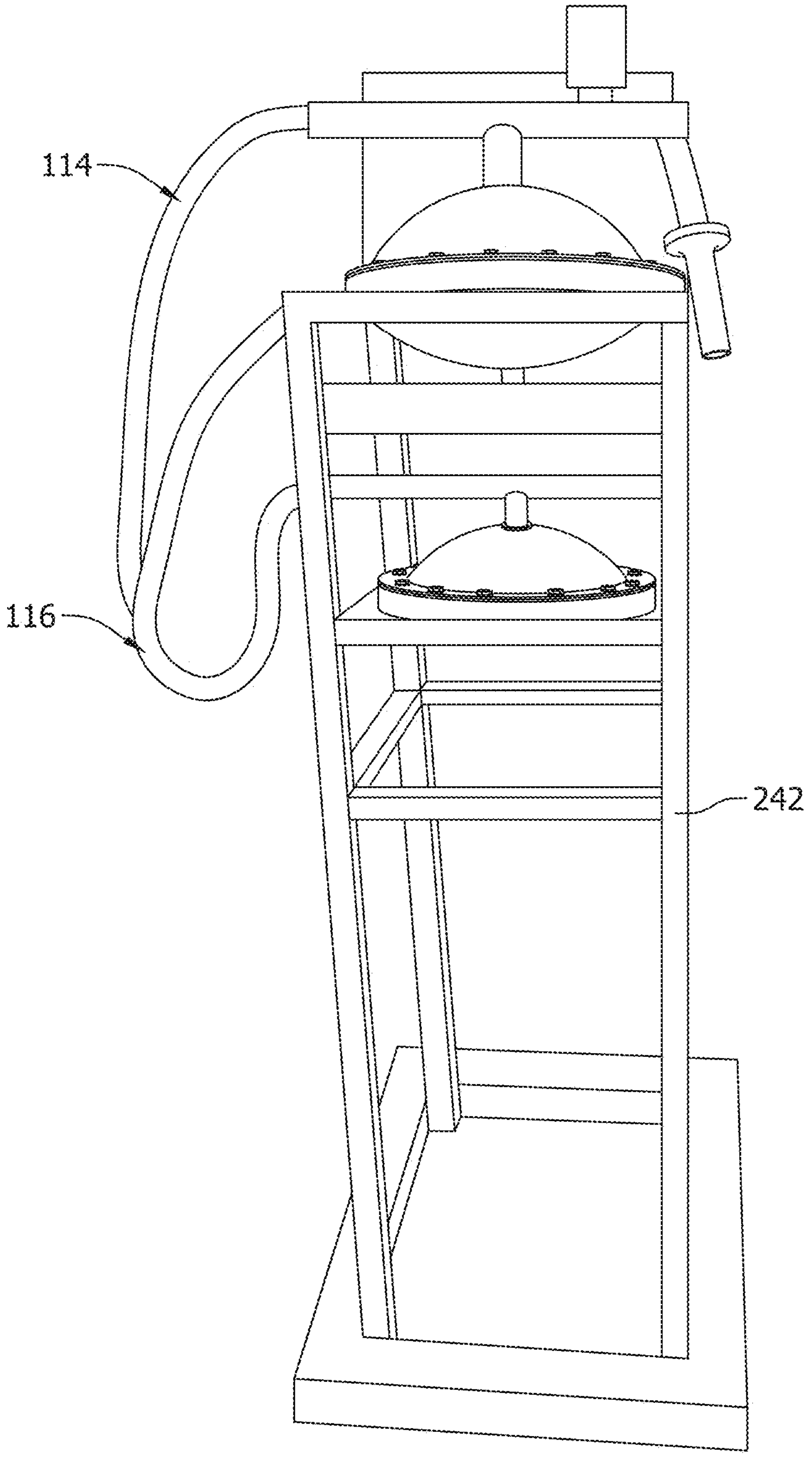
Figure 27:
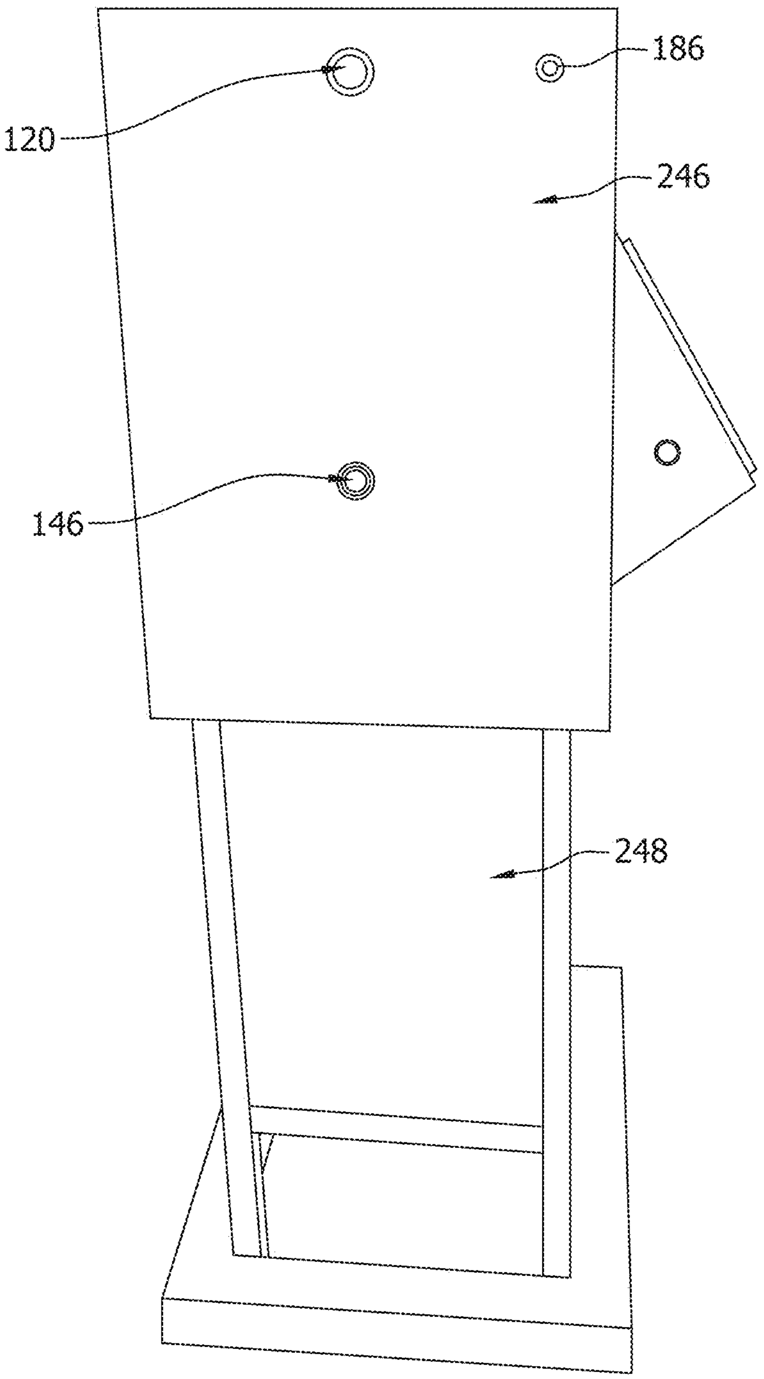
Figure 28:
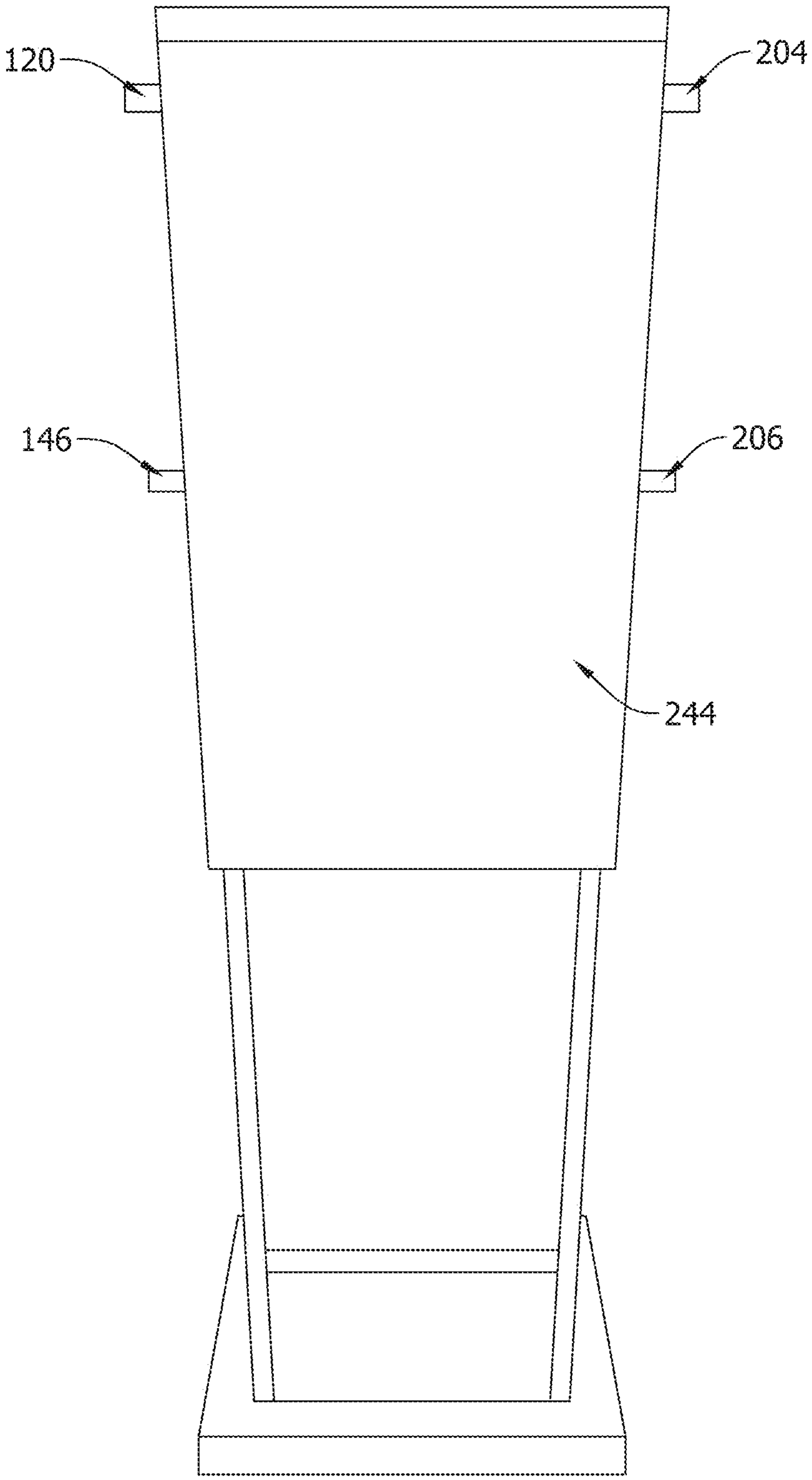

In FIG. 24, on the right side triangular panel of Touchscreen 208 there is a large—35-mm in diameter—Emergency Stop button 238, that, when pressed, stops immediately the ventilator operation, simultaneously closing compressed air supply solenoid valve 190 (FIG. 19) and oxygen supply solenoid valve 230, which are of the Normally Closed NC type, and opening compressed air vent solenoid valve 192 and exhalation solenoid valve assembly 160, which are of the Normally Open NO kind, thus allowing patient to spontaneously breath freely from surrounding air, therefore preventing patient's suffocation. Check valve 142 and inhalation check valve assembly 134 on the inspiration conduit of ventilator and check valve 164 on expiration conduit, only allow fresh air to enter the respiratory circuit for inspiration, and prevent expiration air mixing with inspiration air, making it safer.

In the case of a power failure or ventilator completely stopping, compressed air supply solenoid valve 190 and oxygen supply solenoid valve 230 which are of the Normally Closed NC type both close, and opening compressed air vent solenoid valve 192 and exhalation solenoid valve assembly 160, which are of the Normally Open NO kind, thus allowing patient to breath freely from surrounding air avoiding entirely the risk of suffocating patient permitting patient to breathe spontaneously.

The configuration and activation of alarms, visual alarm pilot light 212 and audible Buzzer 222, is done by operator on the alarm configuring screen on Touchscreen 208. When, through the signal received by PLC Sa from sensors 113 and 144, the PLC Sa detects that any parameter such as Tidal Volume, Pressures, flow rate, respiratory rate, $FiO_2$, Apnea, and others are out of the values or ranges specified by operator in the alarm configuring screen. Audible Buzzer 222 and visual alarm pilot light 212 alarms activate, and an alarm window on operation screen Touchscreen 208 will register and display cause and initial and final times for each one activated. Ventilators currently in use allow, as the present invention does, the audible alarm to be silenced, but the ventilator herein described doesn't allow the visual alarm to be shut off, and it only shuts off when all parameters are within ranges specified. It is important to point out that the visual alarm is large as pilot lights. These aspects are vital least the operator gets distracted from a potentially hazardous situation with the patient.

In all modes configuring screens, e.g. FIG. 40, there is a button "Automatic Pressure Control" APC 240 activated by default and only can be deactivated by operator, that, when activated, it will make the PLC 8*a* send a signal to open solenoid valve 160 when, in any phase, airway pressure, PPK, PPL, or PEEP as measured by the PLC 8*a* with sensor 113 signal, exceeds that of the upper limit set by the operator to release air pressure and when said pressure falls back below its upper limit, the PLC 8*a* sends a signal to solenoid valve to close. This is done in a few milliseconds because the sensor 113 response time is 1.8 milliseconds. This is a feature that help prevent volutrauma to alveoli—a medical condition out of the scope of this description—from excessive pressure or volume.

The method of using the exhalation solenoid valve assembly 160 simultaneously as a pressure relief valve simplifies the ventilator construction, and also facilitates the design of the control process algorithms and programming.

As shown in FIGS. 23-29, in some embodiments, the respiratory ventilator device 2 includes a support frame 242 that is made of commercial stainless steel, and housing panels 244, 246 and electric box 248 are manufactured of commercial stainless steel sheet. All panels are easily detachable for ventilator inspection, preventative and corrective maintenance, cleaning, and sanitization, which is an advantage of the present invention, as is the fact that the ventilator can operate safely without the panels screwed in place.

Figure 29:
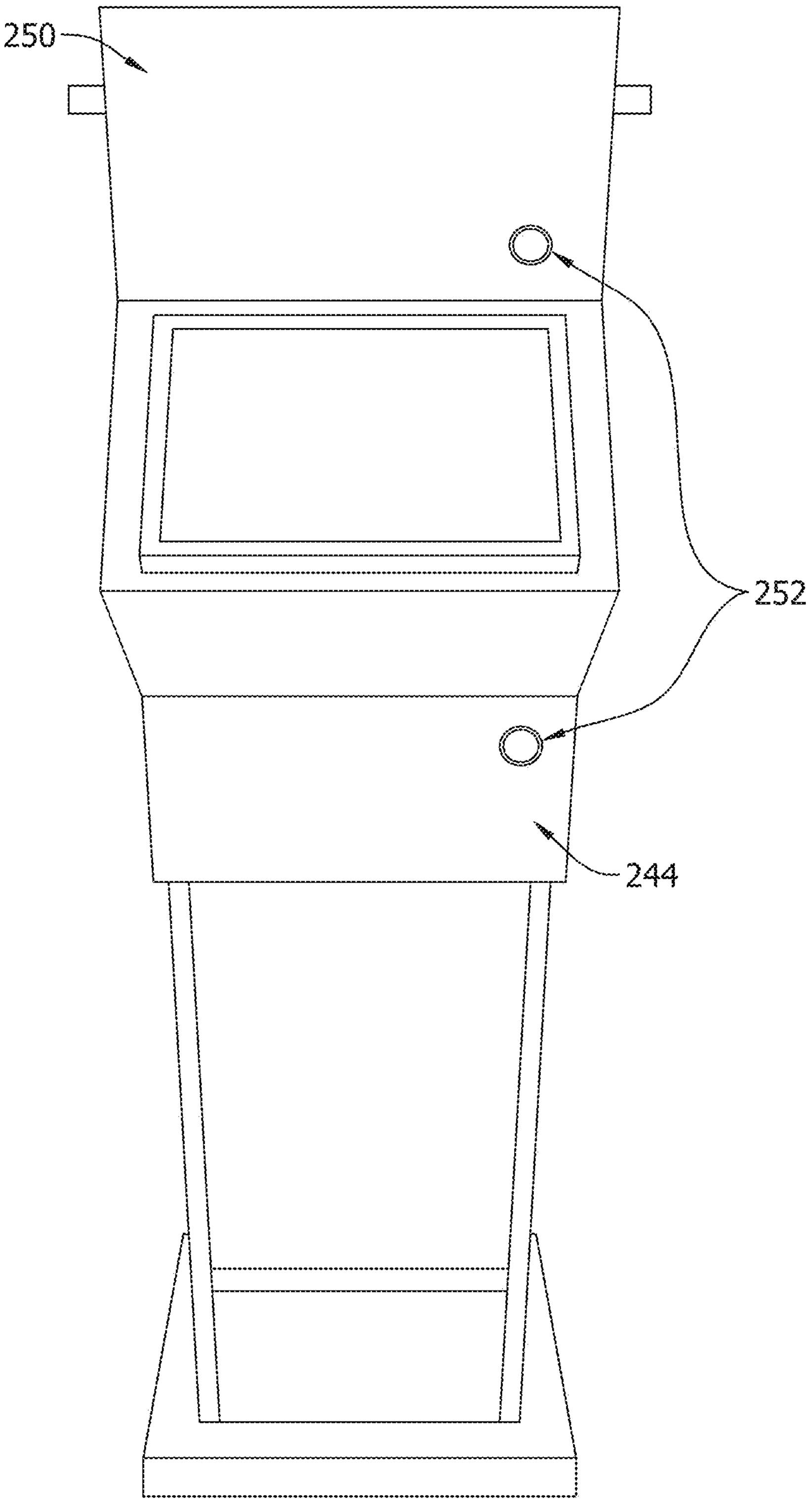

As seen in FIG. 29, a front panel 250 is hinged and can be opened safely during operation unscrewing knobs 252, permitting operator to see the ventilator diaphragms moving cyclically resembling the operation of human diaphragms.

Figure 30:
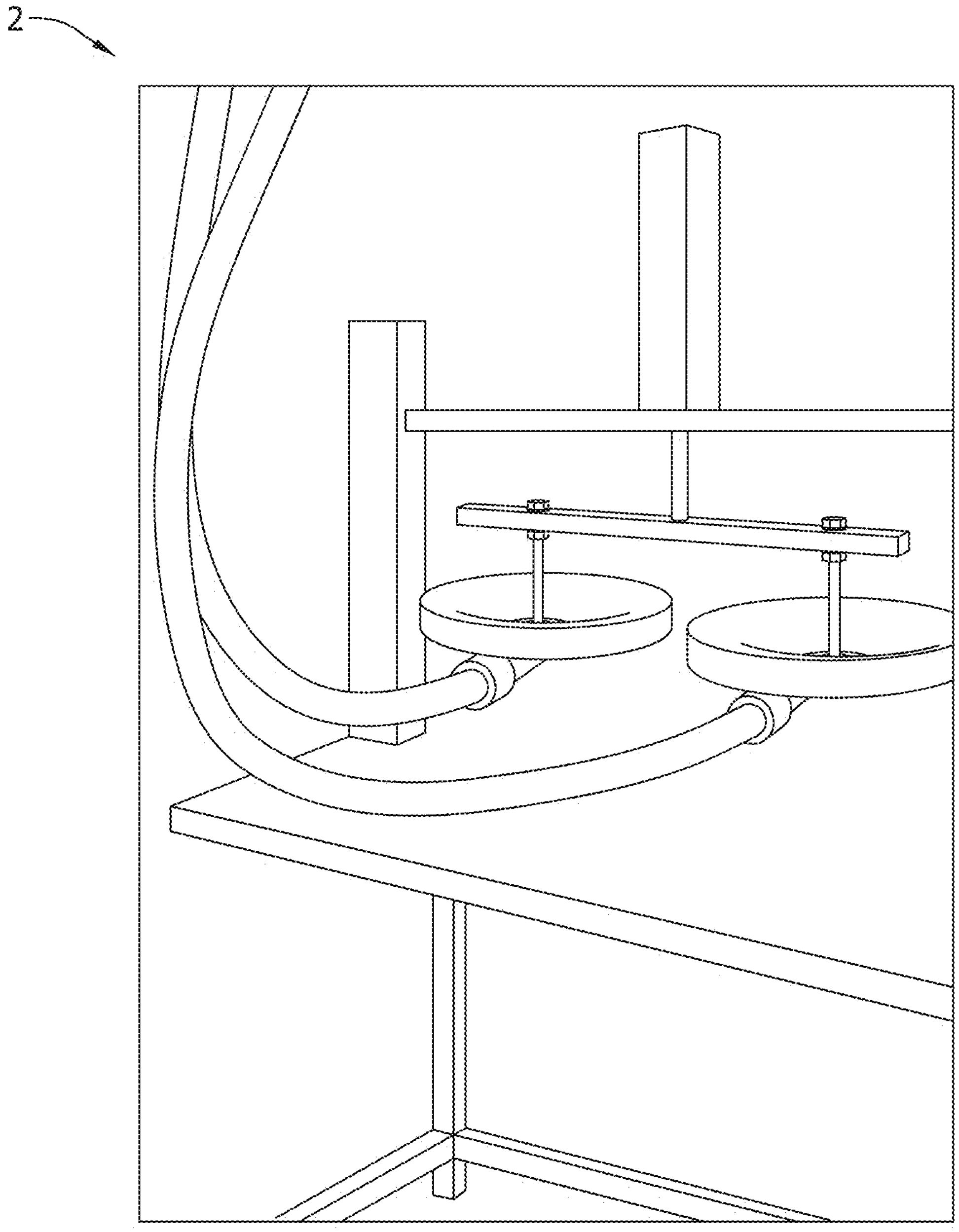
Figure 31:
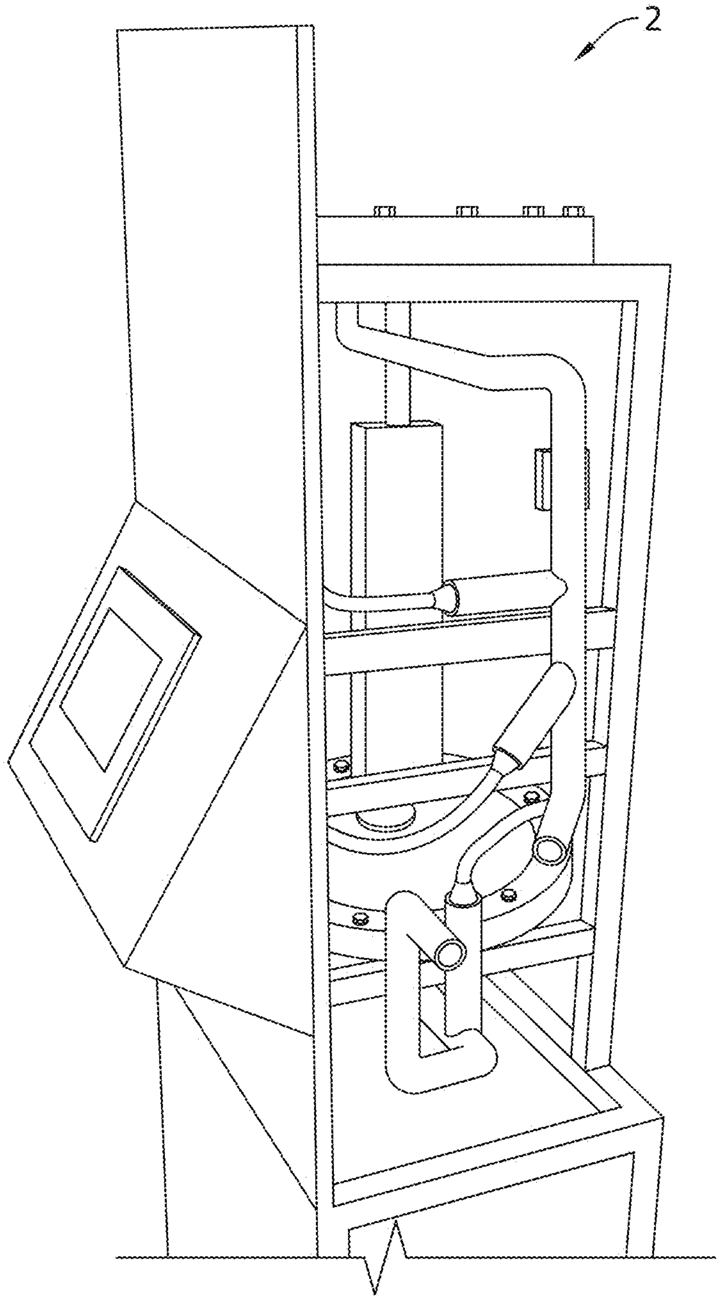
Figure 32:
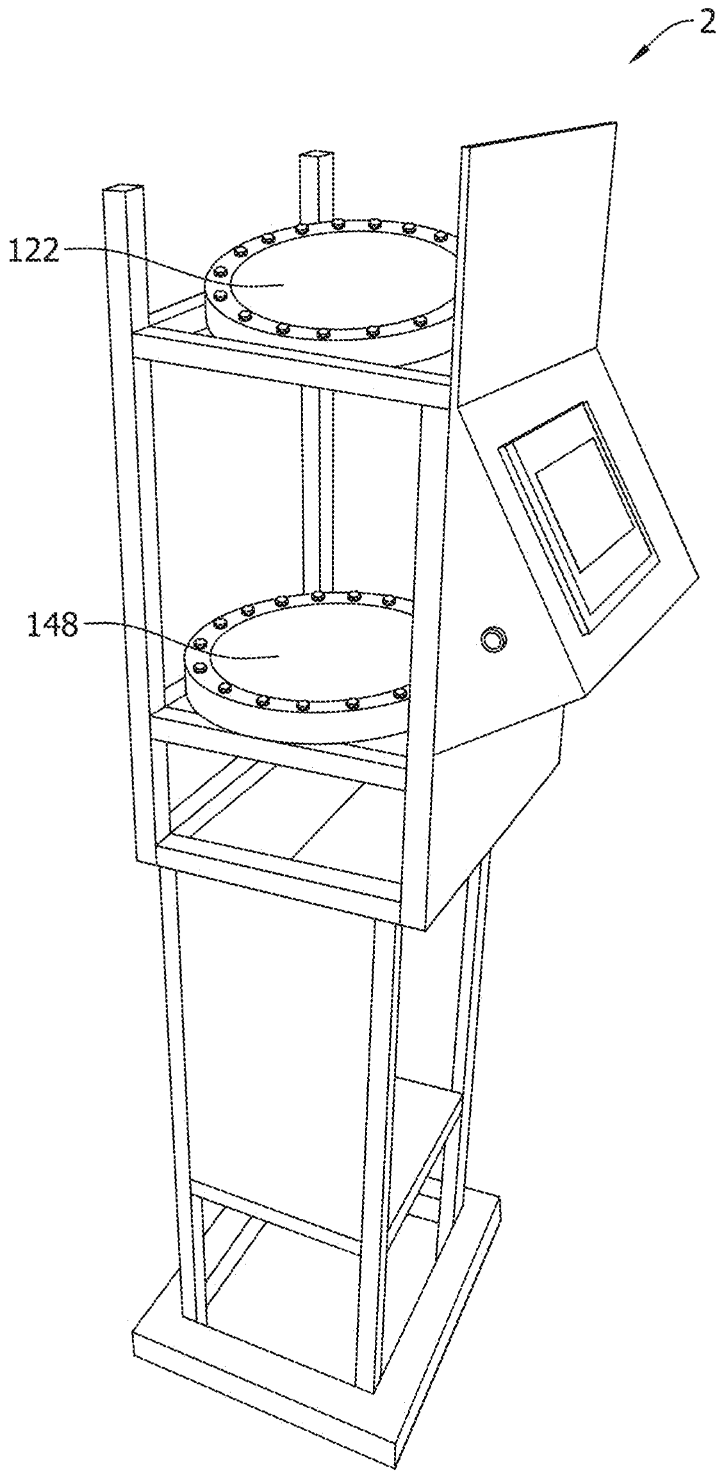
Figure 33:
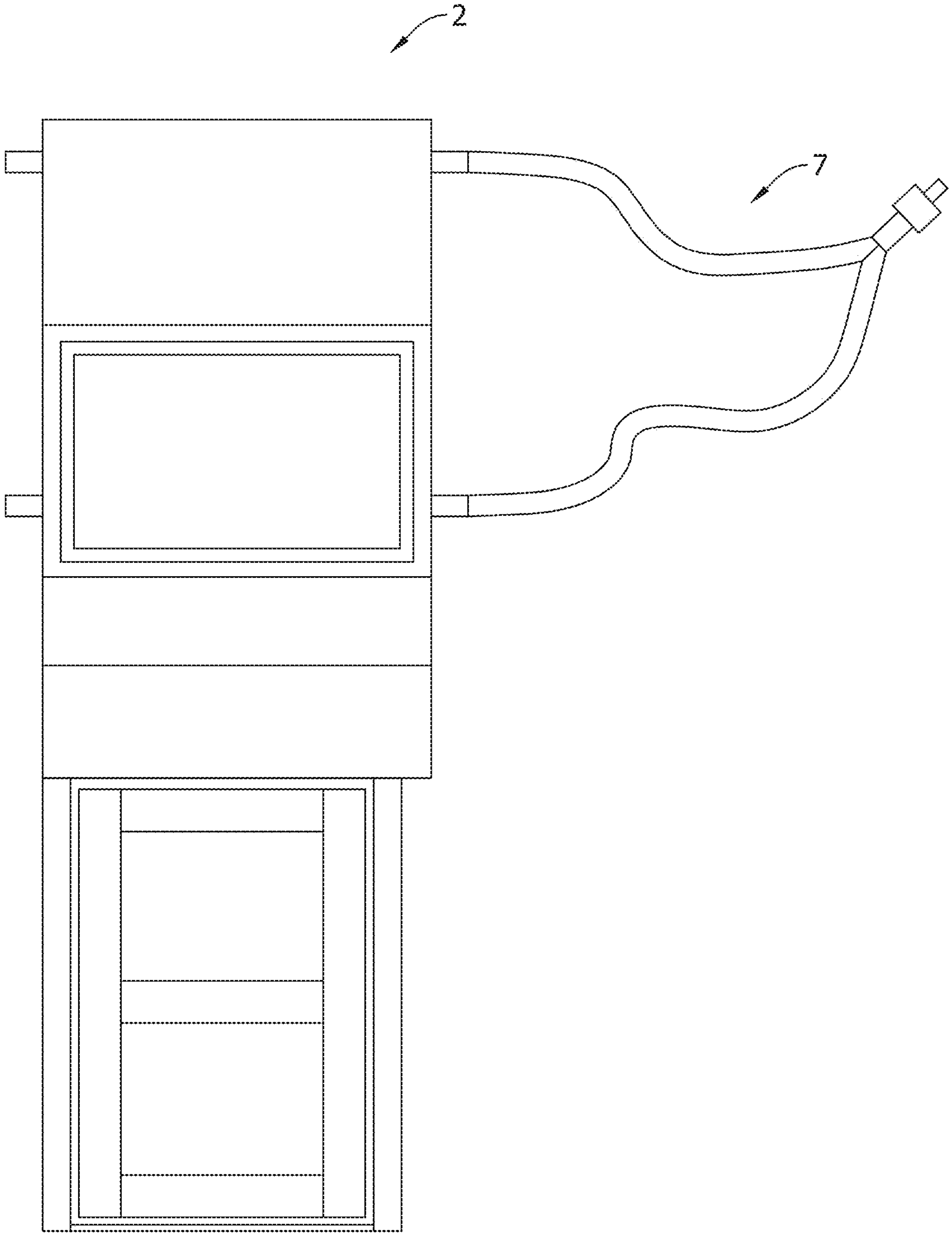
Figure 34:
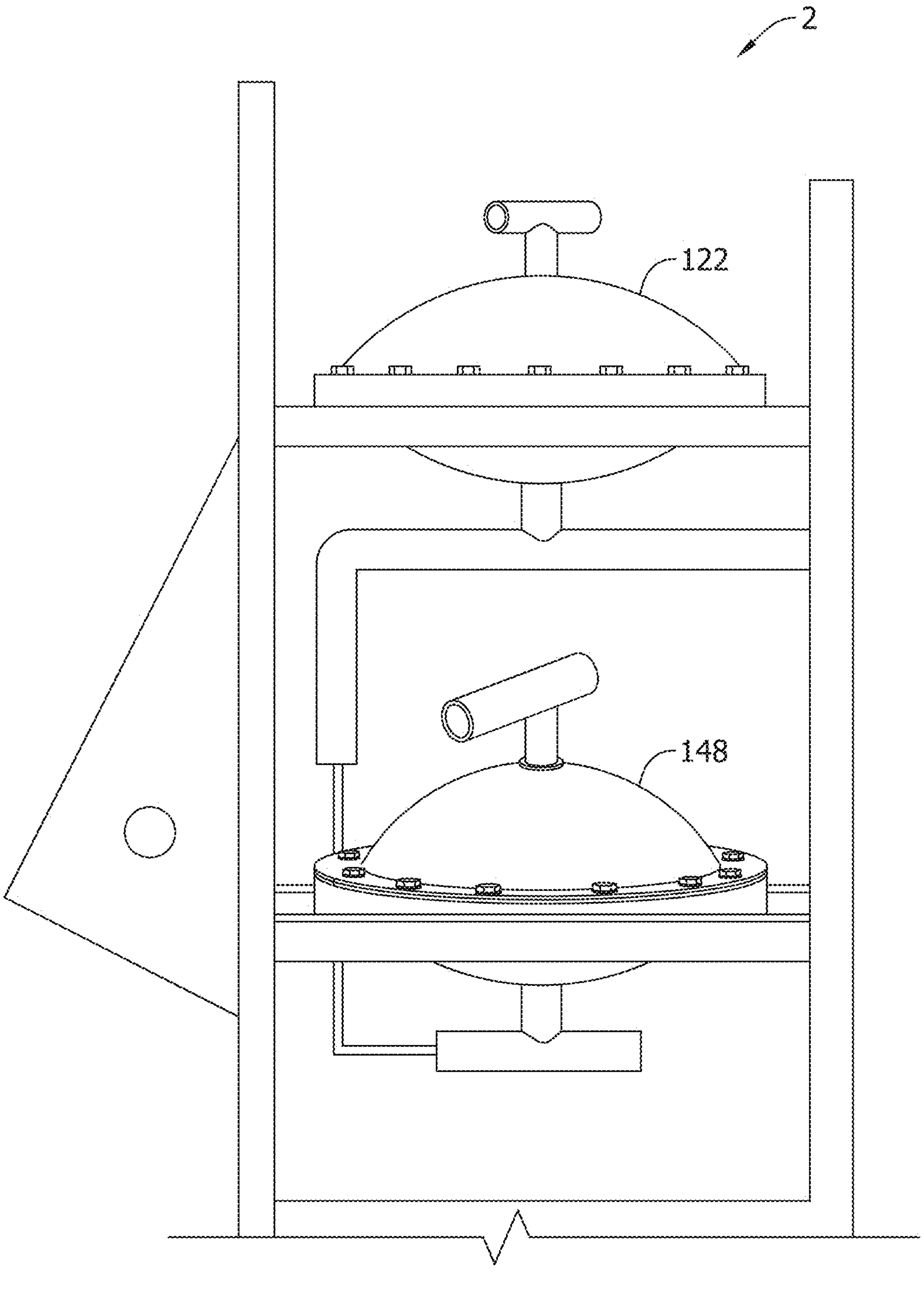
Figure 35:
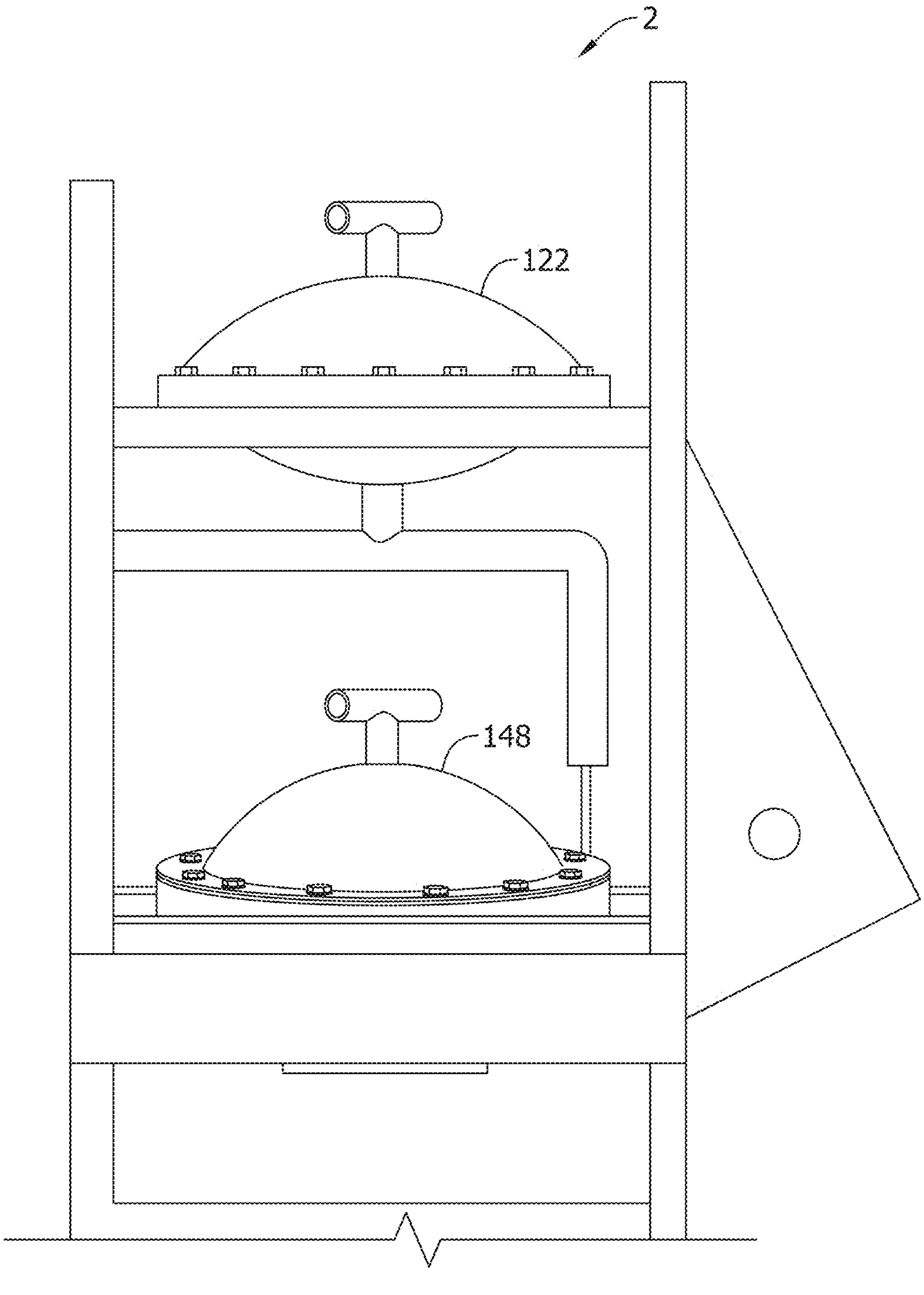
Figure 36:
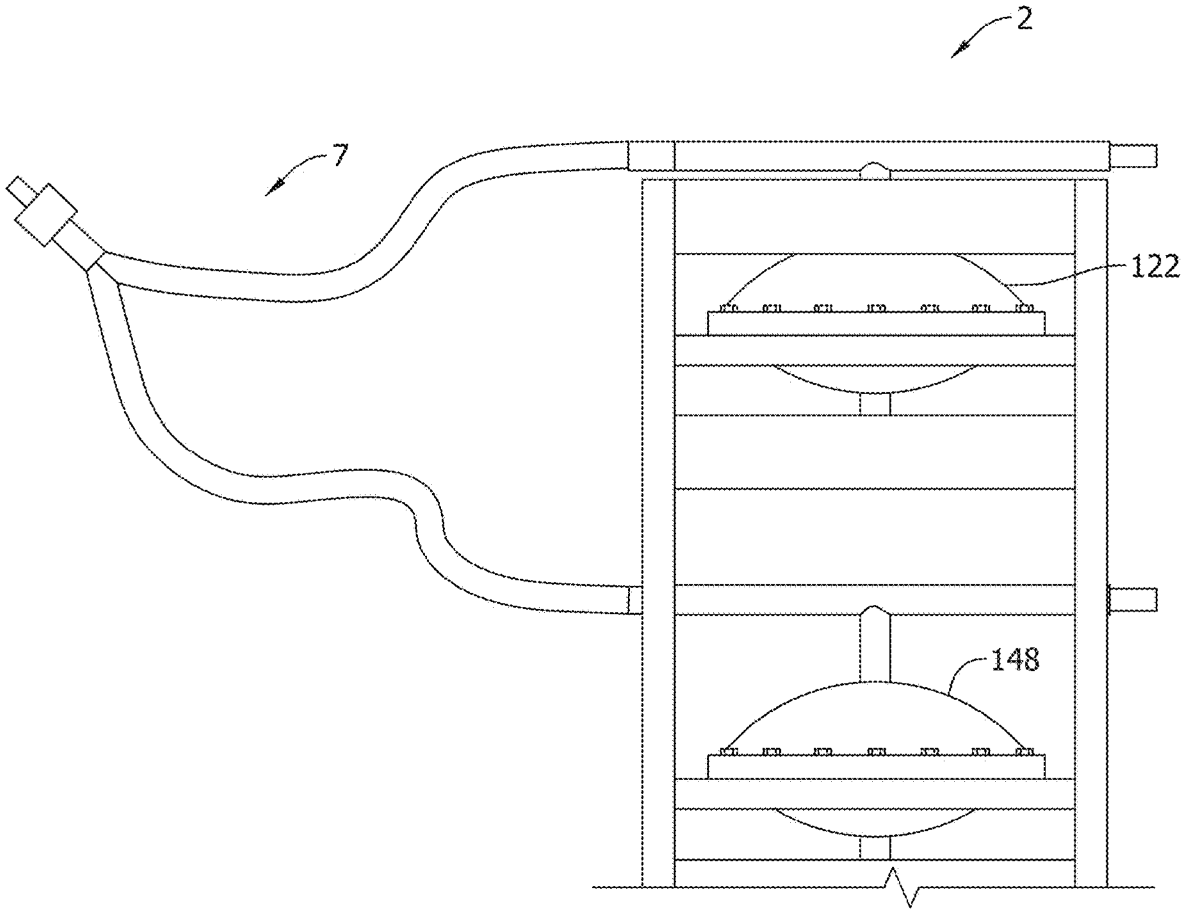
Figure 37:
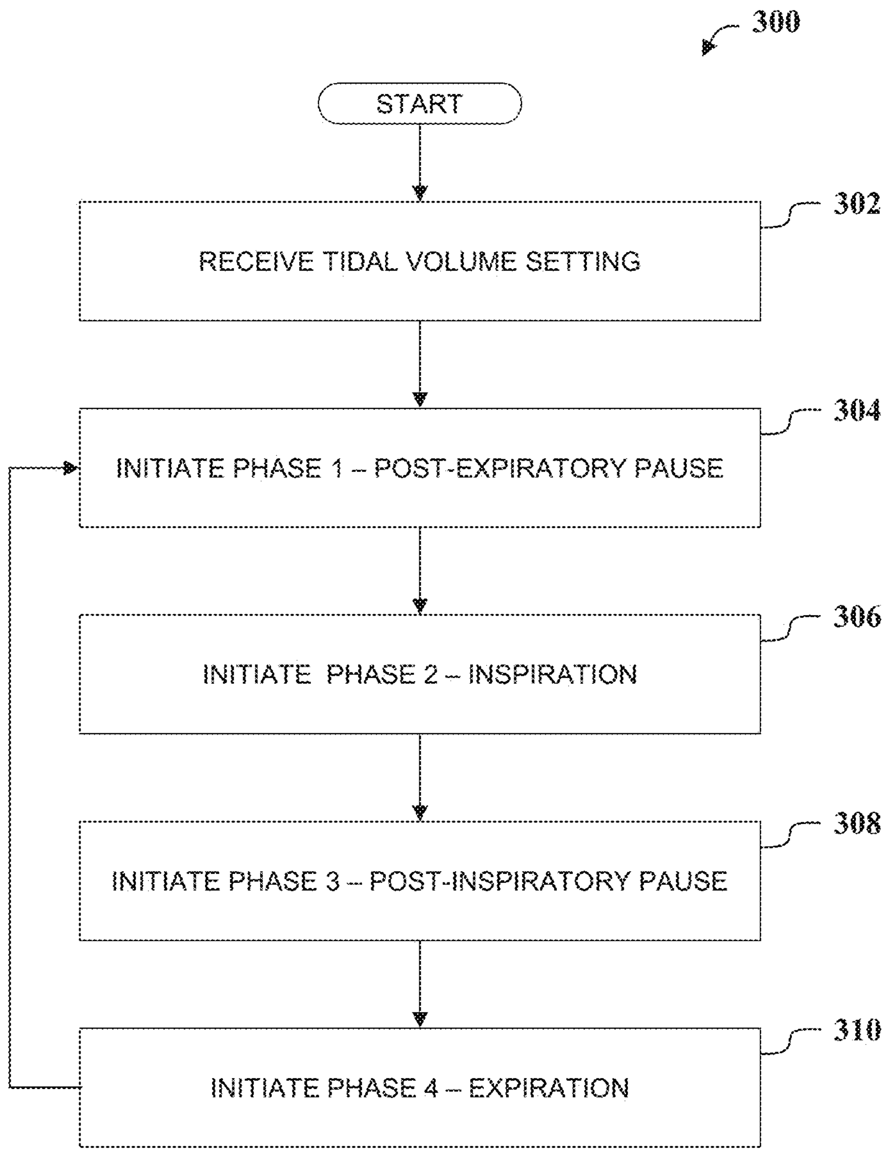
Figure 39:
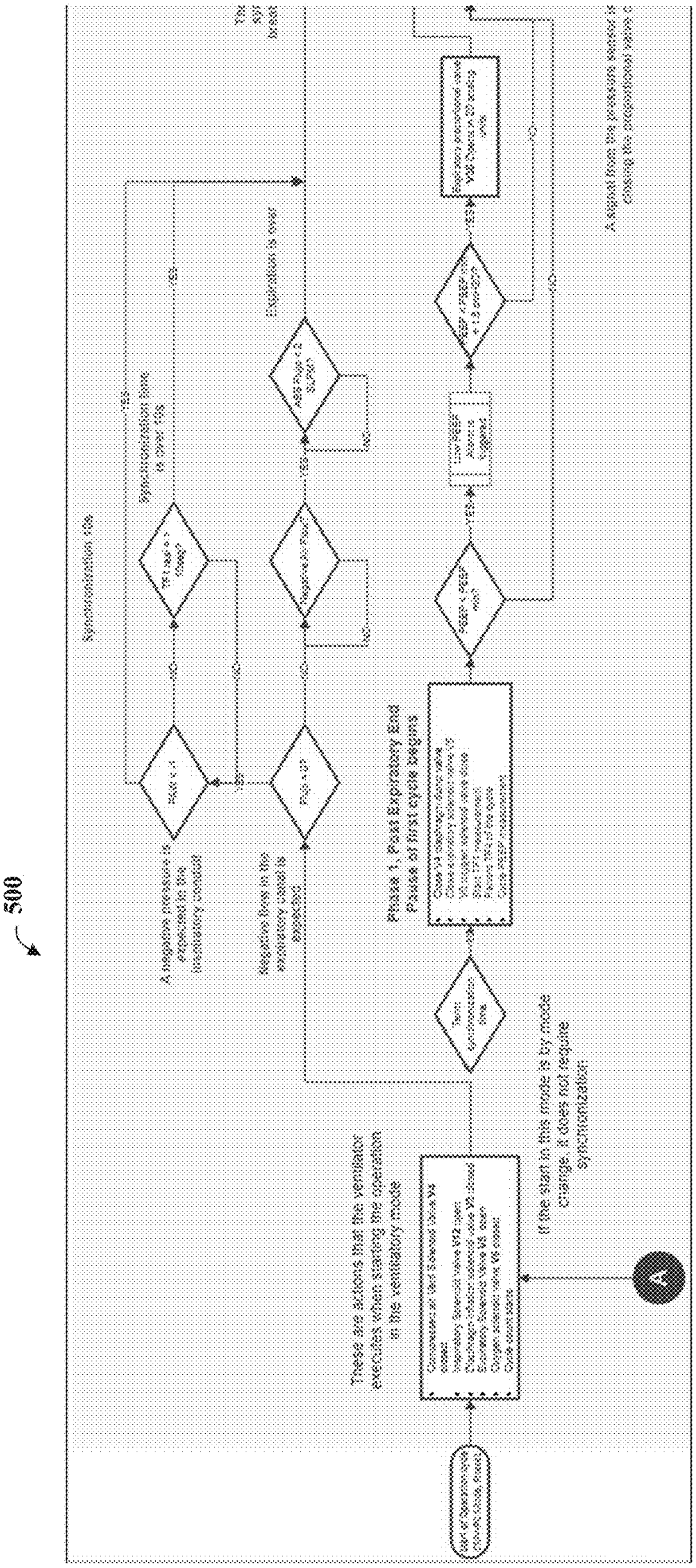
Figure 39:
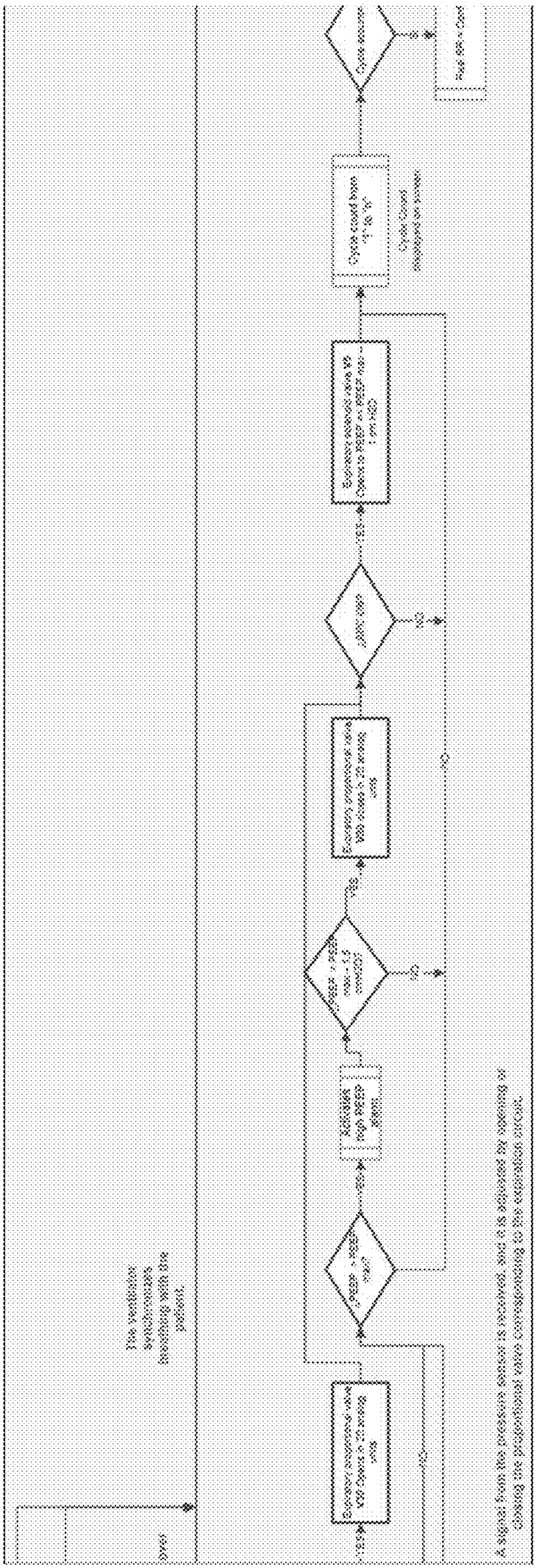
Figure 39:
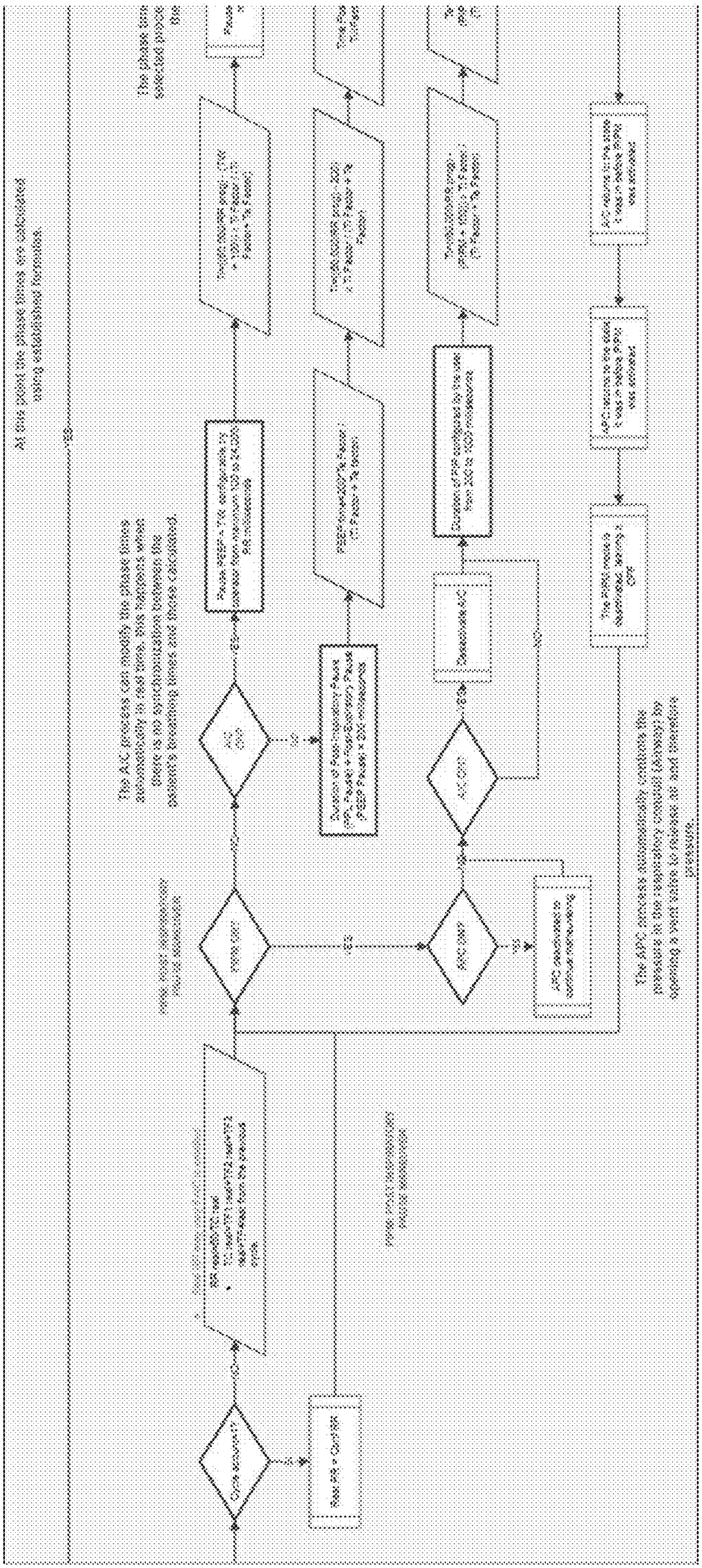
Figure 39:
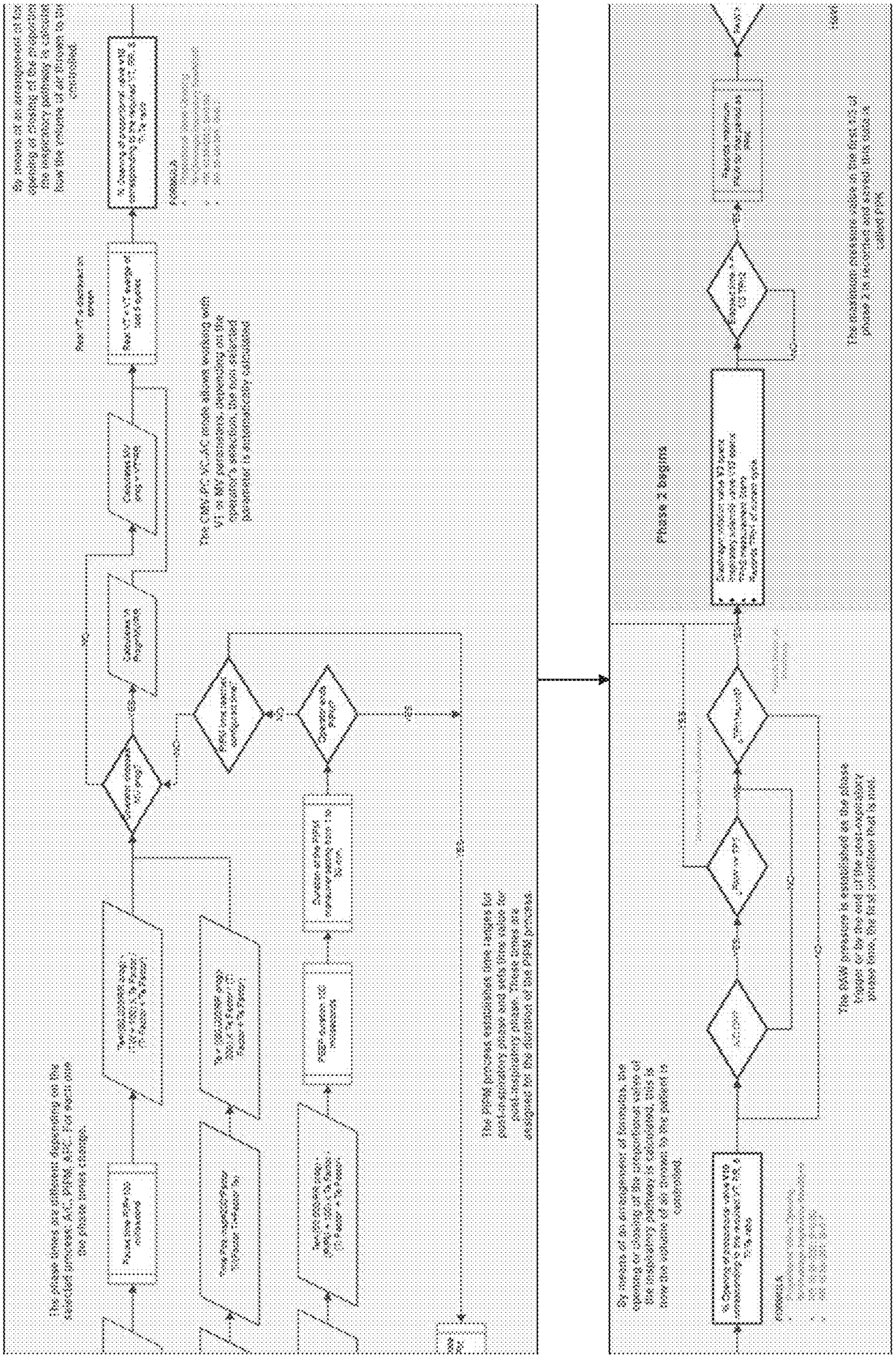
Figure 39:
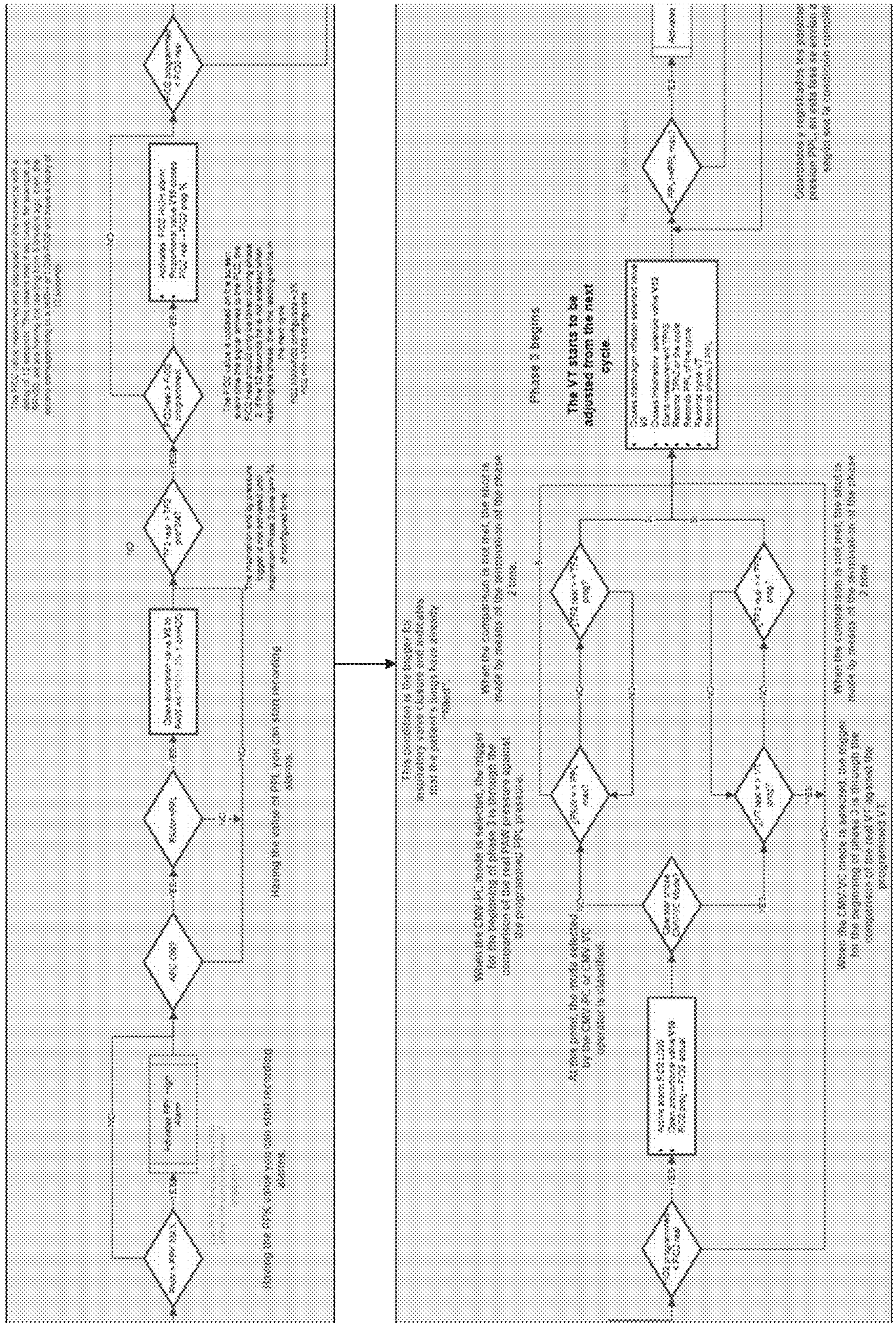
Figure 39:
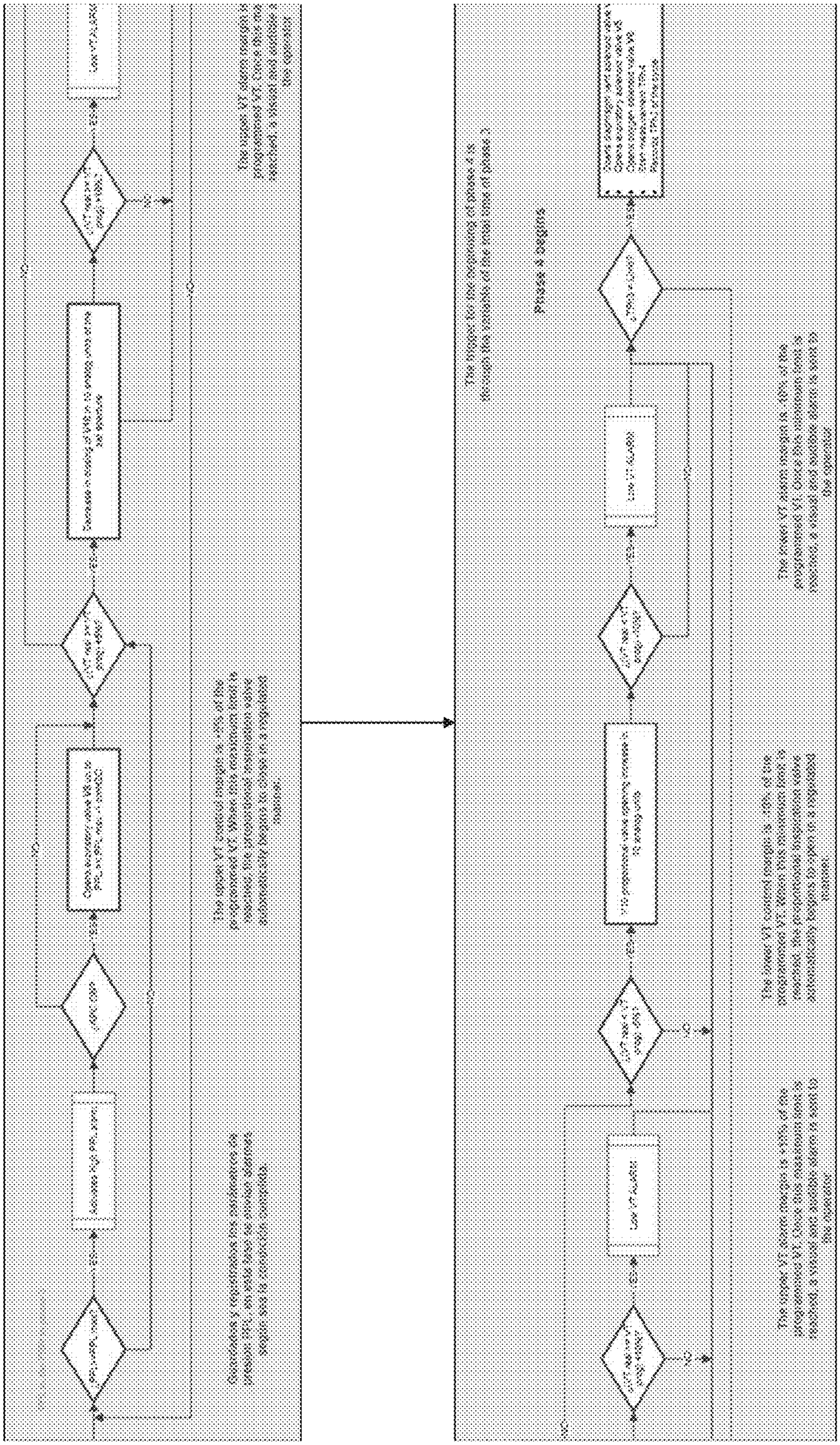
Figure 39:
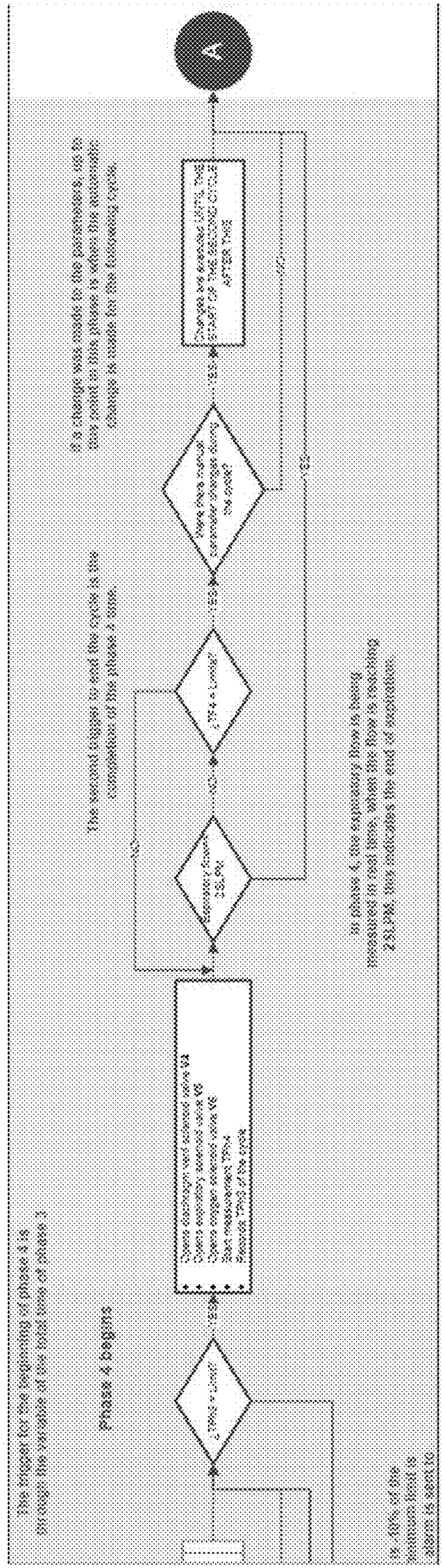

FIGS. 30 and 31, show two different configurations that are possible with the present invention. The main difference is that the diaphragms movement is done by a reciprocal movement element which can be powered by a pneumatic or electric actuator, or by a reciprocating mechanism such as a slider-crank one.

It is important to point out that medical grade filters already widely in used on ventilators and anesthesia machines can and should be coupled to connectors 204 and 206, and also between Sensor 113 and facemask or cannula.

Figure 20:
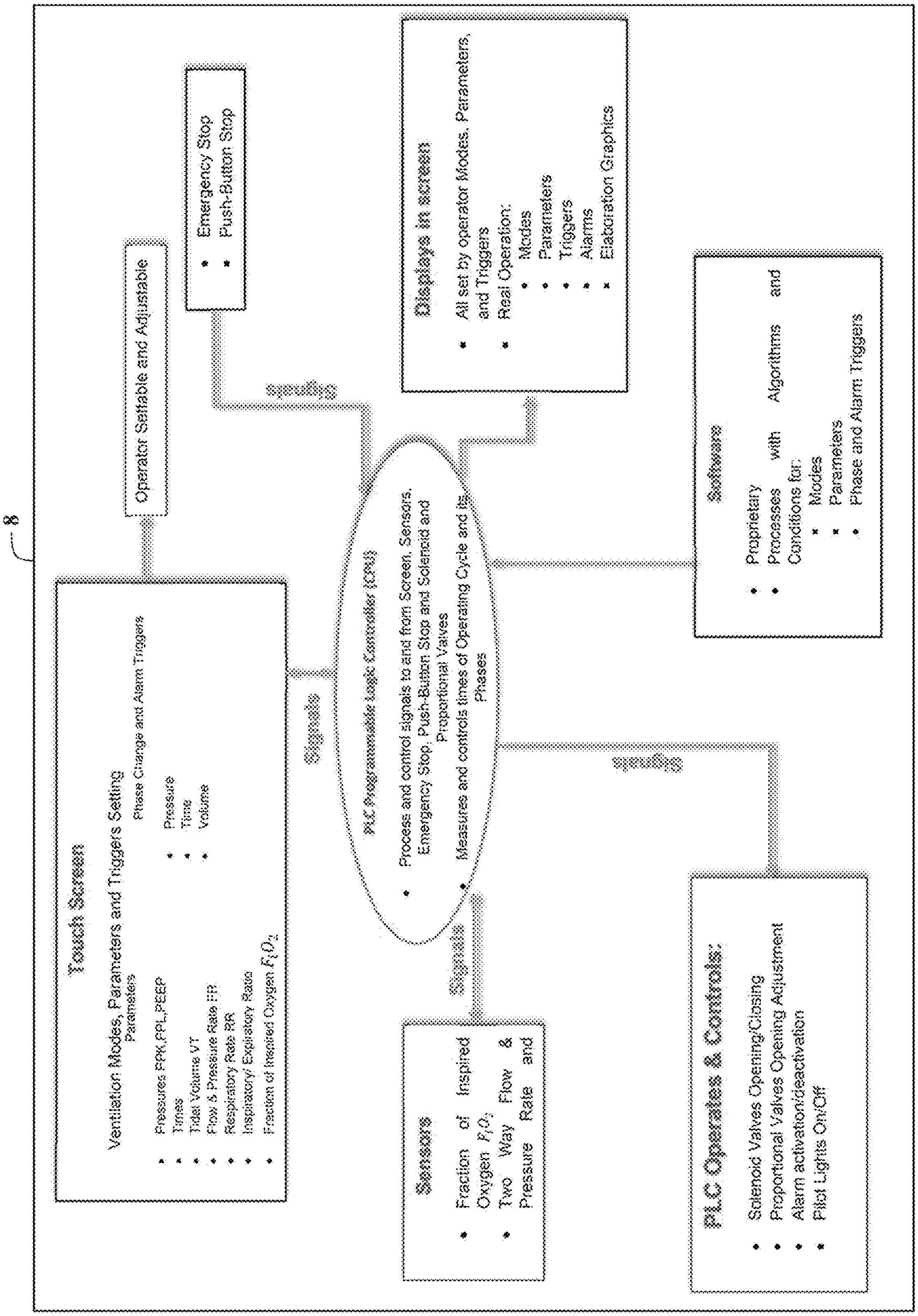
FIG. 20 is a schematic illustration of a control system that may be used with the respirator ventilator device, according to embodiments of the present invention.
Figure 21:
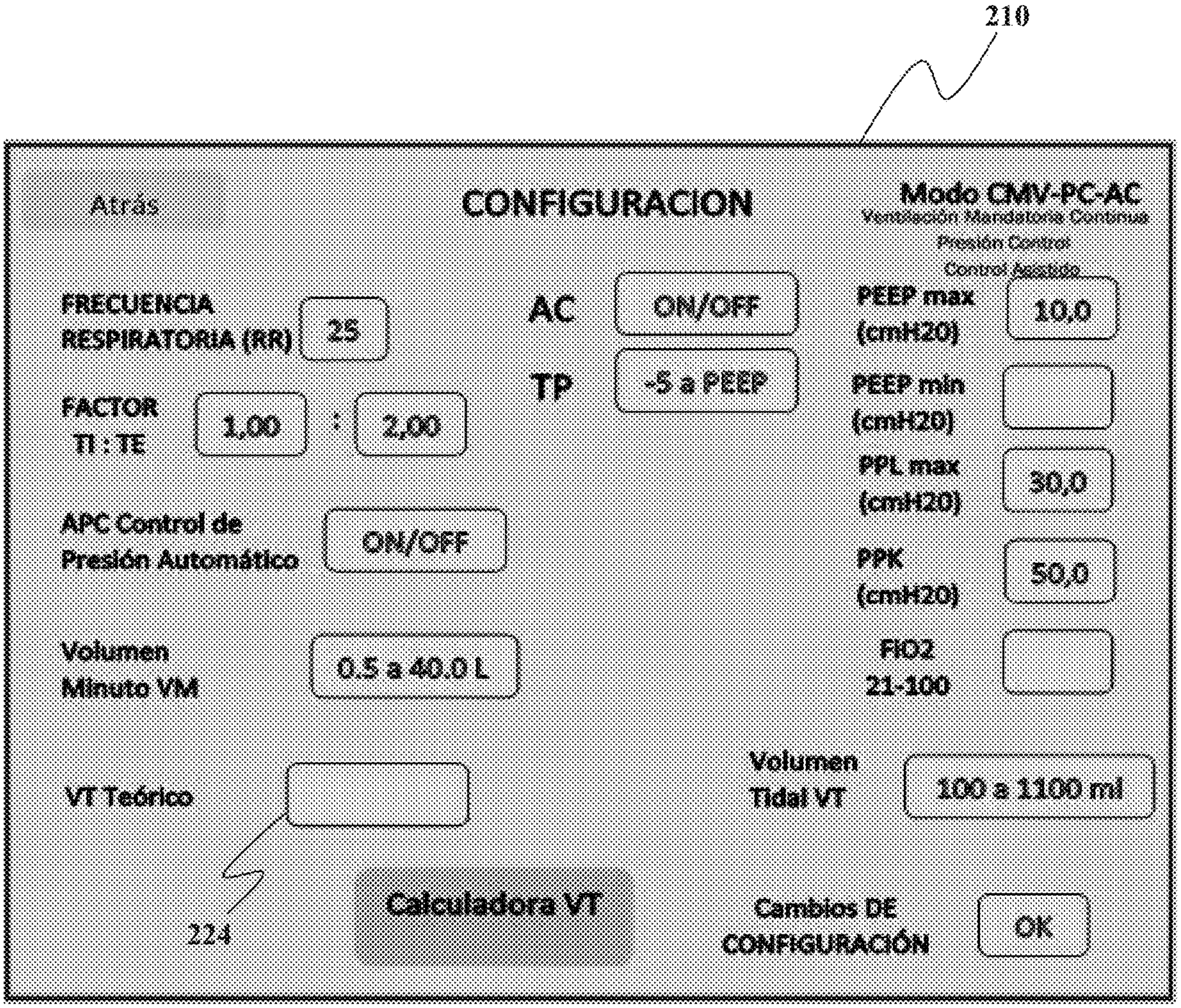
FIGS. 21-22 are schematic illustration of graphical user interfaces that may be displayed by the control system for use in operating the respirator ventilator device, according to embodiments of the present invention.
Figure 22:
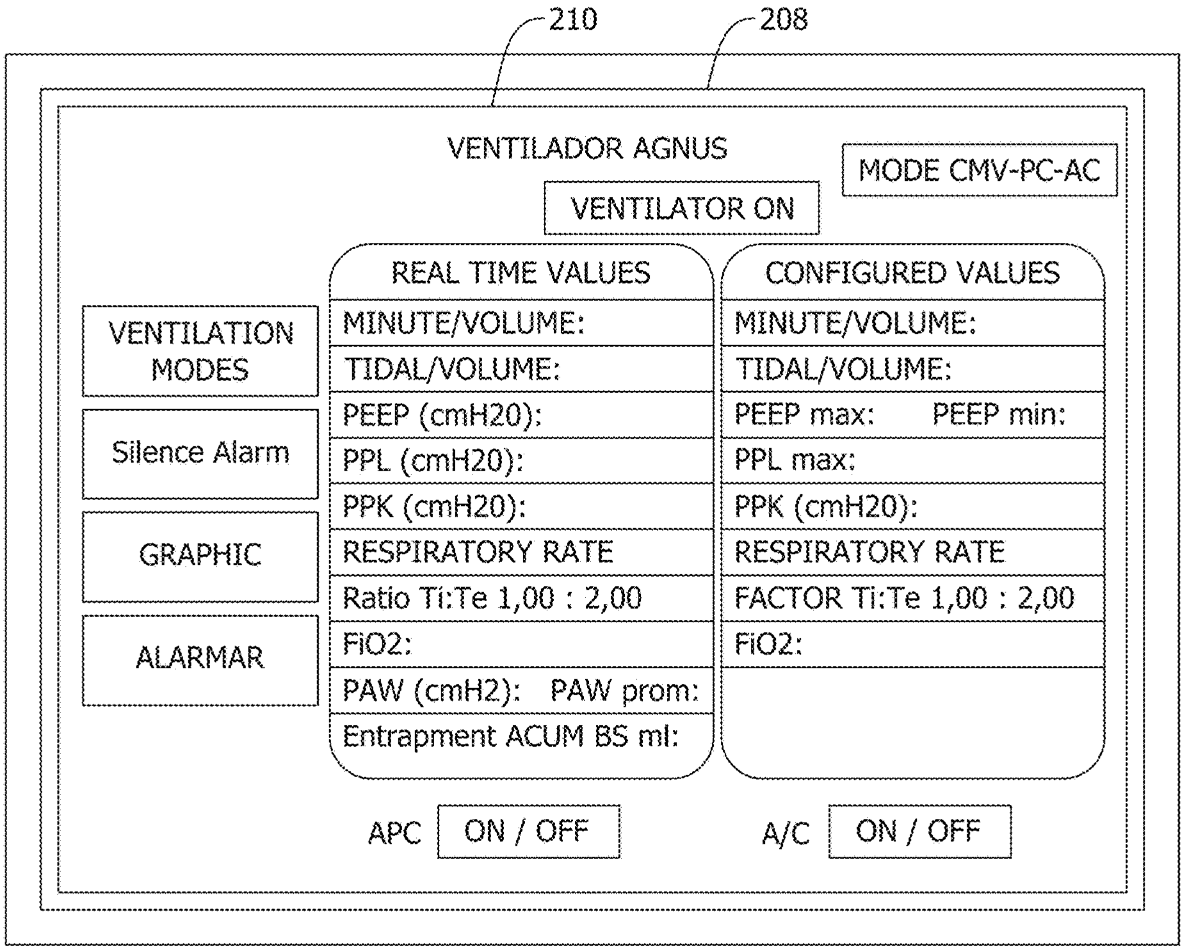

Referring to FIG. 20, it shows a simplified schematic of the electronic control process A respiratory ventilator device that can be used for continuous ventilator support in patients requiring it, in which inhalation breathing air impulsion mechanism and exhaled air removing mechanisms are operated by diaphragms moved inside respective enclosures.

The use of diaphragms and or membranes in any shape or configuration as a breathing air impulsion mechanism in respiratory ventilators and anesthesia machines.

The use of reconfigured diaphragm pumps or compressors to be used as breathing air impulsion mechanism in respiratory ventilators.

Note: It does not use or need bellows, fans, turbofans, or compressed air (medical grade or not) for supplying breathing air.

The respiratory ventilator in that it replicates the human breathing mechanism.

The respiratory ventilator device in which one (or more) diaphragm impulses (pushes, moves, propels) breathing air towards the patient through its inspiration conduit and the attachable respiratory circuit and simultaneously another(s) diaphragm(s) impulses breathed air out of the ventilator through an connector.

As an extension of using diaphragms to move the breathing air, which is a positive displacement mechanism, the use of any kind of positive displacement blowers—e.g. Roots type—as a breathing air moving mechanism in respiratory ventilators and or anesthesia machines.

The respiratory ventilator device physical characteristics and configuration of its components that permit its fabrication without specialized equipment, tools or machinery.

The use of industrial strength, resistance, reliability and duration components and materials.

The respiratory ventilator device includes an inspiration air sub-system, an expiration air assembly, and a mechanical and Electric/electronic control system operatively coupled to operate the ventilator systems and modes. Both inspiration and expiration sub-systems have as a key breathing air moving element a diaphragm each, which are enclosed in a two semi-spherical casket chamber each, replicating the human breathing mechanism. The inspiration air sub-system can be connected to a patient respiratory circuit to deliver a volume of inspiration air to provide continuous inspiration ventilator support to the patient. The expiration air subsystem can be connected to a patient respiratory circuit to assist in a patient expiration. The ventilator construction is configured to operate the respiratory ventilator system in an inspiration phase, a post-inspiratory pause phase, an expiration phase, and a post-expiratory pause phase, facilitating the programming of the CPU (PLC) to permit the ventilator operator to configure and control all the operation variables and their alarms, such as inspiratory, expiratory, post-inspiratory and post-expiratory times, pressures—PEEP, PPK, PPL—, and volumes; Inspired Oxygen Fraction—$FiO_2$—, and respiration frequency—respirations per minute—.

The respiratory ventilator device 2 provides: inspiration and expiration air impulsion mechanism similar to that of alveoli; multiple ventilation modes that cover ICU current requirements; each ventilation mode has its own configuration and operation screens; straight forward operation in all modes; safe and easy Recruitment Maneuver execution; automatic adjustment of Minute Volume in response to variations in pressure; and automatic Pressure Control when Airway Pressure exceeds established limits.

The respiratory ventilator device 2 operates in ventilation Modes including: 1) Continuous Mandatory Ventilation (CMV) including 4 sub-modes: i) CMV-VC Volume Control; ii) CMV-VC-A/C VC & Assist/Control; iii) CMV-PC Pressure Control; and iv) CMV-PC-A/C PC & Assist Control; 2) Continuous Spontaneous Ventilation (CSV) including: i) SPN-PS/VS Pressure and volume Support and ii) Automatic return to previous mode; and 3) Intermittent Minute Mandatory Volume Ventilation (IMMVV-VPC) including A/C-PC/VC/TC.

The respiratory ventilator device 2 provides advantages over known ventilators including: Large Emergency Stop button easily accessible external to screen. Automatically opens expiratory valve and closes the inspiratory impulsion valve allowing spontaneous respiration with ambient air; Large Pilot lights, external to the screen and with high visibility, that signal if the Ventilator is in Expiration or inspiration phase, allowing operator to see from a distance that ventilator is operating; Large Push-button external to screen that allows operator to momentaneously stop Ventilator operation, closing the expiration valve. This is helpful for checking airway pressures at different respiratory phases, and performing an instant recruitment maneuver; Rigid steel Ventilator structure of industrial resistance quality; Pressure and flow pattern similar to an alveolus; Airway pressure (PPK, PPL, PEEP) reduction mechanism with minimum alteration of flow volume; Inspiration support pressure pattern similar to alveoli; Recruitment Maneuver easily configured with several safety features; Spontaneous Mode with automatic return to previous mode at Trigger Window's end in case an inspiration is not triggered. Configurable by operator with just a button; Self-adjustable Tidal Volume VT in case of variation in all ventilation modes; Visual and audible alarms, external to screen, with high visibility; Automatic opening of expiratory valve in case of compressed air failure, permitting spontaneous respiration with ambient air; Compressed air supply can be of standard quality. Medical grade is not necessary because it is not used for respiration in respiration airway; and In case of electric power failure, inspiration and expiration airways remain open permitting spontaneous respiration with ambient air.

| Glossary: | |
|---|---|
| MV | Minute Volume ml: Is the total of inspired air in a minute. It is the result of multiplying VT × RR. |
| VT | Tidal Volume ml: It is the volume of each inspiration. |
| Ti | Inspiratory vs. Expiratory times ratio, adjustable from 1:4 to 4:1 |
| Te | Inspiratory vs. Expiratory times ratio, adjustable from 1:4 to 4:1 |
| RR | Respiratory Rate min: it is the number of respirations -respiratory cycles- per minute. |
| PPK | Peak Pressure cm H2O: Is the minimum pressure in the airway during inspiration. |
| PPL | Plateau Pressure cm H2O: is the pressure in Airway in the pause after inspiration before the expiration starts |
| PEEP | Post-Expiratory End Pressure cm H2O: Is the Post Expiratory End Pressure in airway before inspiration starts, airway is the conduit of breathing air, comprised of the respiratory circuit and the patient's respiratory system |
| PAW | Airway Pressure cm H2O: |
| FiO2 | Fraction of Inspired Oxygen %: Fraction of oxygen in the volume being measured. |
| ABS | Absolute value. |
| APC | Automatic Pressure Control |
| TP | Trigger Pressure: If A/C push button is not activated, TP Trigger Pressure Will remain shaded and inactive. If it is activated, operator will have to enter desired TP. |
| TW | Trigger Window: If A/C is activated, then the Trigger Window time must be entered by operator, with a set maximum of 24,000/RR milliseconds. |
| CVM-PC-A/C | Continuous Mandatory Ventilation Pressure Control Assist/Control |
| CMV-VC-A/C | Continuous Mandatory Ventilation Volume Control Assist/Control |
| CSV-CPAP | Continuous Spontaneous Ventilation- Continuous Positive Airway Pressure |
| CSV-BiPAP | Continuous Spontaneous Ventilation-Bilevel Positive Airway Pressure |
| SIMMV-VPC | Spontaneous Intermittent Mandatory Minute Volume Ventilation |
| RM | Recruitment Mode |
| PIPM | Post-inspiratory Pause Maneuver |
| A/C | Assist/Control |
| ACUM | Accumulated |
| PLC | Programmable Logic Controller |
| V | Valve |
| Operator | The person operating the Ventilator |

A controller, computing device, or computer, such as described herein, includes at least one or more processors or processing units and a system memory. The controller typically also includes at least some form of computer readable media. By way of example and not limitation, computer readable media may include computer storage media and communication media. Computer storage media may include volatile and nonvolatile, removable and non-removable media implemented in any method or technology that enables storage of information, such as computer readable instructions, data structures, program modules, or other data. Communication media typically embody computer readable instructions, data structures, program modules, or other data in a modulated data signal such as a carrier wave or other transport mechanism and include any information delivery media. Those skilled in the art should be familiar with the modulated data signal, which has one or more of its characteristics set or changed in such a manner as to encode information in the signal. Combinations of any of the above are also included within the scope of computer readable media.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Other aspects and features of the present invention can be obtained from a study of the drawings, the disclosure, and the appended claims. The invention may be practiced otherwise than as specifically described within the scope of the appended claims. It should also be noted, that the steps and/or functions listed within the appended claims, notwithstanding the order of which steps and/or functions are listed therein, are not limited to any specific order of operation.

The above description of illustrated examples of the present invention are not intended to be exhaustive or to be limitation to the precise forms disclosed. While specific embodiments of, and examples for, the invention are described herein for illustrative purposes, various equivalent modifications are possible without departing from the broader spirit and scope of the present invention.

What is claimed is:

1. A respiratory ventilator device, comprising:

a housing;

an inhaled air assembly coupled to the housing and including an injector diaphragm housing including a flexible injector diaphragm dividing an interior volume of the injector diaphragm housing into an inhalation air chamber containing inhalation air and a compressed air chamber for containing compressed air;

an inhalation inlet line coupled to the injector diaphragm housing for channeling the inhalation air from a supply of inhalation air into the inhalation air chamber;

an inhalation outlet line coupled to the injector diaphragm housing for delivering the inhalation air from the inhalation air chamber to a patient respiratory circuit;

an exhaled air assembly coupled to the housing and including:

an extractor diaphragm housing including a flexible extractor diaphragm dividing an extractor interior volume of the extractor diaphragm housing into an exhalation air chamber and a second compressed air chamber;

an exhalation inlet line coupled to the extractor diaphragm housing for channeling exhaled air from the patient respiratory circuit into the exhalation air chamber; and an exhalation outlet line coupled to the extractor diaphragm housing for delivering the exhaled air from the exhalation air chamber to an exhaust air collection system;

a pneumatic compressed air assembly coupled to the injector diaphragm housing and the extractor diaphragm housing;

a control system operatively coupled to the pneumatic compressed air assembly, the control system including a processor programmed to execute an algorithm for operating the respiratory ventilator device including the steps of:

operating the pneumatic compressed air assembly in a first phase including the injector diaphragm and the extractor diaphragm in a center position; and operating the pneumatic compressed air assembly in a second phase including delivering compressed air into the injector diaphragm housing to move the flexible injector diaphragm to channel inhalation air from the injector diaphragm housing to the patient respiratory circuit.

2. The respiratory ventilator device of claim 1, wherein the processor is programmed to execute the algorithm further including the steps of;

operating the pneumatic compressed air assembly in the second phase after a predetermined period of time.

3. The respiratory ventilator device of claim 1, wherein the processor is programmed to execute the algorithm further including the steps of:

operating the pneumatic compressed air assembly in a third phase including maintaining the flexible injector diaphragm in a flexed position.

4. The respiratory ventilator device of claim 3, further including a sensor assembly coupled to the inhaled air assembly for measuring an air flow volume delivered to the patient respiratory circuit, the processor is programmed to execute the algorithm further including the steps of:

operating the pneumatic compressed air assembly in the third phase upon determining the measured an air flow volume delivered to the patient respiratory circuit equals a predefined tidal volume value.

5. The respiratory ventilator device of claim 4, further including a touchscreen coupled to the housing, the processor is programmed to execute the algorithm further including the steps of:

receiving an operator selected tidal volume value from an operator via the touchscreen; and operating the pneumatic compressed air assembly in the third phase upon determining the measured an air flow volume delivered to the patient respiratory circuit equals the operator selected tidal volume value.

6. The respiratory ventilator device of claim 3, wherein the processor is programmed to execute the algorithm further including the steps of:

operating the pneumatic compressed air assembly in a fourth phase to release pneumatic pressure from the injector diaphragm to allow another volume of inhalation air to enter the injector diaphragm housing from the supply of inhalation air.

7. The respiratory ventilator device of claim 6, wherein the processor is programmed to execute the algorithm further including the steps of:

operating the pneumatic compressed air assembly in the fourth phase after a predetermined period of time.

8. A method of operating a respiratory ventilator device including an inhaled air assembly including an injector diaphragm housing including a flexible injector diaphragm dividing an interior volume of the injector diaphragm housing into an inhalation air chamber containing inhalation air and a compressed air chamber for containing compressed air, an inhalation inlet line coupled to the injector diaphragm housing for channeling the inhalation air from a supply of inhalation air into the inhalation air chamber, and an inhalation outlet line coupled to the injector diaphragm housing for delivering the inhalation air from the inhalation air chamber to a patient respiratory circuit, an exhaled air assembly including an extractor diaphragm housing including a flexible extractor diaphragm dividing an extractor interior volume of the extractor diaphragm housing into an exhalation air chamber and a second compressed air chamber, an exhalation inlet line coupled to the extractor diaphragm housing for channeling exhaled air from the patient respiratory circuit into the exhalation air chamber, and an exhalation outlet line coupled to the extractor diaphragm housing for delivering the exhaled air from the exhalation air chamber to an exhaust air collection system, a pneumatic compressed air assembly coupled to the injector diaphragm housing and the extractor diaphragm housing, and a control system including a processor operatively coupled to the pneumatic compressed air assembly, the method including the processor performing an algorithm for operating the respiratory ventilator device including the steps of:

operating the pneumatic compressed air assembly in a first phase including the injector diaphragm and the extractor diaphragm in a center position; and operating the pneumatic compressed air assembly in a second phase including delivering compressed air into the injector diaphragm housing to move the flexible injector diaphragm to channel inhalation air from the injector diaphragm housing to the patient respiratory circuit.

9. The method of claim 8, including the processor performing the algorithm further including the steps of:

operating the pneumatic compressed air assembly in the second phase after a predetermined period of time.

10. The method of claim 8, including the processor performing the algorithm further including the steps of;

operating the pneumatic compressed air assembly in a third phase including maintaining the flexible injector diaphragm in a flexed position.

11. The method of claim 10, wherein the respiratory ventilator device includes a sensor assembly coupled to the inhaled air assembly for measuring an air flow volume delivered to the patient respiratory circuit, the method including the processor performing the algorithm further including the steps of:

operating the pneumatic compressed air assembly in the third phase upon determining the measured an air flow volume delivered to the patient respiratory circuit equals a predefined tidal volume value.

12. The method of claim 11, wherein the respiratory ventilator device includes a touchscreen coupled to the housing, the method including the processor performing the algorithm further including the steps of:

receiving an operator selected tidal volume value from an operator via the touchscreen; and operating the pneumatic compressed air assembly in the third phase upon determining the measured an air flow volume delivered to the patient respiratory circuit equals the operator selected tidal volume value.

13. The method of claim 10, including the processor performing the algorithm further including the steps of:

operating the pneumatic compressed air assembly in a fourth phase to release pneumatic pressure from the injector diaphragm to allow another volume of inhalation air to enter the injector diaphragm housing from the supply of inhalation air.

14. The method of claim 13, including the processor performing the algorithm further including the steps of:

operating the pneumatic compressed air assembly in the fourth phase after a predetermined period of time.

15. A non-transitory computer-readable storage media having computer-executable instructions embodied thereon to operate a respiratory ventilator device including an inhaled air assembly including an injector diaphragm housing including a flexible injector diaphragm dividing an interior volume of the injector diaphragm housing into an inhalation air chamber containing inhalation air and a compressed air chamber for containing compressed air, an inhalation inlet line coupled to the injector diaphragm housing for channeling the inhalation air from a supply of inhalation air into the inhalation air chamber, and an inhalation outlet line coupled to the injector diaphragm housing for delivering the inhalation air from the inhalation air chamber to a patient respiratory circuit, an exhaled air assembly including an extractor diaphragm housing including a flexible extractor diaphragm dividing an extractor interior volume of the extractor diaphragm housing into an exhalation air chamber and a second compressed air chamber, an exhalation inlet line coupled to the extractor diaphragm housing for channeling exhaled air from the patient respiratory circuit into the exhalation air chamber, and an exhalation outlet line coupled to the extractor diaphragm housing for delivering the exhaled air from the exhalation air chamber to an exhaust air collection system, a pneumatic compressed air assembly coupled to the injector diaphragm housing and the extractor diaphragm housing, and a control system including a processor operatively coupled to the pneumatic compressed air assembly, when executed by the processor the computer-executable instructions cause the processor to perform an algorithm including the steps of:

operating the pneumatic compressed air assembly in a first phase including the injector diaphragm and the extractor diaphragm in a center position; and operating the pneumatic compressed air assembly in a second phase including delivering compressed air into the injector diaphragm housing to move the flexible injector diaphragm to channel inhalation air from the injector diaphragm housing to the patient respiratory circuit.

16. The non-transitory computer-readable storage media of claim 15, wherein the computer-executable instructions cause the processor to perform the algorithm further including the steps of:

operating the pneumatic compressed air assembly in the second phase after a predetermined period of time.

17. The non-transitory computer-readable storage media of claim 15, wherein the computer-executable instructions cause the processor to perform the algorithm further including the steps of:

operating the pneumatic compressed air assembly in a third phase including maintaining the flexible injector diaphragm in a flexed position.

18. The non-transitory computer-readable storage media of claim 17, wherein the respiratory ventilator device includes a sensor assembly coupled to the inhaled air assembly for measuring an air flow volume delivered to the patient respiratory circuit, the computer-executable instructions cause the processor to perform the algorithm further including the steps of:

operating the pneumatic compressed air assembly in the third phase upon determining the measured an air flow volume delivered to the patient respiratory circuit equals a predefined tidal volume value.

19. The non-transitory computer-readable storage media of claim 18, wherein the respiratory ventilator device includes a touchscreen, the computer-executable instructions cause the processor to perform the algorithm further including the steps of:

receiving an operator selected tidal volume value from an operator via the touchscreen; and operating the pneumatic compressed air assembly in the third phase upon determining the measured an air flow volume delivered to the patient respiratory circuit equals the operator selected tidal volume value.

20. The non-transitory computer-readable storage media of claim 17, wherein the computer-executable instructions cause the processor to perform the algorithm further including the steps of:

operating the pneumatic compressed air assembly in a fourth phase to release pneumatic pressure from the injector diaphragm to allow another volume of inhalation air to enter the injector diaphragm housing from the supply of inhalation air.

* * * * *